(12) United States Patent
Ward et al.

(10) Patent No.: US 8,758,781 B2
(45) Date of Patent: Jun. 24, 2014

(54) TISSUE SCAFFOLDS DERIVED FROM FORESTOMACH EXTRACELLULAR MATRIX

(71) Applicant: Mesynthes Ltd., Lower Hutt (NZ)

(72) Inventors: Brian Roderick Ward, Wellington (NZ); Keryn Dallas Johnson, Wellington (NZ); Barnaby Charles Hough May, Wellington (NZ)

(73) Assignee: Mesynthes Ltd., Lower Hutt (NZ)

( * ) Notice: Subject to any disclaimer, the term of this patent is extended or adjusted under 35 U.S.C. 154(b) by 0 days.

(21) Appl. No.: 13/770,623

(22) Filed: Feb. 19, 2013

(65) Prior Publication Data

US 2013/0224260 A1  Aug. 29, 2013

Related U.S. Application Data

(62) Division of application No. 12/512,835, filed on Jul. 30, 2009, now Pat. No. 8,415,159.

(60) Provisional application No. 61/137,367, filed on Jul. 30, 2008, provisional application No. 61/172,671, filed on Apr. 24, 2009.

(51) Int. Cl.
| | | |
|---|---|---|
| *A61K 35/38* | (2006.01) | |
| *C12N 1/00* | (2006.01) | |
| *A61K 35/00* | (2006.01) | |
| *A61K 35/37* | (2006.01) | |

(52) U.S. Cl.
CPC .............. *C12N 1/00* (2013.01); *C12N 2533/90* (2013.01); *C12N 2320/00* (2013.01); *A61K 35/38* (2013.01); *C12N 2533/00* (2013.01)
USPC ............ 424/400; 424/520; 424/550; 424/551

(58) Field of Classification Search
None
See application file for complete search history.

(56) References Cited

U.S. PATENT DOCUMENTS

| | | | |
|---|---|---|---|
| 4,902,508 | A | 2/1990 | Badylak et al. |
| 4,956,178 | A | 9/1990 | Badylak et al. |
| 5,520,916 | A | 5/1996 | Dorigatti et al. |
| 5,554,389 | A | 9/1996 | Badylak et al. |
| 5,658,582 | A | 8/1997 | Dorigatti et al. |
| 5,916,265 | A | 6/1999 | Hu |
| 5,997,575 | A | 12/1999 | Whitson et al. |
| 6,099,567 | A | 8/2000 | Badylak et al. |
| 6,576,265 | B1 | 6/2003 | Spievack |
| 6,852,339 | B2 | 2/2005 | Spievack |
| 6,869,619 | B2 | 3/2005 | Spievack |
| 6,890,562 | B2 | 5/2005 | Spievack |
| 6,890,563 | B2 | 5/2005 | Spievack |
| 6,893,666 | B2 | 5/2005 | Spievack |
| 7,476,249 | B2 | 1/2009 | Frank |
| 2002/0111576 | A1 | 8/2002 | Greene et al. |
| 2003/0104026 | A1 | 6/2003 | Wironen et al. |
| 2005/0181016 | A1* | 8/2005 | Freyman et al. .............. 424/426 |
| 2006/0121002 | A1 | 6/2006 | Rolland et al. |
| 2007/0088434 | A1 | 4/2007 | Frank |
| 2008/0081362 | A1 | 4/2008 | Keeley et al. |
| 2009/0177133 | A1 | 7/2009 | Kieswetter et al. |
| 2010/0028407 | A1 | 2/2010 | Del Priore et al. |
| 2010/0152730 | A1 | 6/2010 | Makower et al. |
| 2010/0172958 | A1 | 7/2010 | Lucchesi et al. |

FOREIGN PATENT DOCUMENTS

| | | |
|---|---|---|
| EP | 2270912 A2 | 1/2011 |
| WO | 03/007789 A2 | 1/2003 |
| WO | 03/035125 A2 | 5/2003 |
| WO | 2008/016919 A2 | 2/2008 |
| WO | 2009/011856 A1 | 1/2009 |
| WO | 2010/031995 A2 | 3/2010 |

OTHER PUBLICATIONS

Badylak, Stephen F., "The extracellular matrix as a biologic scaffold material," Biomaterials, vol. 28:3587-3593 (2007).

Badylak, Stephen F., "The extracellular matrix as a scaffold for tissue reconstruction," Seminars in Cell & Developmental Biology, vol. 13:377-383 (2002).

Boguszewski, D.V. et al., "Biomechanical Comparison of Abdominal Wall Hernia Repair Materials," ASME Summer Bioengineering Conference (2008).

Choe, J.M. et al., "Autologous, cadaveric, and synthetic materials used in sling surgery: comparative biomechanical analysis," Urology, vol. 58(3):482-486 (2001).

Cloonan, Aidan J. et al., "Sperical indentation of free-standing acellular extracellular matrix membranes," Acta Biomaterialia, vol. 8:262-273 (2012).

Floden, Evan W. et al., "Biophysical characterization of ovine forestomach extracellular matrix biomaterials," J. Biomed, Mater, Res, B Appl, Biomater., vol. 96(1):67-75 (2011).

Freytes, D.O. et al., "Effect of storage upon material properties of lyophilized porcine extracellular matrix derived from the urinary bladder," J. Biomed. Mater Res. B Appl. Biomater., vol. 78(2):327-333 (2006).

(Continued)

*Primary Examiner* — Michael Wityshyn
*Assistant Examiner* — David Berke-Schlessel
(74) *Attorney, Agent, or Firm* — Nelson Mullins Riley & Scarborough LLP; Jane E. Remillard, Esq.

(57) ABSTRACT

The present invention pertains to the development of Extracellular Matrix (ECM) scaffolds derived from the forestomach of a ruminant. Such scaffolds are useful in many clinical and therapeutic applications, including wound repair, tissue regeneration, and breast reconstruction. In addition, the present invention features methods of isolating ECM scaffolds from mammalian organs, including but not limited to the ruminant forestomach. The invention further features laminated ECM scaffolds containing a polymer positioned between individual ECM sheets. The polymer may optionally contain bioactive molecules to enhance the functionality of the scaffold.

16 Claims, 18 Drawing Sheets

(56) References Cited

OTHER PUBLICATIONS

Freytes, D.O. et al., "Hydrated versus lyophilized forms of porcine extracellular matrix derived from the urinary bladder," J. Biomed. Mater Res. A, vol. 87(4):862-872 (2008).

Gouk, S.S. et al., "Alterations of human acellular tissue matrix by gamma irradiation: histology, biomechanical property, stability, in vitro cell repopulation, and remodeling," J. Biomed. Mater Res. B Appl. Biomater., vol. 84 (1):205-217 (2008).

Irvine, Sharleen M. et al., "Quantification of in vitro and in vivo angiogenesis stimulated by ovine forestomach matrix biomaterial," Biomaterials, vol. 32:6351-6361 (2011).

Lemer, M. et al., "Tissue strength analysis of autologous and cadaveric allografts for the pubovaginal sling," Neurourol. Urodyn., vol. 18(5):497-503 (1999).

Lindblad, W.J. et al., "How should one study wound healing," Wound Repair Regen., vol. 14(5):515 (2006).

Lindblad, W.J. et al., "Considerations for selecting the correct animal model for dermal wound-healing studies," J. Biomater. Sci. Polym. Ed., vol. 19(8):1087-1096 (2008).

Lun, Stan et al., "A functional extracellular matrix biomaterial derived from ovine forestomach," Biomaterials, vol. 31:4517-4529 (2010).

Morgan, Adam S. et al., "Biomechanical Properties of Materials Used in Static Facial Suspension," Arch. Facial Plast. Surg., vol. 6:308-310 (2004).

Sclafani, Anthony P. et al., "Biophysical and Microscopic Analysis of Homologous Dermal and Fascial Materials for Facial Aesthetic and Reconstructive Uses," Arch. Facial Plast. Surg., vol. 4:164-171 (2002).

Vural, E. et al., "Comparison of biomechanical properties of alloderm and enduragen as static facial sling biomaterials," Laryngoscope, vol. 116(3):394-396 (2006).

Zerris, V.A. et al., "Repair of the dura mater with proceessed collagen devices," J. Biomed. Mater Res. B Appl. Biomater., vol. 83(2):580-588 (2007).

New Zealand Office Action for Application No. 591353, 2 pages, dated Apr. 27, 2011.

International Preliminary Report on Patentability for Application No. PCT/NZ2009/000152, 15 pages, dated Jul. 16, 2010.

Supplementary European Search Report for Application No. 09803207.1, 11 pages, dated Jul. 25, 2012.

* cited by examiner

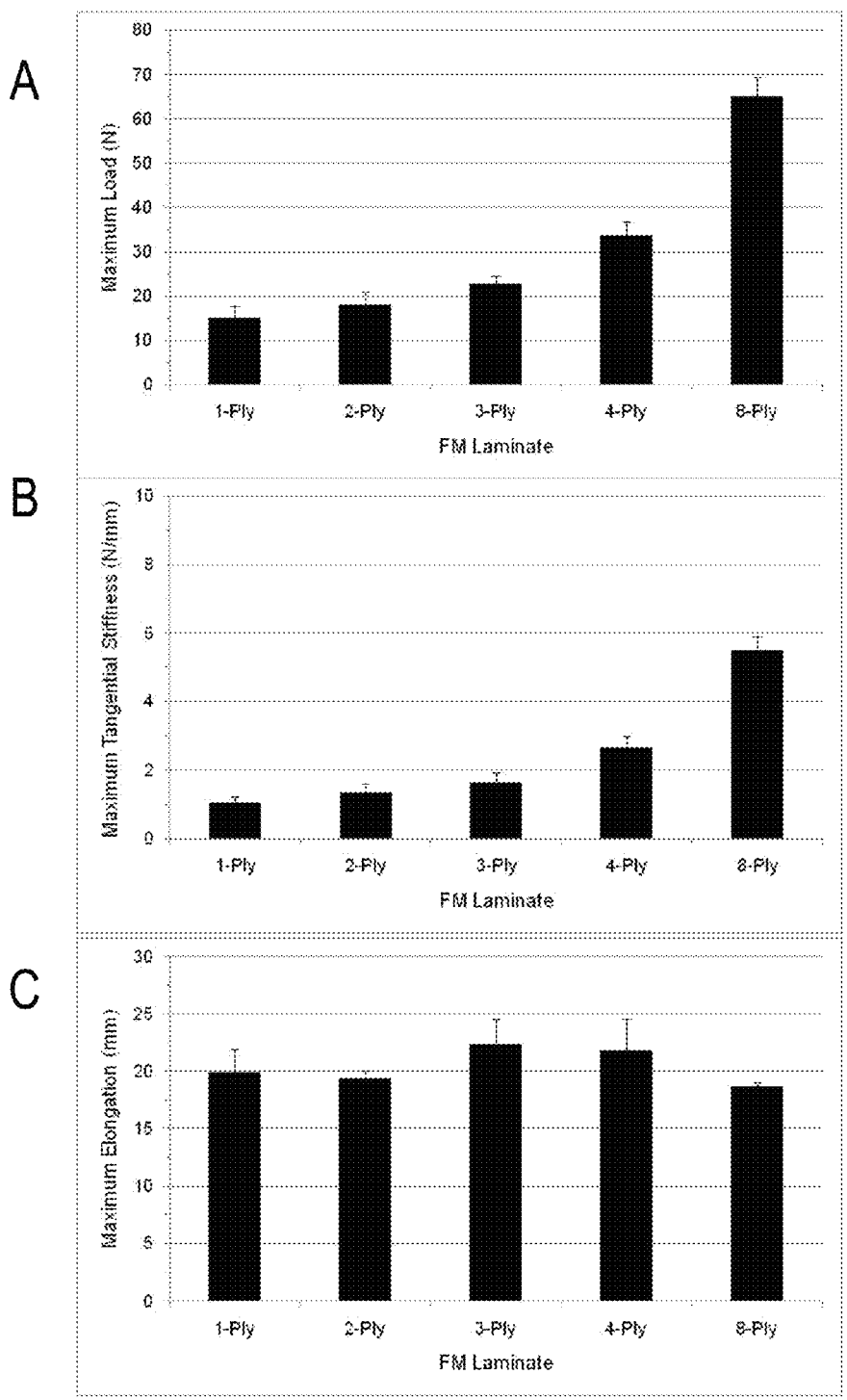
Fig. 13A-C

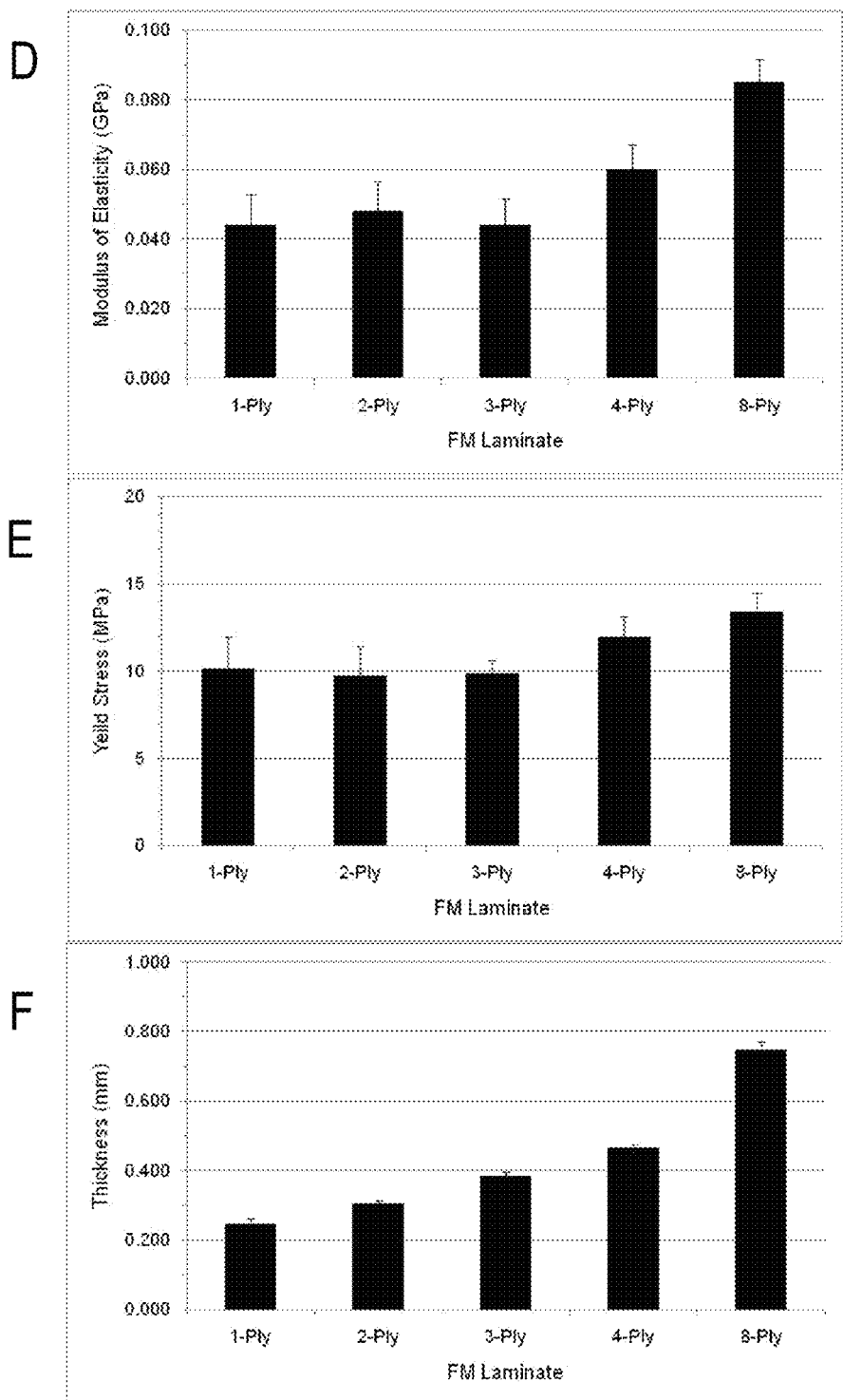
*Fig. 13D-F*

| | 1-Ply FM | | | | | 2-Ply FM | | | | | SIS | | | | |
|---|---|---|---|---|---|---|---|---|---|---|---|---|---|---|---|
| Pig Number | 100 | 101 | 102 | 103 | 104 | 100 | 101 | 102 | 103 | 104 | 100 | 101 | 102 | 103 | 104 |
| Day 3 | ▓ | ▓ | ▓ | ▓ | ▓ | ▓ | ▓ | ▓ | ▓ | ▓ | ▓ | ▓ | ▓ | ▓ | ▓ |
| Day 7 | ▓ | ▓ | ▓ | ▓ | ▓ | ▓ | ▓ | ▓ | ▓ | ▓ | ▓ | ▓ | ▓ | ▓ | ▓ |
| Day 14 | ▓ | ▓ | ▓ | ▓ | ▓ | ▓ | ▓ | ▓ | ▓ | ▓ | ▓ | ▓ | ▓ | ▓ | |
| Day 28 | | | ▓ | ▓ | | | | | | | ▓ | ▓ | ▓ | | ▓ |
| Day 42 | | | | | | | | | | | | | | | |

TISSUE SCAFFOLDS DERIVED FROM FORESTOMACH EXTRACELLULAR MATRIX

RELATED APPLICATIONS

This application is a divisional of U.S. patent application Ser. No. 12/512,835, filed Jul. 30, 2009 which claims the benefit of U.S. Provisional Application No. 61/137,367, filed on Jul. 30, 2008, and to U.S. Provisional Application No. 61/172,671, filed on Apr. 24, 2009. The entire contents of the foregoing applications are incorporated herein by reference.

BACKGROUND OF THE INVENTION

Extracellular matrix (ECM) has an important role in providing the optimal chemical and structural environment for tissue growth and regeneration. ECM scaffolds used for tissue regeneration are traditionally prepared from decellularised human and animal dermis isolated from various organs, and from a variety of animal submucosal and basement membrane sources. These scaffolds promote tissue regeneration and are well-tolerated immunologically. Common submucosal tissue graft compositions are derived from the small intestine, the urinary bladder, and the simple glandular stomach (see, for example, U.S. Pat. No. 4,902,508, U.S. Pat. No. 5,554,389, and U.S. Pat. No. 6,099,567, the entire contents of which are incorporated herein by reference).

Despite advances in the production and use of ECM scaffolds, the ideal scaffold composition has not been identified. The ideal scaffold is non-allergenic, non-carcinogenic, mechanically stable under continuous stress, adequately porous to allow capillarisation, able to encourage and direct appropriate cellular and vascular in-growth, of similar compliance to that of the host tissue, resistant to infection, non-thrombogenic, inexpensive, and able to become a fully functional analog of the original tissue. An ECM scaffold possessing these properties would be useful in a variety of clinical applications, including wound repair and soft tissue regeneration.

SUMMARY OF THE INVENTION

The present invention provides extracellular matrix (ECM) scaffolds derived from the forestomach of a ruminant, also referred to herein as "Forestomach Matrix" (FM) scaffolds. The FM scaffolds of the invention provide a number of advantages over prior tissue scaffolds, and are useful in a variety of clinical and therapeutic applications, including wound repair and tissue regeneration. In addition, the present invention provides improved methods of producing ECM scaffolds from mammalian organs, including but not limited to the ruminant forestomach. In particular embodiments, FM scaffolds of the invention may be derived from a ruminant belonging to the genus *Capra, Bos, Cervus* or *Ovis*, e.g., *Capra aegagrus hircus, Bos taurus*, or *Ovis aries*.

Accordingly, in a first aspect, the invention features a tissue scaffold (an FM scaffold) comprising the ECM of the propria-submucosa of the forestomach of a ruminant. In a particular embodiment, the propria-submucosa is from the rumen, the reticulum, or the omasum of the forestomach. These tissue scaffolds typically have a contoured luminal surface. The ECM tissue scaffolds of the invention may additionally contain decellularised tissue, including portions of the epithelium, basement membrane, or tunica muscularis, and combinations thereof. The tissue scaffolds may also comprise one or more fibrillar proteins, including but not limited to collagen I, collagen III, or elastin, and combinations thereof. In other embodiments, the tissue scaffolds can comprise one or more growth factors, including but not limited to FGF-2, TGFb1, TGFb2, or VEGF, and combinations thereof. In still other embodiments, the tissue scaffolds can comprise one or more glycosaminoglycans, including but not limited to hyaluronic acid and heparan sulfate, and combinations thereof. In another embodiment, the tissue scaffolds can comprise one or more adhesive proteins, including but not limited to fibronectin, collagen IV, or laminin, and combinations thereof.

FM scaffolds of the present invention can be formatted in a variety of manners, such as a single sheet, or as a laminated sheet containing multiple sheets of FM. In certain embodiments, the FM scaffolds comprise 2-15 laminated sheets. Such laminated sheets can be held together by stitches or sutures. Alternatively, the laminated sheets can be held together by a polymer positioned in between one or more sheets. In one embodiment, the laminated sheets are attached by stitches or sutures and additionally contain a polymer positioned between one or more sheets. In another embodiment, the laminated tissue scaffold comprises a polymer positioned between each of the laminated sheets. The polymer may be interspersed between the sheets, or may be evenly distributed as a polymer layer. Any suitable polymer may be used in the FM scaffolds of the invention, including but not limited to collagen, chitosan, alginate, polyvinyl alcohol, carboxymethyl cellulose, hydroxypropyl cellulose, and combinations thereof.

In a particular embodiment, the polymer further comprises a bioactive molecule, for example, a small molecule or a peptide. The bioactive molecule may be non-covalently incorporated into the polymer, for example, as a suspension, encapsulated as particles, microparticles, or colloids, or as a mixture thereof. The bioactive molecule may also be covalently incorporated into the polymer, using any suitable chemistry for attachment of the bioactive molecule to the polymer. The bioactive molecule can be any therapeutically desirable molecule, such as a growth factor, an anti-microbial, an analgesic, a hemostatic, a pro-angiogenic agent, or an anti-angiogenic agent. In exemplary embodiments, the polymer comprises one or more of FGF2, NGF, doxycycline, amoxicillin, and poly-L-lysine.

In another particular embodiment, the FM scaffolds have a width of at least 10 cm. For example, the scaffold can have a width of at least 10 cm and a length of at least 10 cm. Accordingly, certain FM scaffolds can have a surface area of more than 100 $cm^2$, e.g., 400 $cm^2$. In one embodiment the single or laminated sheets of an FM scaffold are perforated. In another embodiment the FM is fluidized, or micronized.

FM scaffolds of the invention generally have a biaxial strength greater than scaffolds obtained from other gastrointestinal or urogenital sources. Accordingly, in a particular embodiment, the FM scaffolds have an average biaxial strength of at least 80 N or more.

Tissue scaffolds of the invention can be used in multiple applications, including but not limited to covering a tissue deficit and reinforcing soft tissue. In a particular embodiment, the tissue deficit or the soft tissue has width of at least 10 cm. In another embodiment, the tissue deficit or the soft tissue has a width of at least 10 cm and a length of at least 10 cm. In still another embodiment, the tissue deficit or the soft tissue has a surface area of at least 100 $cm^2$.

Accordingly, in another aspect, the invention features a method for inducing repair of a damaged tissue, comprising contacting the damaged tissue with an FM scaffold of the invention, e.g., one that comprises the ECM of the propria-submucosa of a ruminant. The invention further features a method for stimulating soft tissue regeneration, comprising contacting the soft tissue with an FM scaffold of the invention.

When an FM scaffold is placed in contact with a tissue, the FM scaffold can increase proliferation of cells located near the scaffold. In addition, the FM scaffold can promote vascularization within a tissue to which it adheres. Accordingly, in another aspect, the invention provides a method of stimulating proliferation of cells in a tissue, comprising contacting the tissue with an FM scaffold such that cell proliferation is stimulated. The invention further provides a method of inducing vascularization of a tissue, comprising contacting the tissue with an FM scaffold such that vascularization occurs within the tissue.

In one aspect, the invention features an implantable tissue scaffold device for supporting breast tissue within a patient, wherein the device comprises extracellular matrix of the propria-submucosa of the forestomach of a ruminant. The breast tissue may comprise a breast prosthesis, i.e., a breast implant. The tissue scaffold device may be formatted as a laminated sheet comprising two or more layers of extracellular matrix. In a particular embodiment, the laminated sheet comprises 2-15 layers of extracellular matrix.

The tissue scaffold device may be flat, or it may have a concavity. In one embodiment, the layers of extracellular matrix of the device may be secured together by stitches or sutures. The extracellular matrix may be perforated, or it may be unperforated. In some embodiments, the device has a crescent shape. In other embodiments, the device has an elliptical shape.

In another aspect, the invention provides a method of supporting breast tissue within a patient, comprising positioning the foregoing tissue scaffold device within the patient in a supporting position relative to the breast tissue. In one embodiment, the breast tissue comprises a breast prosthesis. In another embodiment, the breast tissue comprises native tissue. In a particular embodiment, positioning the tissue scaffold comprises covering the lower and lateral sections of the breast tissue.

In another aspect, the invention provides a tissue scaffold comprising two or more sheets of extracellular matrix, laminated by a polymer positioned between the sheets. The scaffold may comprise extracellular matrix of the submucosa of a tissue selected from the group consisting of small intestine, stomach, bladder, pericardium, and dermis. In a particular embodiment, the extracellular matrix comprises collagen. The polymer may comprise collagen, chitosan, alginate, polyvinyl alcohol, carboxymethyl cellulose, hydroxypropyl cellulose, and combinations thereof.

In a particular embodiment of the foregoing aspect, the polymer further comprises a bioactive molecule. The bioactive molecule may be non-covalently or covalently linked to the polymer. In one embodiment, the bioactive molecule may be a small molecule or a polypeptide, e.g., a growth factor, an anti-microbial, an analgesic, a hemostatic, a pro-angiogenic agent, an anti-angiogenic agent, or combinations thereof. Exemplary bioactive molecules include FGF2, NGF, doxycycline, poly-L-lysine, and combinations thereof.

In yet another aspect, the present invention provides methods of generating ECM tissue scaffolds by separating and/or decellularising the layers within all or a portion of a tissue. The methods involve creating a transmural osmotic flow between two sides of the tissue, such that the layers within all or a portion of the tissue are separated and/or decellularised. The transmural osmotic flow can be directed from the luminal to the abluminal side of all or a portion of the tissue, or from the abluminal to the luminal side of all or a portion of the tissue. This can be achieved, for example, by separating the tissue between a hypertonic and a hypotonic solution, such that the transmural osmotic flow is directed from the hypotonic solution to the hypertonic solution. The method can further involve removing all or part of a tissue layer including epithelium, basement membrane, or tunica muscularis, and combinations thereof.

In a particular embodiment, the method of the invention involves encapsulating a first solution within an organ or tissue (or a portion thereof), and immersing the organ or tissue (or portion thereof) in a second solution which is hypertonic to the first solution. This method can further involve removing the organ or tissue from the second solution, and immersing the organ or tissue, or portion thereof, in a third solution which is also hypertonic to the first solution, in order to, for example, further decellularise the tissue.

In an alternative embodiment, the method comprises encapsulating a first solution within an organ or a tissue (or portion thereof), and immersing the organ or tissue (or portion thereof) in a second solution which is hypotonic to the first solution, optionally followed by immersing the organ or tissue, or portion thereof, in a third solution which is also hypotonic to the first solution.

The hypertonic and hypotonic solutions can include, for example, water and optionally at least one buffer, detergent or salt. The hypertonic solution contains a higher concentration of solute than the hypotonic solution. In a particular embodiment, the hypertonic solution comprises 4 M NaCl, and the hypotonic solution comprises 0.028% Triton X-200 and 0.1% EDTA. In another particular embodiment, the hypotonic solution comprises 0.1% SDS. In still another embodiment, the hypotonic solution comprises 0.028% Triton X-200, 0.1% EDTA, and 0.1% SDS.

The methods of the invention can be performed at low temperatures of, for example, 4° C. or less (e.g., between about 2° C. and about 4° C.). The methods of the invention can alternatively be performed at or near room temperature (e.g., between about 18° C. and about 24° C. The methods also allow tissue layers to be separated and decellularised in a shorter period of time than is possible using other methods. In particular embodiments, the tissue layers are separated and decellularised in 36 hours or less, more preferably in 24 hours or less. In other embodiments, the tissue layers are separated and decellularised in 6 hours or less (e.g., in 5 hours or less, 4 hours or less, or 3 hours or less).

The methods of the invention can be employed with any suitable tissue source or organ. In a particular embodiment, the tissue comprises a keratinized stratified squamous epithelium. In other particular embodiments, the tissue is derived from the forestomach of a ruminant, e.g., an animal belonging to the genus *Capra, Bos, Cervus* and *Ovis*. In still other embodiments, the tissue is derived from the rumen, the reticulum, or the omasum of the forestomach. Such tissues can optionally be distended to increase the transmural osmotic flow across the tissue layers, further facilitating separation and decellularisation.

BRIEF DESCRIPTION OF THE DRAWINGS

FIG. 13 presents a comparison of the strength of ovine FM single and multi-ply products. (A) Maximum load at failure (N); (B) Maximum tangential stiffness (N/mm); (C) Maximum elongation (mm); (D) Modulus of elasticity (Young's) (GPa); (E) Yield Stress (MPa); and (F) thickness. Maximum load at failure of single and multi-ply products was determined using an Instron 5800 series electromechanical tester. Various materials were cut to dog-bone shaped samples with a 0.6 cm width. Samples were clamped with a gauge length of 7.5 cm. and elongated at a rate of 25.4 mm/min until failure. Load (N) was recorded using a 500 N load cell. Stiffness was calculated from the slope of the load (N) versus elongation (mm) curve. The load versus elongation curve was transformed to a stress (N/m$^2$) versus strain curve, using a cross-sectional area of calculated from the thickness of the product. The slope of this latter curve was used to calculate the modulus of elasticity, or Young's modulus (GPa). Error bars represent the standard error of at least five samples.

DETAILED DESCRIPTION OF THE INVENTION

Figure 1A:
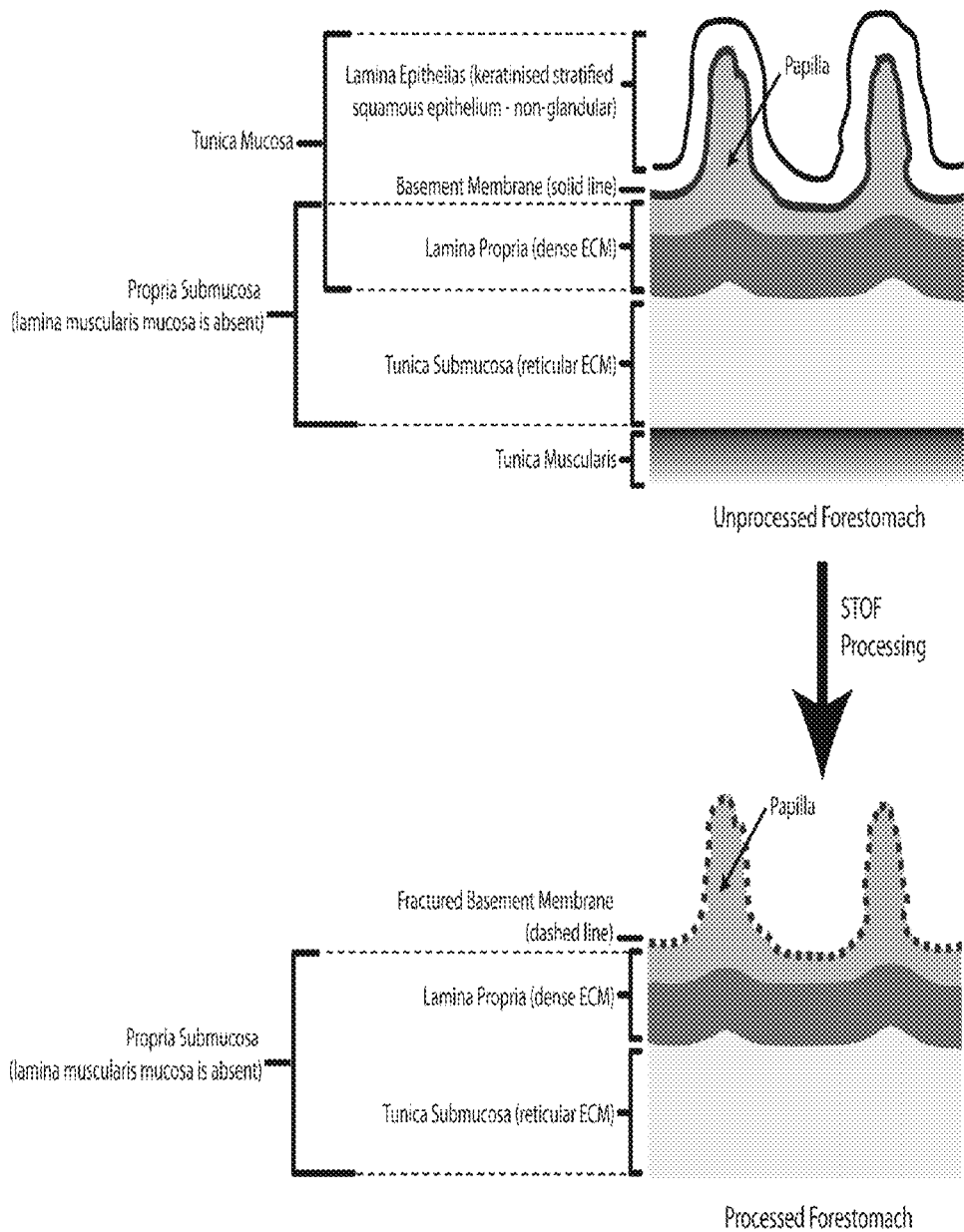
FIG. 1 is a schematic cross-section of (A) the forestomach wall, and (B) the glandular stomach wall, both in an unprocessed state and after STOF processing.

The present invention relates to the development of Extracellular Matrix (ECM) scaffolds derived from the propria-submucosa of the forestomach of a ruminant, referred to herein as 'Forestomach Matrix' (FM). FM scaffolds possess distinct characteristics which differ from ECM scaffolds derived from other organs, including the glandular stomach. These characteristics make FM scaffolds particularly well-suited for clinical applications involving tissue regeneration and repair. The present invention further relates to improved methods for generating ECM scaffolds from mammalian organs, including but not limited to the forestomach.

I. DEFINITIONS

So that the invention may be more readily understood, certain terms are first defined.

The term "Forestomach Matrix" (abbreviated FM), as used herein, refers to an ECM scaffold containing the propria-submucosa of the forestomach of a ruminant.

The term "propria-submucosa," as used herein, refers to the tissue structure formed by the blending of the lamina propria and submucosa in the ruminant forestomach.

The term "lamina propria," as used herein, refers to the luminal portion of the propria-submucosa, which includes a dense layer of extracellular matrix.

The term "ruminant," as used herein, refers to a mammal having a stomach with four chambers. These include a forestomach, comprised of a rumen, a reticulum and an omasum, and a fourth chamber known as an abomasum. Non-limiting examples of ruminants include mammals belonging to the genus *Capra, Bos, Cervus*, and *Ovis*.

The term "derived from," as used herein, refers to the tissue source or origin of an ECM. ECMs can be derived in whole or in part from tissues, such that they retain at least one component of the tissue, such as the propria-submucosa.

The term "propria-submucosa," as used herein, refers to a portion of the forestomach wall of a ruminant which consists of the lamina propria and the tunica submucosa.

The term "Sealed Transmural Osmotic Flow" (STOF), as used herein, refers to a method of decellularising and/or separating the layers of tissue or organ in which a transmural osmotic flow is established across all or part of the wall of the tissue or organ.

The term "hypertonic," as used herein, refers to a solution having a higher concentration of solute relative to another solution.

The term "hypotonic," as used herein, refers to a solution having a lower concentration of solute relative to another solution.

The term "delaminated," as used herein, refers to the separation of layers within a tissue or organ.

The term "decellularised," as used herein, refers to the removal of cells and their related debris from a portion of a tissue or organ, for example, from the ECM.

The term "breast reconstruction," as used herein, refers to any procedure intended to alter the size, shape, position or appearance of a breast mound in a patient. Such procedures include, but are not limited to, breast augmentation, mastopexy (i.e., breast lift), and reconstruction post-mastectomy.

Various aspects of the invention are described in further detail in the following subsections. Unless otherwise defined, all technical and scientific terms used herein have the same meaning as is commonly understood by one of ordinary skill in the art to which this invention belongs. In case of conflict, the present specification, including definitions, will control. Although methods and materials similar or equivalent to those described herein can be used in the practice of the invention, examples of suitable methods and materials are described below. The materials, methods, and examples described herein are illustrative only and are not intended to be limiting. All publications, patent applications, patents, and other references mentioned herein are incorporated by reference in their entirety.

II. ANATOMY OF THE FORESTOMACH OF A RUMINANT

Ruminants (e.g., cattle, sheep and goats) have compound stomachs which differ from the simple stomach of other mammals in that the compound stomach is substantially larger and is divided into four sections: the rumen, reticulum, omasum, and abomasum. Each of these sections has a distinct physical and histological structure. Collectively the rumen, reticulum, and omasum are known as the forestomach (proventriculus). The rumen and reticulum are intimately related in structure and function and are often referred to as rumenoreticulum. Only the last chamber of the compound stomach, the abomasum, is structurally analogous to the simple glandular stomach. The anatomical differences between the forestomach and the simple glandular stomach reflect their distinct functional roles. The primary functions of the forestomach are storage, fermentation and absorption, while the simple glandular stomach performs secretory and digestive functions.

Figure 1B:
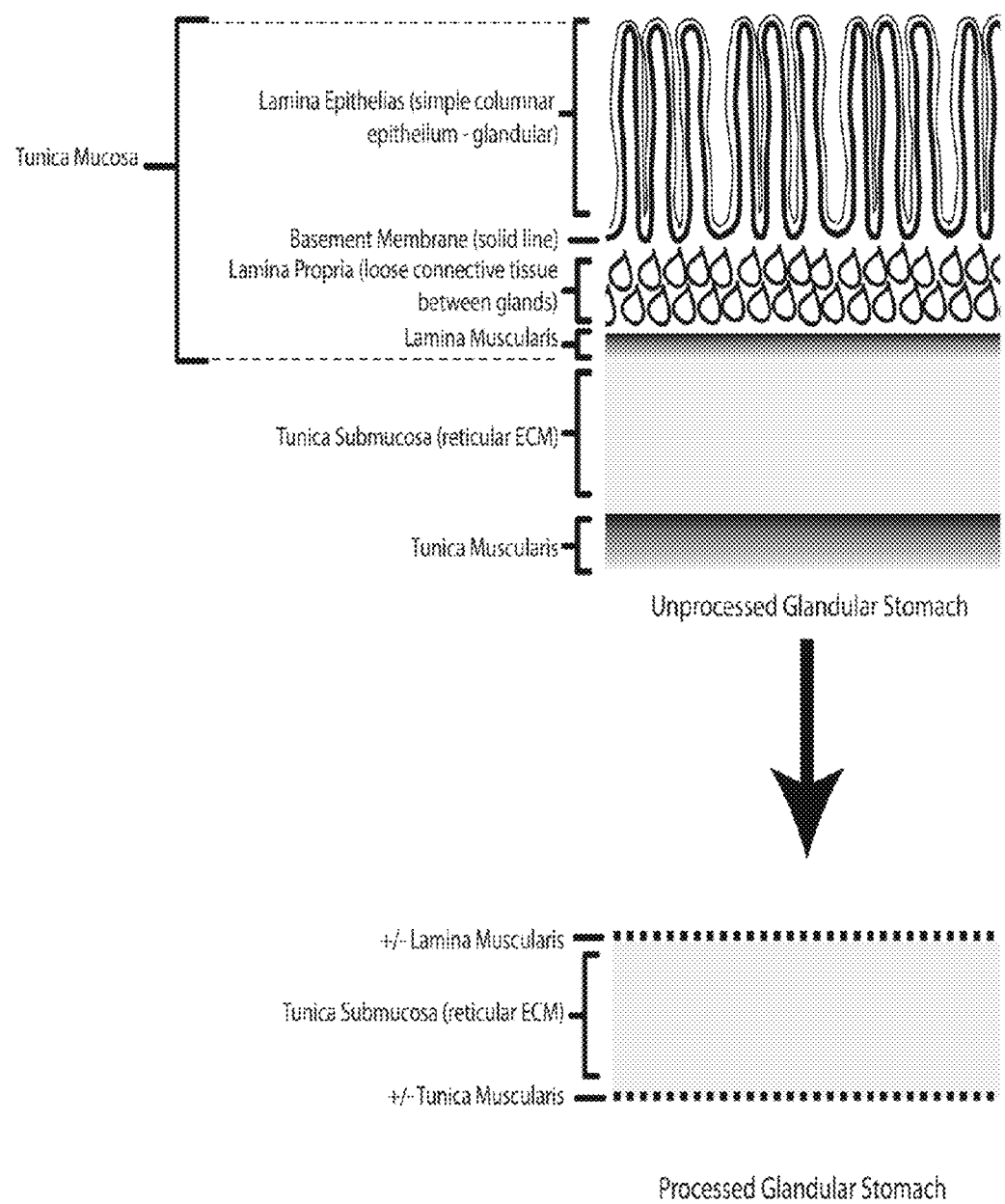

Consequently, the forestomach has gross anatomical and histological features that are quite distinct from those of the glandular stomach. Anatomical characteristics of the forestomach are illustrated in FIG. 1A, and those of the glandular stomach are illustrated in FIG. 1B. Importantly, the forestomach does not contain a glandular mucosa, but is instead comprised of a non-glandular keratinized stratified squamous epithelium, which consists of the stratum corneum, stratum granulosum, stratum spinosum and stratum basale, and appears in many respects analogous to the structure of the skin. The epithelium is located on the luminal side of the forestomach, and is separated from the underlying propria-submucosa by a basement membrane. The abluminal side of the forestomach contains a muscle layer known as the tunica muscularis.

Stomach submucosa compositions described previously are derived from the wall of the glandular stomach, which contains the following layers: the tunica mucosa (including an epithelium layer, a lamina propria layer consisting of reticular or fine areolar tissue, and a glandular layer), the tunica submucosa layer (composed of areolar tissue and lacking glands), the tunica muscularis layer (composed of three layers of muscle), and the serosa (a layer of mesothelium outside the loose connective tissue which invests the muscle layers). The presence of the glandular layer within the stomach wall is characteristic of the glandular, gastric or simple stomach of monogastric mammals. Only the last chamber of the complex stomach of ruminants, the abomasum, contains this glandular layer. Additional characteristics of the forestomach and the glandular stomach are described in Table 1.

TABLE 1

Features of the forestomach and the glandular stomach

| Feature | Forestomach | Glandular stomach |
|---|---|---|
| Epithelium | Keratinised stratified squamous | Simple Columnar |
| Glands | No | Yes |
| Lamina muscularis mucosa present | No | Yes |
| lamina propria merges into submucosa creating a propria-submucosa | Yes | No |
| Lamina propria | Dense | Loose |
| lamina propria contains Collagen IV and Laminin | Yes | No |
| Papilla on surface | Yes | No |
| Lamina propria retained with the propria-submucosa when epithelium is physically delaminated | Yes, dense lamina propria resists physical delamination | No, loose lamina propria and glands do not resist physical delamination |
| Dense lamina propria on the luminal side of the propria-submucosa | Yes | No |
| Contoured surface when epithelium delaminated | Yes, due to the ECM within the papilla | No |

Two unique features of the forestomach relative to the glandular stomach are that the lamina propria of the forestomach is much denser and does not include glands or a glandular layer. In addition, the lamina muscularis mucosa, a fine muscle layer in the basal region of the tunica mucosa layer of the glandular stomach, is absent from the rumen and most of the reticulum. In the absence of the lamina muscularis, the lamina propria blends with the submucosa to form a layer which is collectively referred to as the propria-submucosa. Also unique to the forestomach is an unusually thick and dense band of ECM within the lamina propria which runs parallel to the epithelial surface. This band of tissue contains collagen IV and laminin, which play a critical role in cell growth, differentiation, and migration during tissue development and reconstruction. Beneath this band of tissue the ECM has a more typical open reticular pattern. Included in the forestomach ECM is the glycosaminoglycan heparan sulfate, an important co-factor that modulates the bioactivity of the growth factor FGF2. As referenced in U.S. Pat. No. 6,099,567, heparan sulfate is not present in glandular stomach submucosa. This is an important differentiation between the two ECMs.

Forestomach tissue also includes surface protrusions known as papillae in the rumen, reticular crests in the reticulum, and lamellae in the omasum. The propria-submucosa extends into these protrusions.

III. TISSUE SCAFFOLDS DERIVED FROM THE FORESTOMACH

According to the present invention, ECM scaffolds can be derived from the rumen, the reticulum or the omasum of the forestomach. Such ECM scaffolds (referred to herein as "Forestomach Matrix" or FM) are characterized in that they contain the lamina propria and submucosa (propria-submucosa) layers of the forestomach wall. In a particular embodiment of the invention, FM scaffolds are derived from the rumen or from individual laminae within the omasum. In addition to propria-submucosa, FM scaffolds may optionally include intact or partial layers of decellularised epithelium, basement membrane, or tunica muscularis (see FIG. 1A).

As a result of the unique structure and function of the forestomach, ECM tissue scaffolds of the invention derived from the forestomach have different biochemical, structural and physical properties relative to previously described scaffolds isolated from glandular stomach, intestine, and bladder. In particular, FM includes a dense band of ECM within the lamina propria. In addition, FM optionally includes an intact or fractured basement membrane. In contrast, a scaffold derived from the glandular stomach submucosa or small intestinal submucosa will include little if any of the lamina propria, because the lamina propria is located mainly between the glands of the mucosa, and is consequently removed as the mucosa is delaminated. Importantly, histology shows that the lamina propria is unusually dense, whereas the abluminal side of the FM scaffold is structured as an open reticular matrix. These differences serve an important role in epithelial regeneration, as the dense side acts as a barrier to cell migration, while the less dense side does not present a barrier and therefore allows cell invasion. This structure makes the FM well suited for encouraging epithelial regeneration on the dense luminal side of the matrix, and fibroblast invasion on the less dense abluminal side of the matrix, when used as a medical device for tissue regeneration. In contrast, submucosal tissue grafts derived from the glandular stomach and the urinary bladder have a uniform density.

The dense layer of ECM from the lamina propria contributes to the increased thickness and strength of FM scaffolds compared to those derived from other organs. A comparison of the thickness and burst strength of compositions derived from the forestomach and those derived from other organs are provided in Examples 11 and 12. The large surface area of the forestomach and the increased thickness and strength of scaffolds derived from the forestomach allows the isolation of larger ECM scaffolds from the forestomach than is possible from other organs. For example, ECM scaffolds of the invention can have a width as large as 5 cm (e.g., 0.5 cm, 1 cm, 2 cm, 3 cm, 4 cm, or 5 cm), more preferably at least 6 cm, 7 cm, 8 cm, or 9 cm, and most preferably at least 10 cm or more. In addition, ECM scaffolds of the invention can have a length as large as 5 cm (e.g., 0.5 cm, 1 cm, 2 cm, 3 cm, 4 cm, or 5 cm), more preferably at least 6 cm, 7 cm, 8 cm, or 9 cm, and most preferably at least 10 cm or more. Accordingly, in a particular embodiment, FM scaffolds of the invention can have a width and a length of 10 cm or more, a size much larger than ECM scaffolds derived from other organs. Exemplary FM scaffolds have a surface area of at least 100 $cm^2$, 200 $cm^2$, 300 $cm^2$, 400 $cm^2$, 500 $cm^2$, 600 $cm^2$, 700 $cm^2$, 800 $cm^2$, 900 $cm^2$, or 1000 $cm^2$ or more. In a particular embodiment, the FM scaffold has a surface area of approximately 400 $cm^2$.

Unlike scaffolds obtained from the glandular stomach, ECM scaffolds derived from the forestomach (i.e., FM scaffolds) can include collagen IV and laminin from the basement membrane on the luminal surface. Surprisingly, these proteins are also present within the dense band of the lamina propria, providing important substrates for epithelial cell adhesion and growth. Glandular stomach scaffolds do not typically include the epithelium or basement membrane, or portions thereof, because these layers are fragile and do not withstand physical delamination (see FIG. 1B). A glandular submucosal scaffold may include remnants of the lamina muscularis mucosa on the luminal side and tunica muscularis on the abluminal side.

FM scaffolds have a contoured luminal surface, analogous to the rete ridges of the dermis. In contrast, scaffolds delaminated from small intestine, urinary bladder and glandular stomach submucosa have a relatively smooth luminal surface. The contoured luminal surface of the FM provides a complex topology which favors epithelial regeneration. This topology is not present in ECM scaffolds derived from small intestinal submucosa, glandular stomach submucosa or urinary bladder submucosa.

FM scaffolds of the invention contain important regulators of wound repair, including but not limited to the growth factors FGF-2, TGFb1, TGFb2, and VEGF, and the glycosaminoglycans hyaluronic acid and heparan sulfate. FGF2 plays an important role in wound healing by signaling cell migration and differentiation required for the formation of new tissue and vasculature. Heparan sulphate is an important co-factor that modulates bioactivity of FGF2 by acting on FGF2 receptors. Heparan sulphate is required for FGF2 activity and increases the stability of FGF2. Importantly, FGF2 and heparan sulphate are not present on stomach submucosa. FM additionally contains fibrillar proteins including collagen I, collagen III and elastin, as well as adhesive proteins including fibronectin, collagen IV and laminin. These proteins, in particular collagen and elastin, contribute to the high tensile strength and resilience of FM scaffolds. A detailed quantification of the molecular composition of FM scaffold is provided in Example 7.

In particular embodiments, FM scaffolds can be laminated together to form multi-layer sheets. For example, the laminated FM may comprise 2 or more sheets of FM scaffold (e.g., between 2 and 30 sheets of FM scaffold, e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30 or more sheets). In a particular embodiment, laminated FM comprises between 2 and 15 sheets of FM scaffold, e.g., 2 to 10 sheets, 2 to 8 sheets, 2 to 6 sheets, or 2 to 4 sheets of FM scaffold. The sheets of FM scaffold can be laminated together using any suitable technique known in the art. In addition, lamination can be achieved using a polymer, as described below. Lamination can be achieved with or without sewing with resorbable or non-absorbable suture material or equivalent.

The strength and physical characteristics of the FM scaffold translate into improved handling characteristics relative to scaffolds derived from thinner and weaker ECM sources. As FM scaffolds are physically more robust than ECM scaffolds isolated from other sources, e.g., glandular stomach, they provide greater ease of handling, and are more resistant to handling deformations. This has important implications in clinical practice where the handling of scaffolds is necessary prior to and during surgical procedures.

FM scaffolds can be unperforated, or they can be perforated. Perforations may be introduced into the FM scaffold using any suitable method, including manual drilling or laser drilling. The pore size can vary between about 10 to about 500 microns (e.g., about 10, 15, 20, 25, 30, 35, 40, 45, 50, 60, 70, 80, 90, 100, 125, 150, 175, 200, 225, 250, 275, 300, 325, 350, 375, 400, 425, 450, 475, or about 500 microns). Perforations may be introduced at any time during the production of FM scaffolds, but is preferably done prior to sterilization. The perforations may pass completely through the FM scaffold, or may penetrate only partially through the FM scaffold. In a laminated FM scaffold comprising multiple layers of FM sheets, the perforations may pass completely through all layers of the scaffold, or may pass through only some layers and, accordingly, penetrate only partially through the scaffold. Perforation permits cells to more easily infiltrate the scaffold, allowing for more rapid tissue ingrowth and remodeling of the scaffold.

The FM scaffolds of the invention are unique in that they combine improved handling characteristics, are available in large formats and include novel combinations of biochemical constituents.

While suitable methods of isolating ECM scaffolds from the forestomach of a ruminant are described herein, the invention is intended to encompass ECM scaffolds that are isolated from the forestomach of a ruminant by any means, including but not limited to the STOF method set forth below.

IV. LAMINATED TISSUE SCAFFOLDS

ECM scaffolds can be joined together to form a multi-ply laminated sheet. Lamination of ECM scaffolds increases the strength of the scaffold, making laminated ECM compositions particularly suitable for applications where the scaffold is required to be load bearing and/or to retain sutures or staples. Sheets may be joined together in several orientations. For example, two or more sheets may be stacked in the same orientation with respect to one another, i.e., such that the luminal surface of the matrix of one sheet contacts the abluminal surface of the matrix of an adjacent sheet. In an alternative embodiment, two or more sheets may be stacked in the opposite orientation with respect to one another, i.e., such that the luminal surface of the matrix of one sheet contacts the luminal surface of the matrix of an adjacent sheet, or such that the abluminal surface of the matrix of one sheet contacts the abluminal surface of the matrix of an adjacent sheet. Laminated FM scaffolds may be formed by bonding two or more layers of FM scaffold together using a number of techniques, including, but not limited to, a polymeric adhesive layer, sewing, or simply dehydrating contacting FM layers.

A. Laminated Tissue Scaffolds Containing Adhesive Polymers

Conventional methods of laminating ECM scaffolds to form multi-ply sheets involve the use of chemical agents to crosslink the ECM scaffolds directly to each other. By acting directly on the ECM scaffold, such agents modify the scaffold and, consequently, alter the scaffold's biological properties. The present invention overcomes this limitation by providing methods of forming laminated ECM scaffolds (e.g., FM scaffolds) without chemical modification of the scaffold itself. One such method involves distributing a polymer between one or more layers of ECM scaffold. The polymer serves as an adhesive, joining together alternating layers of ECM scaffold into a multi-ply composition. The polymer can also be applied to the outer surface(s) of an ECM scaffold. Importantly, the use of a polymer to bond a stack of ECM scaffolds negates the need for chemical crosslinking or other covalent modifications of the ECM to generate a laminated composition. Thus, the biological properties of the original ECM scaffold are retained in the laminated scaffolds.

The methods of using polymers to generate laminated ECM compositions as described herein are applicable to laminating together multiple layers of FM scaffold, or multiple layers of other ECM scaffolds known in the art, for example, ECM compositions derived from simple glandular stomach, small intestinal submucosa, bladder submucosa, or dermal ECM. In certain embodiments, a polymer can be used to form laminated sheets of Alloderm®, Strattice®, or Surgisis®, or combinations thereof. Polymers can also be used to form a laminated composition in which layers of FM are laminated to other ECM scaffolds, e.g., scaffolds derived from glandular stomach, small intestinal submucosa, bladder submucosa, pericardial or dermal ECM, e.g., Alloderm®, Strattice®, or Surgisis®.

In one embodiment, laminated ECM sheets (e.g., FM sheets) are formed by distributing a polymer between two or more alternating layers of ECM scaffold (e.g., FM scaffold). The polymer may be distributed intermittently across the ECM scaffold, or it may be present as a continuous layer. A polymer layer can be applied as intact films or sheets, or as solutions or gels. The polymer has the effect of bonding together two successive sheets of ECM. In a preferred embodiment, the polymer forms a continuous and intact layer within the laminate sandwich. The polymer can additionally or alternatively be applied to the outer surface of a laminated ECM scaffold. A range of suitable polymers including collagen, chitosan, alginate, polyvinyl alcohol, carboxymethyl cellulose or hydroxypropyl cellulose, or combinations thereof can be used to laminate successive sheets of ECM scaffold. The polymers can be applied as films, sheets, solutions, suspensions or gels to freeze-dried sheets of ECM, then dehydrated to yield laminated ECM sheets. Alternatively, the polymers can be applied as solutions, suspensions, gels or dry films to wet ECM sheets then dehydrated to yield laminated ECM. Other suitable polymers include, but are not limited to, the poly-glycolic acid (PGA), poly-lactic acid (PLA), Polylactic co-lactic acid (PLLA) and poly(lactic acid)-poly(glycolic acid) (PLGA) polymers described in any of U.S. Patent Application Nos. 2002/0119180 or 2003/0031696, or U.S. Pat. Nos. 6,281,256, 6,472,210, 5,885,829, 5,366,734; 5,366,733; 5,366,508; 5,360,610; 5,350,580; 5,324,520; 5,324,519; 5,324,307; 5,320,624; 5,308,623; 5,288,496; 5,281,419; 5,278,202; 5,278,201; 5,271,961; 5,268,178; 5,250,584; 5,227,157; 5,192,741; 5,185,152; 5,171,217; 5,143,730; 5,133,755; 5,108,755; 5,084,051; 5,080,665; 5,077,049; 5,051,272; 5,011,692; 5,007,939; 5,004,602; 4,961,707; 4,938,763; 4,916,193; 4,898,734; 4,898,186; 4,889,119; 4,844,854; 4,839,130; 4,818,542; 4,744,365; 4,741,337; 4,623,588; 4,578,384; 4,568,559; 4,563,489; 4,539,981; 4,530,449; 4,384,975; 4,300,565; 4,279,249; 4,243,775; 4,181,983; 4,166,800; 4,137,921, the contents of which are incorporated herein by reference in their entirety.

As will be appreciated by the skilled artisan, the polymeric layer contributes to the overall performance characteristics of the laminated scaffold. Accordingly, different strength and handling characteristics of the laminate can be produced by altering the nature of the polymer layer. In addition, changes in the composition of the polymer layer can be used to alter the hydration rate of the laminate and its proteolytic stability. For example, use of a relatively hydrophobic polymer results in a decreased rate of hydration of the laminate, relative to a laminate created using a hydrophilic polymer. Non-natural and synthetic polymers (e.g., poly-vinyl alcohol) would be expected to have increased enzymatic stability relative to naturally occurring polymers, (e.g. poly-saccharide).

By distributing a polymer between successive layers of ECM scaffold, laminated compositions comprising 2 or more sheets of ECM scaffold (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or more sheets of ECM scaffold) may be generated. In an exemplary embodiment, the ECM scaffold is an FM scaffold.

In one embodiment, a gel of collagen prepared from FM may be used as the polymer to laminate together two or more layers of FM scaffold. This gel retains the biochemical qualities of the parent FM scaffold and undergoes remodeling when used, for example, as part of a laminated FM scaffold for tissue regeneration.

B. Laminated Tissue Scaffolds Formed Using Stitches or Sutures

Laminated ECM sheets (e.g., laminated FM sheets) can alternatively be formed by sewing together multiple layers of ECM. The physical properties of FM (size, thickness, strength, etc.) enable sheets to be sewn or sutured together to form laminates for subsequent use. Laminates can be sewn together with or without a polymer layer situated between individual FM sheets.

Sewing provides another means of changing the performance characteristics of the laminated scaffolds. Sewing can also assist creating devices from one or more pieces of single or laminated FM sheets that have a three-dimension architecture which is useful for a specific anatomical site. Sewing helps to retain the three-dimensional form of the laminate following rehydration and during handling.

Sheets of FM scaffold can be sewn using any suitable thread, including but not limited to absorbable suture (e.g., polyglecaprone 25 (Monocryl), polydioxanone (PDS), polyglactin-910 (Vicryl), polyglycolic acid (Dexon)), non-absorbable suture (e.g., nylon (Ethilon), polypropylene (Prolene), cotton thread, or silk thread. Thread can be of various thickness or gauge depending on the required strength characteristics, (e.g., 6-0, 5-0 or 4-0 suture), and can be sewn using a variety of stitch lengths (e.g., 2 mm, 4 mm, or 6 mm) and patterns (e.g., straight stitch, running stitch, zig-zag stitch, overlock stitch or lock stitch).

C. Laminated Tissue Scaffolds Containing Bioactive Molecules

As described above, the invention relates in part to laminated ECM scaffolds (e.g., FM scaffolds) that include a polymer situated between individual ECM sheets. This polymer helps to bind together adjacent sheets of ECM scaffold. The composition of the polymer can be modified in order to alter the properties of the laminated ECM scaffold, including the effect the scaffold imparts on a tissue or organ. In a particular embodiment, the polymer can be used as a vehicle for delivery of bioactive molecules to a tissue or organ, allowing the bioactive molecules to be released at the site of contact. Tissue scaffolds containing bioactive molecules can be used, for example, to promote the rate and quality of tissue regeneration, and to prevent or treat acute or chronic infection.

Any desirable bioactive molecule can be incorporated into the polymer. Suitable molecules include, for example, small molecules, peptides or proteins, or mixtures thereof. In some embodiments, two or more (e.g., 2, 3, 4, 5, 6, 7, 8, 9, 10 or more) distinct bioactive molecules are incorporated into the polymer. Bioactive molecules can be non-covalently incorporated into the polymer either as suspensions, encapsulated as particles, microparticles and/or colloids, or as a mixture thereof. Bioactive molecules can also be covalently incorporated into the polymer using appropriate chemistries to link the bioactive molecule to the polymer. The polymer containing one or more bioactive molecules can be distributed between one or more ECM sheets of a laminated ECM scaffold (e.g., an FM scaffold), and/or may be applied to the outer surface of the scaffold. In a particular embodiment, a polymer containing a first bioactive molecule is distributed between some layers of a laminated ECM scaffold, and a polymer containing a second bioactive molecule is distributed between other layers of a laminated ECM scaffold. Suitable bioactive molecules include, but are not limited to, anti-microbials, analgesics, growth factors, hemostatics, pro- and anti-angiogenic agents, and combinations thereof. In particular embodiments, bioactive molecules incorporated into a polymer layer of a laminated ECM scaffold include FGF2, NGF, doxycycline, poly-L-lysine, and combinations thereof. In another particular embodiment, the polymer layer contains an anti-microbial agent and a growth factor. Importantly, as shown herein, by functionalizing the polymer layer of an ECM scaffold laminate with a bioactive molecule, the inherent biological properties of the ECM scaffold are not altered, in contrast with conventional methods in which additional molecules are incorporated into ECM scaffolds by attachment to the ECM directly.

Bioactive laminated ECM scaffolds (e.g., FM scaffolds) in which the bioactive agent is incorporated in an adhesive polymer (e.g., in a polymer layer) situated between successive layers of ECM have several critical advantages over alternative compositions in which a bioactive agent is conjugated directly to the ECM. Firstly, incorporation of the bioactive agent into a polymer or polymer layer does not change the inherent composition of the ECM scaffold, as it does not require covalent or chemical modification of the scaffold to achieve lamination or loading with the bioactive agent. Secondly, the use of a preformulated bioactive polymer layer as a vehicle for delivery of a bioactive agent allows greater control and consistency in the uniformity of dosing of the bioactive molecule.

IV. USES OF FORESTOMACH MATRIX COMPOSITIONS

Forestomach matrix scaffolds are well suited to a wide range of tissue regeneration applications. They can be used to cover tissue deficits such as wounds, and to reinforce and/or repair soft tissue. They can be used as single or laminated sheets, and may be formed into customized conforming devices to suit particular organs, anatomical sites, or specific surgical applications. FM scaffolds are secured in place using any suitable method known in the art, including sutures, staples or dressings.

In one embodiment, the FM scaffolds are used to cover extensive traumatic wounds or burn injuries, overcoming the inconvenience and complexity of joining a number of smaller scaffold devices together to achieve full coverage. Accordingly, particular FM scaffolds of the invention can cover a wound or injury having a width of 10 cm or more and a length of 10 cm or more.

The presence of the dense layer of connective tissue within the lamina propria and the contoured surface topology make FM well suited in dermal and epithelial regeneration applications. The high tensile strength of FM scaffolds is also particularly useful where the scaffold is required to load bear or is placed under tension. Accordingly, in a particular embodiment, the FM scaffolds of the invention are applied to wounds and surgical sites where there is a need to stimulate tissue repair or regeneration or provide tissue reinforcement. The ECM is naturally remodeled over time, such that FM scaffolds are resorbed and replaced by host tissue.

In other embodiments, FM scaffolds of the invention are used to replace damaged, diseased, or missing heart valves, arteries, veins, urinary bladder, liver, portions of the gastrointestinal tract, or as templates for repair or replacement of head and neck structures. FM, in any of a number of its solid or fluidized forms, can be used as a scaffold for dermal or epidermal repair, injected into various body sphincters such as urinary sphincter or esophageal or gastric sphincters, folded into a tube or partial tube as a conduit for the restoration of nervous tissue or extruded or molded into any shape suitable for its application as a tissue regenerative composition. Accordingly, the FM scaffolds of the invention can be sutured into place in solid sheet form, placed in wounds or body locations in a gel form, or injected in its liquid or particulate form. FM scaffolds of the present invention induce growth of endogenous tissues including epithelial and connective tissues when placed in contact with target tissues in vivo. In addition, the FM can optionally be combined with cells to create tissue constructs to generate new skin, cardiovascular, urogenital, neurological, fascia, tendons, sheaths, ligaments and gastrointestinal tissues. FM can also be seeded with keratinocytes on the denser luminal side of the matrix, and with fibroblasts on the less dense abluminal side for use in certain dermatological applications. FM scaffolds can be seeded with a variety of cell types, including stem cells, for applications in regenerative medicine.

In still other embodiments, FM scaffolds of the invention serve as a substrate for attachment in in vitro cell culture and as a scaffold for cell growth in tissue engineering applications, where FM can promote proliferation and/or induce differentiation of eukaryotic cells. Protocols utilizing non-FM submucosal tissue in in vitro cell culture applications are described, for example, in U.S. Pat. No. 5,695,998, incorporated herein by reference in its entirety. These methods are generally applicable to the use of FM as a substrate for promoting in vitro cell culture. In general, this involves contacting FM with eukaryotic cells in vitro under conditions conducive to eukaryotic cell growth. As described herein, FM scaffolds of the invention can also be used for constructing devices for drug delivery.

As described herein, FM scaffolds can increase proliferation of cells localized near the scaffold attachment site. Accordingly, FM scaffolds can be used to promote, stimulate, or increase cell proliferation in a tissue or organ. In a preferred embodiment, FM scaffolds are used to promote, stimulate, or increase cell proliferation within a wounded tissue or tissue deficit, e.g., within a regenerating wound.

FM scaffolds also promote vascularization (e.g., angiogenesis) within a tissue or organ to which the FM scaffold adheres. Accordingly, FM scaffolds can be used to promote, stimulate, or increase vascularization of a tissue or organ. In a preferred embodiment, FM scaffolds are used to promote, stimulate, or increase vascularization of a wounded tissue or tissue deficit, e.g., within a regenerating wound. Improving vascularization is one way in which FM scaffolds promote wound closure and improve the quality of wound healing.

Bioactive laminated FM scaffolds described herein have many additional clinical applications, including but not limited to delivery of antibiotics (e.g., amoxicillin, penicillins, poly-amines, or quinolines) to surgical sites to treat, inhibit or prevent microbial infection; delivery of antibiotics to wounds and tissue deficits to treat, inhibit or prevent microbial infection at the site; delivery of growth factors (e.g., FGF2, VEGF or PDGF) to a wound or surgical site to promote tissue regeneration and/or vascularization of the tissue; delivery of enzymatic inhibitors to reduce proteolytic activity in chronic wounds; delivery of nitric oxide analogs to a wound or surgical site to promote tissue regeneration; delivery of antimicrobials or anti-biofilm agents to a wound or surgical site to inhibit or prevent infection and/or formation of biofilms.

FM scaffolds of the invention may be formulated and used in a variety of formats, including but not limited to powder, emulsion (fluidized FM), gel or extract. Moreover, the FM scaffolds may be sterilized prior to use by conventional methods, including ethylene oxide treatment, gamma irradiation treatment, gas plasma sterilization, or e-beam treatment.

V. LAMINATED FM SCAFFOLDS USEFUL FOR BREAST RECONSTRUCTION

The characteristics of FM tissue scaffolds of the invention, e.g., strength, elasticity, suture retention, etc., as described herein, make them suitable for a variety of applications in which there is a need to support or reinforce soft tissue. In a particular embodiment, the FM tissue scaffolds are used to cover, position and/or secure breast prosthetics during breast reconstruction, or to cover, position and/or secure native breast tissue or breast prosthetics during mastopexy (i.e., "breast lift").

Breast augmentation is a popular cosmetic procedure in which a prosthesis, i.e., a breast implant, is typically positioned in the chest in one of three positions: over the pectoralis major muscle and under the breast tissue (subglandular), partially under the muscle (partial submuscular), or completely under the muscle (submuscular). Regardless of the location of the implant, the aesthetic outcome of the procedure depends largely on the ability of the surrounding tissue to support the prosthesis such that the prosthesis maintains its position within the patient. Over time, prosthetics can be displaced medially, resulting in symmastia; laterally, resulting in implant excursion into the axilla of the chest cavity, or inferiorly, resulting in "bottoming out." A frequent cause of malposition is inadequate soft tissue support for the weight of the implant. Inadequate soft tissue support is common in patients who receive very large implants, for example, and in patients who have lost a large amount of weight.

This problem is exacerbated in patients undergoing breast reconstruction following treatment for breast cancer, in particular. Cancer treatments such as radiation or chemotherapy weaken the soft tissue needed to support the prosthesis. In addition, attaining sufficient muscle or soft tissue coverage of the prosthesis following mastectomy is a difficult technical challenge. The feasibility of attaining adequate coverage is dependent on the extent of tissue loss and the quality of the remaining tissue. When adequate coverage is not possible, coverage is conventionally achieved by transferring muscle tissue from another site on a patient, which can be associated with donor site morbidity, poor healing, scarring and contracture, and the risk of infection and potential flap necrosis.

The FM tissue scaffold of the present invention addresses these problems in that it can reinforce breast tissue and achieve adequate support for a variety of breast prostheses during breast augmentation/reconstruction. The tissue scaffold may also be used to support native breast tissue or breast prosthetics during mastopexy. The added support of the tissue scaffold is provided, in part, by extracellular matrix derived from the forestomach of a ruminant, as described herein.

FM scaffolds for breast reconstruction can, for example, be flat, or have a concave shape. In a preferred embodiment, the FM scaffold has concavity. Such concavity provides improved conformity and approximation to the rounded shape of the breast tissue and/or the breast prosthesis, reducing dead space and improving positioning, tissue apposition and fixation as compared to a flat sheet. FM is well suited to this application because the natural curvature and shape of the forestomach are useful for forming ECM scaffolds having a natural concavity. In addition, FM scaffolds can be formed around a mold to alter the shape as needed for particular applications (e.g., by increasing or decreasing the curvature of the scaffold).

FM scaffolds for breast reconstruction also can comprise a single or laminated sheet of FM. For example, multiple sheets of FM can be laminated together to increase the strength and thickness of the scaffold, as described herein. In order to support a breast prosthesis and/or native breast tissue, a relatively strong scaffold is needed. Accordingly, FM scaffolds for breast reconstruction can advantageously include a laminated sheet containing 2 or more sheets of FM joined together (e.g., 2, 3, 4, 5, 6, 7, 8, 9, 10, 11, 12, 13, 14, 15 or more sheets). The sheets of FM may be laminated using polymers, using stitches or sutures, or using both polymers and stitches or sutures, as described herein. In a particular embodiment, the layers of laminated FM scaffolds for breast reconstruction are secured together by stitching. Use of stitching and/or adhesive polymers for lamination of multiple FM sheets ensures that the FM scaffold retains its three-dimensional shape prior to and during implantation in a patient.

The FM scaffold also may be perforated or unperforated, as described herein. Perforation reduces the risk of fluid accumulation and seroma formation under the implant, and permits cells to more easily infiltrate the scaffold, allowing for more rapid tissue ingrowth and remodeling of the scaffold.

Figure 2A:
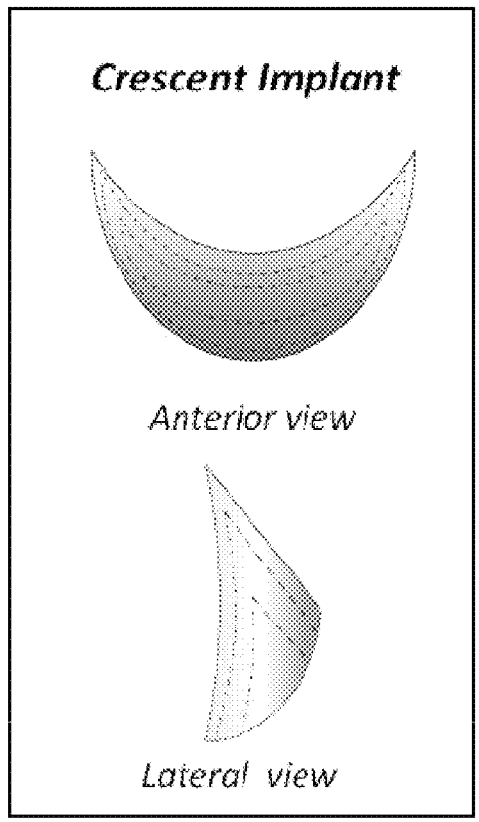
FIG. 2 illustrates two exemplary shapes of FM scaffolds useful in breast augmentation, reconstruction, or mastopexy. (A) depicts a crescent shaped scaffold. (B) depicts an elliptical shaped scaffold.
Figure 2B:
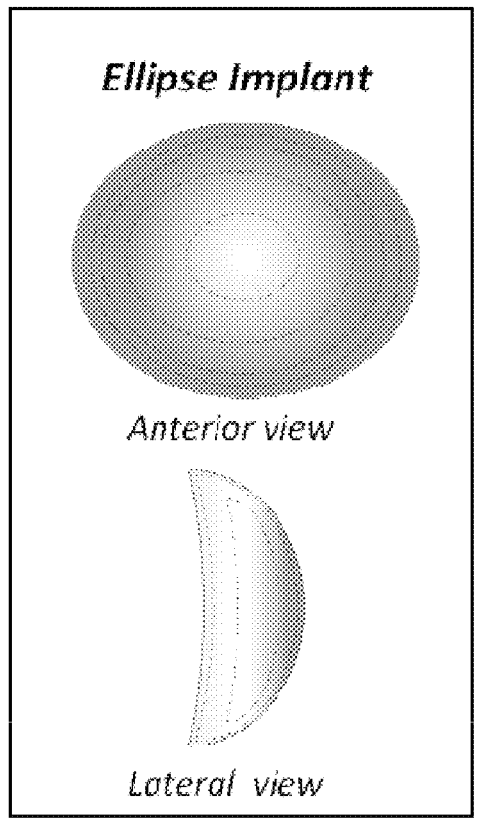

An FM scaffold for breast reconstruction may have a number of different shapes in order to adequately provide coverage for a breast prosthesis during breast augmentation, or for native breast tissue during mastopexy. In preferred embodiments, the FM scaffold has a crescent shape, as illustrated in FIG. 2(A), or an elliptical shape, as illustrated in FIG. 2(B). A semi-circle or half-moon shape may also be used. In one embodiment, the scaffold is sufficiently large to completely or partially cover the lower and/or lateral sections of the breast prosthesis or breast tissue. This allows the scaffold to support the lower pole of the breast prosthesis and/or native breast tissue, emulating the inferior and lateral mammary folds. In this embodiment, the scaffold may be placed in a horizontal or vertical orientation. The scaffold can also be sized for placement in a vertical orientation on the lateral or medial side of a breast prosthesis, to inhibit lateral or medial displacement of the prosthesis.

In particular embodiments of the invention, the FM scaffold for breast reconstruction is between about 3 cm to about 35 cm in length (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 cm), and about 3 cm to about 35 cm in width (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 cm). An exemplary FM scaffold for breast reconstruction is about 3 cm to about 12 cm wide and about 25 cm to about 35 cm long. Additional suitable shapes and sizes of scaffolds are known in the art, as described, for example, in WO 2008/016919 and US 2007/0088434 A1, the contents of which are incorporated herein by reference in their entirety. These shapes and sizes all can be applied to FM scaffolds of the present invention.

When implanted into a patient, the FM scaffold for breast reconstruction undergoes controlled biodegradation as a result of living cell replacement, such that the original scaffold is remodeled. Infiltration of a patient's cells into the scaffold ultimately results in replacement of the ECM of the scaffold with matrix produced by the infiltrating cells. Over time, the scaffold undergoes normal constructive remodeling, resulting in the formation of new tissue to support the breast prosthesis and/or breast tissue. This approach eliminates the need for transferring tissue from another site on the patient, especially in the case of post-mastectomy reconstruction, thereby reducing the complexity and duration of the surgical procedure.

Accordingly, FM scaffolds for breast reconstruction described herein may be used in a wide range of procedures involving breast augmentation or mastopexy, including, for example, in a prophylactic nature at the time or initial placement of a breast prosthesis, in subsequent corrective repositioning procedures, in post-mastectomy reconstruction, and in breast lift procedures. Methods for using tissue scaffolds in the foregoing procedures are well known in the art. Such methods typically involve fixation of the scaffold in the desired position, e.g., across the lower and lateral sections of the breast to support the lower pole of a breast prosthesis/breast tissue, or on the lateral or medial side of the breast to inhibit lateral or medial displacement. Fixation may be achieved using any suitable method known in the art, for example, by placement of sutures or staples, or with use of a tacking device. Over time, the FM scaffold becomes integrated with the surrounding tissue. Other exemplary techniques for using artificial tissue scaffolds in breast reconstruction are described, for example, in WO 2008/016919 and US 2007/0088434 A1, the contents of which are incorporated herein by reference in their entirety. Such techniques are likewise applicable to the FM tissue scaffolds of the invention in breast reconstruction procedures.

VI. ISOLATING TISSUE SCAFFOLDS FROM MAMMALIAN ORGANS USING SEALED TRANSMURAL OSMOTIC FLOW (STOF)

Extracellular matrix scaffolds are traditionally produced from gastrointestinal tissue (e.g., glandular stomach & small intestine) or urogenital tissue (e.g., bladder) by removing the epithelial cells and muscularis mucosa either physically or by chemical separation before or after the tissue is soaked in processing solutions. Physical separation of the mucosal layer typically removes the epithelium, basement membrane, glandular layer, and most if not all of the lamina propria and tunica muscularis.

The decellularisation process removes antigenic components from the scaffold, while conserving the biological activity as well as the mechanical and structural integrity of the ECM. Physical methods of cell removal conventionally include snap freezing, mechanical force, agitation, and sonication. Chemical agents conventionally used for decellularisation include alkaline and acid treatments, non-ionic detergents (e.g., Triton X-100), ionic detergents (e.g., SDS, Triton X-200), zwitterionic detergents (e.g., CHAPS, SB-10, SB-16), Tri(n-butyl) phosphate, hypotonic and hypertonic treatments, and chelating agents (e.g., EDTA, EGTA). Enzymatic processing methods conventionally use trypsin, dipase, endonuclease, and exonuclease.

Processing methods used to date immerse either the open intact organ or a section of the organ in a sequence of processing solutions, thereby exposing all surfaces to each of the solutions. The different characteristics of muscle and epithelial tissue can mean that a solution which has a positive effect on one tissue layer may have a negative impact on another tissue layer. This often results in the use of multiple processing steps, extending the processing time. All processing solutions will have an impact on the biochemical composition, tissue ultrastructure, and mechanical behavior of the remaining ECM. Shorter processing times are desirable because prolonged exposure to processing agents, for example, Triton X-100, SB-10, SB-16, Triton X-200, SDS, and trypsin can be detrimental to the ECM. Shorter processing times also allow higher throughput, improving processing economics and reducing exposure to cellular proteases, which can damage the native ECM ultrastructure. Processing methods used to date rely on diffusion of the processing solutions through the tissue, which can be enhanced somewhat with agitation and increased temperature. Accordingly, processing tissue at physiological temperatures shortens processing time with respect to processing at 4° C. However, physiological temperatures increase endogenous protease activity and, depending on the solution used, can encourage the growth of microbial contaminants.

The present invention overcomes these obstacles and provides an improved method for producing ECM scaffolds from mammalian tissues or organs. According to the method of the invention, different solutions are isolated on each side of a tissue, allowing each solution to be optimized to target the respective tissue layers. One solution is prepared such that it is hypertonic or hypotonic with respect to another solution, such that when the solutions are exposed to opposite sides of a tissue or organ (e.g., the luminal and abluminal sides), a transmural osmotic flow through the wall of the tissue or organ is established. This method of processing aids in decellularisation, separation of tissue layers, and removal of cell debris and processing agents. In addition, this method effectively reduces processing times.

Figure 3:
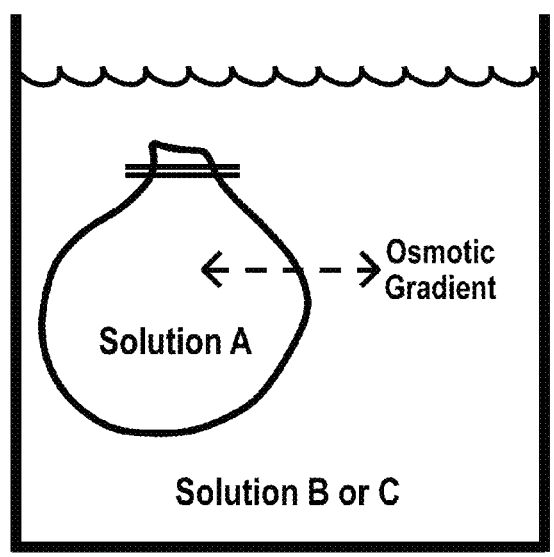
FIG. 3 illustrates one embodiment of a method of processing an organ by establishing a transmural osmotic flow across the organ.

Methods of the invention described herein, in which a transmural osmotic flow is established across the wall of an organ, are referred to as "Sealed Transmural Osmotic Flow" (STOF). STOF methods can be used to process any intact or sealed animal or human tissues to separate and/or decellularise tissue layers, and to thereby extract ECM based scaffolds. Accordingly, this method may be used to process the forestomach tissue of a ruminant to produce FM scaffolds, or to process any other mammalian tissue. An exemplary, non-limiting embodiment of the STOF method is illustrated in FIG. 3. This figure depicts an organ that has been filled with one solution, sealed and then immersed in another solution. The difference in salinity between the two solutions results in a transmural osmotic flow. It will be appreciated that an osmotic gradient can be established in either direction by changing the placement of the solutions (i.e., hypertonic and hypotonic solutions). The gradient is preferably established in a direction mimicking the natural flow of the organ. For example, when processing tissue from the forestomach of a ruminant, the gradient is preferably established from the luminal to the abluminal surface of the tissue. Using biomimicry to determine the direction over which to establish the transmural flow allows the natural physiology and flow properties of the tissue to enhance processing.

The STOF method of the invention is particularly useful for processing tissues that are difficult to delaminate, such as those having a keratinized stratified squamous epithelium, because it allows tissue layers to be targeted with specific agents. STOF can be used to process any intact or partially intact tissue or organ which can be sealed such that a transmural osmotic flow may be created. This includes, for example, tissues or organs of gastrointestinal, urogenital, cardiovascular and dermal origin. This approach may be used to process a wide range of tissues or organs using various processing solutions, including but not limited to those containing salts (e.g., NaCl, KCl, EDTA, EGTA), detergents (e.g., Triton X-100, Triton X-200, sodium dodecyl sulfate, sodium deoxycholate, CHAPs, sulfobetaine, tri(n-butyl) phosphate) and enzymes (e.g., trypsin, endonucleases and exonucleases). Accordingly, this method can be adapted for use with any animal or human tissue or organ which can be fashioned so that the tissue or organ, or a portion thereof, is sealed to allow the creation of a transmural osmotic gradient. A transmural osmotic gradient may also be established across a section of tissue which isolates one solution in a container from a second solution in which it is immersed.

The STOF method performs very well at low temperatures, because the flow is driven by an osmotic gradient rather than being reliant on diffusion and Brownian motion. The rapid efficiency of this method at low temperatures is particularly advantageous in that it minimizes intrinsic protease degradation of biological components of the ECM scaffold, and also prevents microbial growth. In one embodiment, the method is performed at a temperature of less than 6° C. (e.g., 2° C.-4° C.) in less than 36 hours (e.g., preferably in 24 hours or less). This method has been used effectively, for example, to delaminate the keratinized stratified squamous epithelium of the forestomach of a sheep at 4° C. in less than 24 hours. By comparison, processes for generating an esophagus acellular matrix scaffold have been previously reported which take longer than a week (see, for example, Bhrany et al., "The Development of an Esophagus Acellular Matrix Tissue Scaffold," Tissue engineering (2006) 12(2), incorporated herein by reference). This improvement is possible because the transmural osmotic flow draws the processing solutions through the tissue. In another embodiment, the method is performed at or near room temperature (e.g., 18° C.-24° C.). At or near room temperature, processing times can be further reduced. For example, the STOF process has been used to decellularize and delaminate ovine forestomach at room temperature in less than 6 hours. The STOF process also imparts the benefit of treating the different tissue surfaces with different solutions that are optimized to remove the targeted layer (e.g., muscle or epithelium).

The transmural osmotic flow properties are such that the amount of fluid that passes through a tissue is dependent on surface area. The surface area of the tissue may be controlled by the amount of liquid encapsulated within it (the level of distension). Accordingly, a tissue or organ may be fully or partially distended to further increase the surface area of the tissue exposed to the osmotic gradient, and thereby increase the osmotic flow passing into the tissue or organ.

The STOF method of the invention may be used to remove all or a part of a single layer or multiple layers of the tissue being processed. For example, all or a part of the epithelium, basement membrane or tunica muscularis, and combinations thereof, may be removed during or following processing. A number of different solutions may be employed, depending on the tissue to be processed and the composition of the tissue layers that are to be delaminated. In one embodiment, a hypertonic solution is encapsulated within a tissue or organ, and the tissue or organ is immersed in a hypotonic solution. In another embodiment, a hypotonic solution is encapsulated within the organ, and the organ is immersed in a hypertonic solution. In both cases, the direction of osmotic flow will be from the surface of the organ in contact with the hypotonic solution to the surface in contact with the hypertonic solution.

The hypertonic solution may contain one or more buffers, detergents, salts or combinations thereof. Likewise, the hypotonic solution may contain one or more buffers, detergents, salts, or combinations thereof. In all instances, the hypertonic solution contains a higher concentration of solute than the hypotonic solution. For example, a hypertonic salt solution contains a higher concentration of salt than a hypotonic solution. In a preferred embodiment, the hypertonic solution contains a higher concentration of salt than the organ being processed, and the hypotonic solution contains a lower concentration of salt than the organ being processed.

In a particular embodiment, the hypertonic solution contains NaCl. Suitable NaCl concentrations range, for example, between about 0.5 M-10 M (e.g., about 0.5 M, 1 M, 1.5 M, 2 M, 2.5 M, 3 M, 3.5 M, 4 M, 4.5 M, 5 M, 5.5 M, 6 M, 6.5 M, 7 M, 7.5 M, 8 M, 8.5 M, 9 M, 9.5 M or 10 M. In an exemplary embodiment, the hypertonic solution contains about 4 M NaCl.

In another particular embodiment, the hypotonic solution contains Triton X-200 and EDTA. Suitable concentrations of Triton X-200 in the hypotonic solution range, for example, between about 0.001% and 1% (e.g., about 0.001%, 0.005%, 0.01%, 0.05%, 0.1%, 0.25%, 0.5%, 0.75%, or 1%). Suitable concentrations of EDTA in the hypotonic solution range, for example, between about 0.01% and 1% (e.g., about 0.01%, 0.05%, 0.1%, 0.25%, 0.5%, 0.75%, or 1%). In an exemplary embodiment, the hypotonic solution contains about 0.028% Triton X-200 and about 0.1% EDTA.

In another particular embodiment, the hypotonic solution contains SDS. Suitable concentrations of SDS in the hypotonic solution range between about 0.001% and 1% (e.g., about 0.001%, 0.005%, 0.01%, 0.05%, 0.1%, 0.25%, 0.5%, 0.75%, or 1%). In an exemplary embodiment, the hypotonic solution contains about 0.1% SDS. In another exemplary embodiment, the hypotonic solution contains about 0.028% SDS. In a particular embodiment, the hypotonic solution contains about 0.028% Triton X-200, 0.1% EDTA, and 0.1% SDS. In another particular embodiment, the hypotonic solution contains about 0.028% Triton X-200, 0.1% EDTA, and 0.028% SDS.

After initial processing of an organ is achieved by encapsulation of one solution within the organ, followed by immersion of the organ in a second solution, such that a transmural osmotic flow through the wall of the organ is established, further processing is possible (but not required) by removal of the organ from the second solution, and immersion of the organ in a third solution, such that a transmural osmotic flow is again established. The direction of transmural osmotic flow is preferably in the same direction during both stages of processing (i.e., from the luminal to the abluminal surface, or from the abluminal to the luminal surface). The solution encapsulated within the organ need not be removed prior to or during further processing.

Accordingly, in an exemplary embodiment, a hypertonic solution containing NaCl (e.g., about 4 M NaCl) is encapsulated within a mammalian organ (or a portion thereof). The organ is then immersed in a hypotonic solution containing Triton X-200 and EDTA (e.g., about 0.028% Triton X-200 and 0.1% EDTA). The organ is then immersed in a hypotonic solution containing SDS (e.g., about 0.1% SDS or about 0.028% SDS). The solutions are selected based on the desired effect they impart on the processed tissue. For example, a hypotonic solution containing Triton X-200 and EDTA targets the breakdown of the basement membrane between the epithelium and propria submucosa, while a hypotonic solution containing SDS is primarily used to achieve decellularisation. Use of the SDS solution in a STOF method speeds up the removal of cell walls and cellular debris. Accordingly, multiple rounds of STOF processing may be used to achieve the benefit imparted by multiple distinct processing solutions.

In another exemplary embodiment, the STOF method is used to separate and decellularise the tissue layers of the forestomach of a ruminant to generate FM. The process may be used, for example, on the forestomach of cattle, goats or sheep. FM can be generated from the rumen, the reticulum or the omasum using the STOF method. In an exemplary embodiment, the method is used to generate FM from the forestomach of sheep (*Ovis aries*). The forestomach's epithelial surface is a keratinized stratified squamous epithelium which is tightly bound to a basement membrane. It is adapted to resist damage from abrasion, making it difficult to remove using other manual or mechanical methods. In a preferred embodiment, a transmural osmotic flow is established across the forestomach from the luminal to the abluminal surface, mimicking the natural flow of the organ.

In another exemplary embodiment of the invention, three particular solutions are employed for use in forestomach tissue separation and cell removal in a timely manner using the STOF method. Solution A contains about 4 M NaCl, Solution B contains about 0.028% Triton X-200 and 0.1% EDTA, and Solution C contains about 0.1% SDS. Solution A is hypertonic with respect to Solution B and Solution C. Using these solutions to process forestomach tissue, the inverted forestomach is filled with approximately 10 L of Solution A and can be sealed with a cable tie. The filled rumen can then be immersed in Solution B for approximately 16 hours. This combination targets the breakdown of basement membrane between the epithelium and the propria submucosa. The transmural osmotic flow and exposure of the muscle layer to Solution A additionally causes the muscle fibers to soften, aiding physical separation. The filled forestomach can then be immersed in Solution C for approximately 4 hours to achieve decellularisation.

The STOF method speeds up the removal of cell walls and cellular debris. Using the protocol condenses the processing timeframe with respect to traditional methods of processing, as flow is not simply limited to Brownian motion. Moreover, the process can be performed at low temperature (e.g., 4° C. or less) to limit the activity of endogenous proteases and microbiological growth. The ability to process the tissue at low temperatures and in short timeframes enables recovery of higher levels of biological molecules native to the ECM (e.g., growth factors, fibrillar proteins, adhesive proteins, glycosaminoglycans, etc.) in the finished scaffold with respect to processing using other methods. Accordingly, an ECM scaffold generated using the STOF method has distinct biochemical characteristics with respect to scaffolds isolated by other processes.

The present invention is further illustrated by the following examples, which should not be construed as limiting.

EXAMPLES

Example 1

Preparation of Forestomach Matrix (FM) by Sealed Transmural Osmotic Flow (STOF)

Forestomachs from lambs less than two years old were sourced from a local abattoir. The forestomach was inverted so that the epithelial surface was on the outside and the muscular layer was on the inside. It was filled so that the organ was distended with 10 L of 4 M NaCl and sealed with a cable tie. The forestomach was then suspended in a solution containing 0.1% EDTA and 0.028% Triton X-200 for 16 hours, after which it was transferred into a solution containing 0.1% SDS for a further 4 hours. Care was taken to ensure that the organ does not contact other surfaces, including one another, which can limit osmotic flow. This process allowed the Triton X-200/EDTA and SDS solutions to be drawn through the tissue, causing decellularisation and effectively disrupting the basement membrane.

Figure 4:
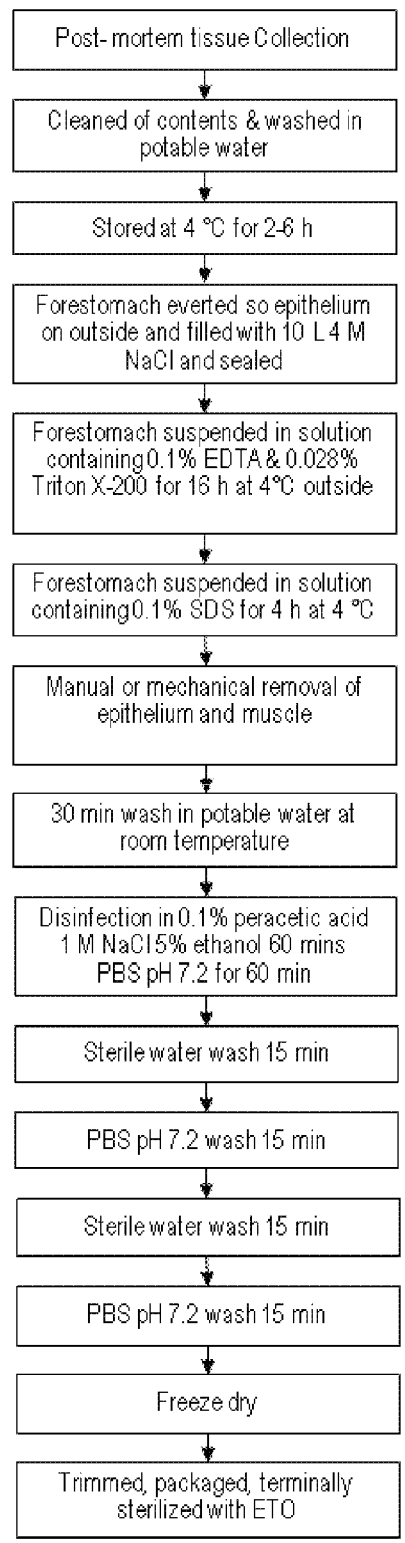
FIG. 4 depicts an exemplary embodiment of tissue processing using STOF to produce a decellularised FM scaffold with a fractured basement membrane.
Figure 5:
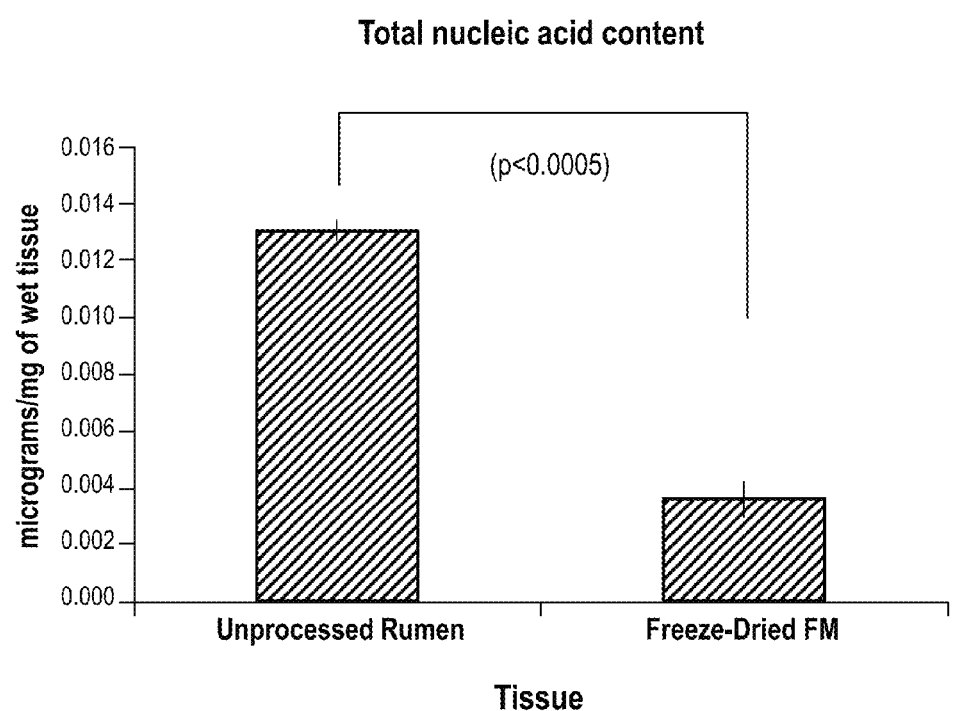
FIG. 5 shows the total nucleic acid content of tissue before and after the STOF process.

The forestomach was removed from the STOF process and the contents were emptied. It was then cut so as to open the organ such that the muscular and epithelial surfaces could be delaminated. This may be carried out by, for example, either manual or mechanical scraping in order to isolate the FM. The FM was washed for 30 minutes using water at room temperature with stirring and then was transferred to 0.1% peracetic acid, 1 M NaCl, in 5% ethanol. This was mixed for 60 minutes followed by 4 sterile wash steps in water (15 min), PBS pH 7.2 (15 min), water (15 min), and PBS pH 7.2 (15 min). The FM was then freeze dried, packaged aseptically and terminally sterilized with ethylene oxide. This embodiment of the STOF process is outlined in FIG. 4. Histological examination of Haematoxylin and Eosin (H&E)-stained sections confirmed that decellularisation was effective. This was further verified by comparing the concentration of DNA in forestomach tissue and FM scaffold. Papain digested samples were incubated with Hoechst 33258 dye (10 µg/mL, Sigma—Missouri, USA), and relative fluorescence units were quantified using a microtitre plate reader. Total DNA concentration was calculated from a standard curve of calf thymus DNA (Sigma—Missouri, USA). As shown in FIG. 5, nucleic acid content was significantly decreased in the FM scaffold as compared to the forestomach tissue, indicating that the FM scaffold was decellularised.

Example 2

Flow Properties and the Effect of Tissue Orientation During the STOF Method

Figure 6:
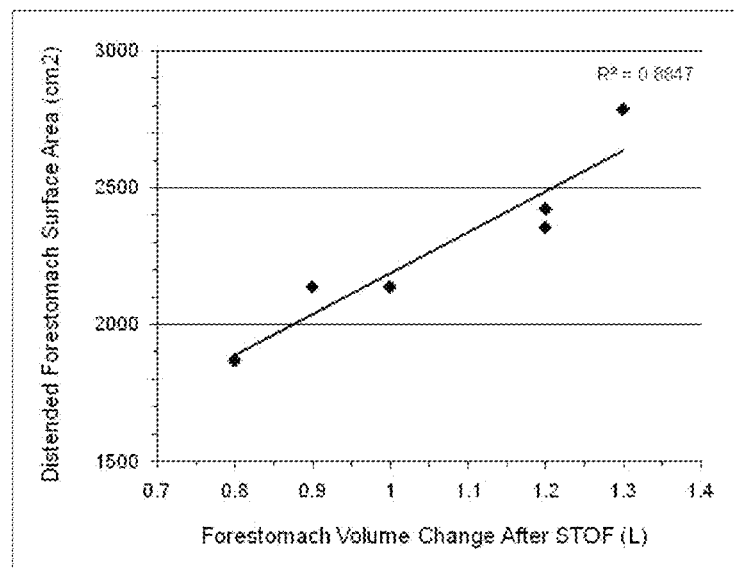
FIG. 6 shows the linear relationship between surface area of forestomach tissue and increases in total forestomach volume after the STOF process.

The following experiment was performed to determine the relationship between the surface area of the forestomach and the osmotic flow of water passing into the forestomach. In this study, 4 M NaCl and water were used to establish an osmotic gradient across forestomach tissue. The surface area of the forestomach can be approximated based on the surface area of a sphere ($4\pi r^2$). The volume of the liquid in the forestomach before and after STOF was used to calculate the volume change of the interior solution (L). There was a linear correlation between the surface area of the forestomach (degree of distension) before STOF and the flow of water into the forestomach (volume change), as depicted in FIG. 6. As shown therein, the osmotic flow of water passing into the forestomach increased with increasing surface area of the sealed forestomach. A reduction in osmotic flow rate was typically observed over time, with the greatest flow achieved during the first 24 hours of STOF.

Figure 7:
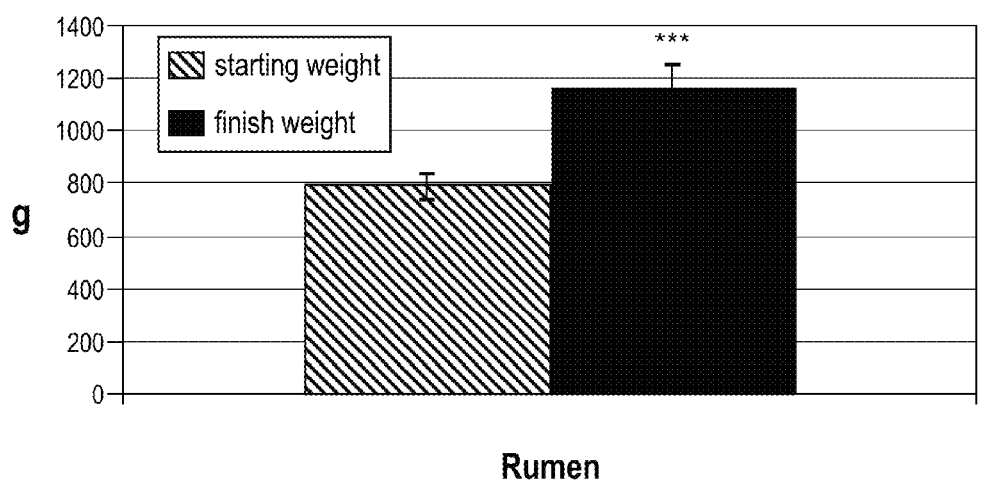
FIG. 7 shows the change in tissue weight as a result of transmural osmotic flow. Fluid passing through and into the tissue resulted in weight gain as tissue hydration increased.

As a means of evidencing the flow through the forestomach along an osmotic gradient during STOF processing, the weight of forestomachs was measured before and after the transmural osmotic flow was applied. The STOF setup was similar to that described in Example 1 and FIG. 3. The weight of the forestomach increased during STOF as a consequence of fluid moving into the tissue. Forestomachs at the beginning of the process weighed 789+/−45 g, whereas at the end of the process the same forestomachs weighed over 1160+/−92 g. Fluid passing into the forestomach tissue resulted in weight gain as tissue hydration increased. These results are depicted in FIG. 7.

Tissue orientation significantly impacted the results achievable with STOF. Establishment of an osmotic gradient across the forestomach in the direction of natural, physiological flow (i.e., flow from epithelium to muscle, e.g., from the luminal surface to the abluminal surface of the forestomach) resulted in successful removal of the muscle layer, epithelial layer and cells from the forestomach. In contrast, when an osmotic gradient was established against direction of natural physiological flow (i.e., flow from muscle to epithelium, e.g., from the abluminal surface to the luminal surface of the forestomach) the tissue became dehydrated and tacky, and subsequent removal of muscle and epithelial layers was more difficult. This data is summarized in Table 2. The direction of flow also affected the appearance of the tissue at the end of processing.

TABLE 2

Tissue orientation and flow properties

| Interior tissue layer | Interior solution | Exterior tissue layer | Exterior solution | Transmural flow | Tissue appearance after STOF | Ease of delamination |
|---|---|---|---|---|---|---|
| Muscle | 0.1% SDS | Epithelium | 4M NaCl | Muscle→Epithelium | Dehydrated | Poor |
| Muscle | 4M NaCl | Epithelium | 0.1% SDS | Epithelium→Muscle | Hydrated | Good |
| Epithelium | 0.1% SDS | Muscle | 4M NaCl | Epithelium→Muscle | Hydrated | Good |
| Epithelium | 4M NaCl | Muscle | 0.1% SDS | Muscle→Epithelium | Dehydrated | Poor |

Example 3

Preparation of Laminated Forestomach Matrix Using Adhesive Polymers

The FM scaffolds described herein may be formatted as single sheets, or may be laminated to form multi-ply laminated compositions of FM. The following example describes the preparation of a laminated FM scaffold using either a collagen polymer adhesive or an adhesive layer prepared from polyvinyl alcohol or hydropropyl cellulose. To prepare the collagen bonded laminate, a gel of collagen polymer was firstly prepared from the parent FM scaffold. This collagen gel retained the same biochemical qualities as the parent material and undergoes remodeling when used as part of a laminated FM scaffold in tissue regeneration. The collagen polymer gel was prepared using heat denaturation of the parent FM scaffold. Finely powdered FM (10% w/v) was heated at 95° C. in purified water or PBS for 90 minutes. The mixture was centrifuged at 10 k rpm for 30 minutes at 35° C. to remove particulates, and the supernatant was retained. On standing and cooling to room temperature the solution solidified to a gel. The gelation of the collagen suspension was reversible, and as such, was heated (>37° C.) prior to direct application as a gel to FM sheets as a layer between two (or more) sheets. On cooling and drying the collagen gel effectively laminated the FM sheets to produce 2-ply laminates.

As the polymeric layer contributes to the overall performance characteristics of the laminated scaffold, different strength and handling characteristics of the laminate were produced by altering the nature of the polymeric adhesive layer. Additionally, changes in the polymeric layer were used to alter the hydration rate of the laminate, its proteolytic stability, and for the delivery of bioactives.

Polyvinyl alcohol and hydroxypropyl cellulose polymeric adhesive were applied as dry films which rehydrated on contact with the wet FM scaffold. Subsequent freeze-drying of the polyvinyl alcohol and hydroxypropyl cellulose containing laminates dehydrated the polymeric layer to yield a laminated sandwich.

The 2-ply laminates were tested for uniaxial strength according to Example 13. Results are summarized as Table 3. Polyvinyl alcohol and hydroxypropyl cellulose laminated FM scaffolds were significantly stronger than collagen laminated FM scaffolds. However, increased strength was offset by a decrease in the elasticity of polyvinyl alcohol and hydroxypropyl cellulose laminated FM scaffolds, as reflected by an increase in the modulus of elasticity and a decrease in the maximum elongation. Polyvinyl alcohol laminated FM scaffold performed best based on yield stress, a term normalized to the thickness of the sample.

This example demonstrates that as the polymeric layer contributes to the overall performance characteristics of the laminated scaffold, different strength and handling characteristics of the laminate were produced by altering the nature of the polymeric adhesive layer.

TABLE 3

Biophysical characterization of FM scaffold laminated with collagen, polyvinyl alcohol and hydroxypropyl cellulose polymeric adhesive layers.

| | Thickness (mm) | Maximum Load (N) | Maximum Elongation (mm) | Maximum Tangential Stiffness (N/mm) | Modulus of Elasticity (Youngs') (GPa) | Yield Stress (MPa) |
|---|---|---|---|---|---|---|
| Collagen | 0.306 ± 0.018 | 17.945 ± 3.088 | 19.418 ± 0.721 | 1.347 ± 0.262 | 0.05 ± 0.01 | 9.77 ± 1.68 |
| Hydroxypropyl cellulose | 0.363 ± 0.023 | 23.533 ± 4.000 | 12.536 ± 0.382 | 2.790 ± 0.438 | 0.096 ± 0.016 | 10.80 ± 1.84 |
| Polyvinyl alcohol | 0.247 ± 0.012 | 22.292 ± 1.172 | 13.502 ± 0.222 | 2.385 ± 0.152 | 0.121 ± 0.01 | 15.07 ± 0.79 |

Errors represent standard errors from five experiments.

Example 4

FM Scaffolds Sewn into Laminates

The FM scaffolds described herein have intrinsic physical properties (e.g. size, thickness, strength) that enable FM scaffold sheets to be sewn or sutured together to form laminates. Laminates can be sewn or sutured together with or without a polymer situated between individual FM sheets. The following example describes the preparation of a 2-ply laminated FM scaffold by stitching the FM layers together with cotton thread.

FM scaffolds were sewn together using cotton thread to form 2-ply laminates. A sewing machine was used to create a straight stitch (approx 2 mm stitch length) through two layers of FM scaffold sheets. The 2-ply laminate was stitched together using parallel stitches approximately 5 mm apart and running the length of the laminate. Uniaxial strength testing of the sewn laminates was conducted using the protocol described in Example 13, and the sewn laminates were compared with 2-ply laminates created using a layer of polymeric collagen adhesive that had not been sewn. Results are shown in Table 4. The strength of the sewn laminate outperformed the collagen-based laminate, as described by the maximum load and yield stress. However, as strength increased, elasticity and elongation of the sewn laminate was reduced relative to the collagen-based laminate.

TABLE 4

Biophysical characterization of FM scaffold laminated with collagen, compared with a sewn FM scaffold laminate.

|  | Thickness (mm) | Maximum Load (N) | Maximum Elongation (mm) | Maximum Tangential Stiffness (N/mm) | Modulus of Elasticity (Youngs') (GPa) | Yield Stress (MPa) |
|---|---|---|---|---|---|---|
| Collagen | 0.306 ± 0.018 | 17.945 ± 3.088 | 19.418 ± 0.721 | 1.347 ± 0.262 | 0.05 ± 0.01 | 9.77 ± 1.68 |
| Sewn laminate | 0.272 ± 0.031 | 24.617 ± 2.105 | 13.795 ± 1.207 | 2.731 ± 0.284 | 0.130 ± 0.017 | 15.10 ± 1.29 |

Errors represent standard errors from five experiments.

Example 5

Distribution of Collagen IV and Laminin in a Disrupted Basement Membrane

FM scaffold obtained according to the process set forth in Example 1, as well as the epithelium removed during delamination of the forestomach tissue, were fixed by immersion in 7% neutral-buffered formalin and embedded in paraffin wax. Sections were cut at 10 µm thickness using a microtome before the section was relaxed in heated water and mounted on APE-coated slides. Sections were fixed to the slides by immersion in paraformaldehyde for 10 minutes and stored in dust-free conditions at room temperature. Paraffin from slides was dissolved by immersion in four 5 minutes washes of 100% xylene and rehydrated through descending concentrations of ethanol before immersion in 50 mM TBS (pH 7.4). Endogenous peroxidases were quenched using 5% $H_2O_2$ in 70% methanol for 30 minutes. Staining procedures were carried out according to the protocols of a DAB secondary detection kit (Chemicon). Sections were washed three times in TBS for 5 minutes each time, followed by incubation in blocking serum for 30 minutes to block non-specific binding. Subsequently, sections were incubated in an appropriate primary antibody (i.e., an antibody which recognizes laminin or collagen IV, such as a rabbit anti-ovine primary antibody), at a dilution of 1:100 (both primary antibodies were optimized in the tissue prior to use in this assay). Sections were incubated in primary antibody in a humidified chamber for 30 minutes at ambient temperature. Sections were then washed in TBS containing 0.1% Triton X-100 (TrTBS), and then twice in TBS for 5 minutes each. Sections were incubated with the secondary antibody provided in the DAB secondary detection kit, described above, for 10 minutes at room temperature. Sections were subsequently washed once in TrTBS and twice in TBS followed by incubation with strepavidin-biotin conjugate (Vector Laboratories, USA) at room temperature for 10 minutes. Slides were washed three times in TBS prior to incubation with the chromogen diaminobenzidine tetrachloride (DAB) for 1-5 minutes to allow maximal antigen staining with minimal background staining. DAB labeling was halted by washing sections in $dH_2O$. Sections were then counterstained with haemotoxylin, rewashed in running tap water, dehydrated in ascending concentrations of ethanol, cleared in xylene, mounted using DPX mountant and stored at room temperature until viewing. Labeled proteins appeared brown, whereas the haemotoxylin-labeled nuclei appeared blue. Negative controls were carried out by omitting the primary and/or secondary antibody application during the above procedures. Slides were viewed under a light microscope and photos were taken using AnalySIS software.

Immunohistochemistry of the FM scaffold revealed collagen IV and laminin were localized to the epithelial and vascular basement membranes and were also present within the dense layer of matrix deep within the lamina propria. Laminin and collagen IV staining of the FM scaffold revealed that the basement membrane was not a continuous surface, but rather was discontinuous or disrupted. Collagen IV and laminin were additionally seen in samples of epithelium taken after delamination of the tissue. Staining of the epithelial tissue revealed that collagen IV and laminin were localized to fragments of basement membrane. The presence of laminin and collagen IV on both the epithelial layer and the luminal surface of the FM scaffold indicates that the basement membrane is disrupted during delamination of the forestomach tissue. Disruption and fracture of the basement membrane during processing leads to release of the epithelium. Significantly, the presence of laminin and collagen IV in the lamina-propria layer of the FM scaffold provides a source of these important cell adhesion molecules during tissue regeneration.

Example 6

Basement Membrane Disruption and Fracture

Suspending an ovine forestomach containing NaCl in a hypotonic processing solution which contains 0.028% Triton X-200 and 0.1% EDTA for 16 hours resulted in shedding of the epithelium from the underlying propria submucosa as the basement membrane was disrupted.

Analysis by immunohistochemistry of sections taken from the epithelial sheets showed the presence of collagen IV and laminin in the remnants of the basement membrane on both the FM and the shed epithelial layer (described above). Based on the above, it is clear that the processing solutions are disrupting the structure of the basement membrane, causing the basement membrane to be fracture and the epithelial layer to be released. Following processing, the epithelium peeled away in sheets from the underlying propria-submucosa. This "sheeting" of the epithelium occurred following immersion in Triton X-200 and EDTA solution during the STOF process.

Figure 8:
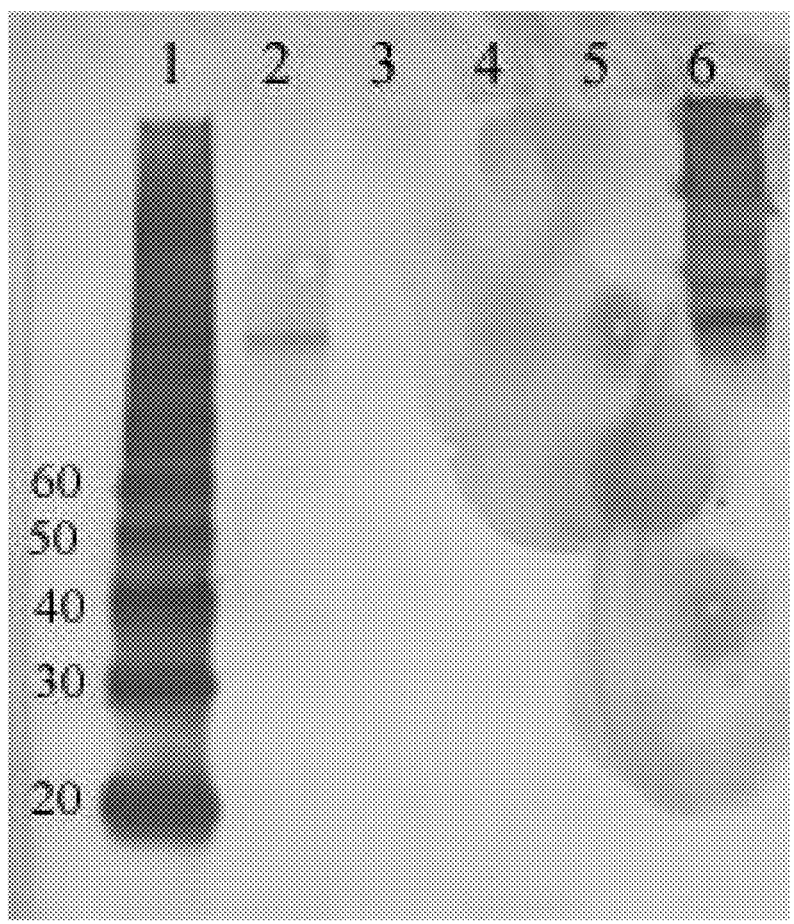
FIG. 8 shows a Western blot detection of laminin in STOF solutions at completion of the STOF process. The contents of each lane on the Western blot are as follows: Lane 1: Magic Markers; Lane 2: Sample of 0.1% Triton X-200 solution from outside the rumen taken at completion of the STOF process; Lane 3: Sample of the 4 M NaCl solution from inside the rumen taken at completion of the STOF process; Lane 4: Sample of 0.1% Triton X-200+0.1% EDTA solution from outside the rumen taken at completion of the STOF process; Lane 5: Sample of 0.1% SDS solution from outside the rumen taken at completion of the STOF process; Lane 6: Laminin standard.

Western blotting revealed that laminin, a major component of the basement membrane, was being released into solution during the STOF process. This was evident when solutions of either 0.028% Triton X-200, or 0.028% Triton X-200+0.1% EDTA, were sampled during the STOF process. Proteins present in the samples were separated by gel electrophoresis and visualized using an anti-laminin antibody (FIG. 8). Laminin was solubilized by either of the 0.028% Triton X-200 containing solutions (Lanes 2 and 4, FIG. 8) but not by a solution containing NaCl (Lane 3, FIG. 8) or 0.1% SDS (Lane 5, FIG. 8).

A biochemical analysis of the FM scaffold and the epithelial layer shed during processing revealed that laminin, a principle basement component, was present in both fractions. Laminin in both the FM scaffold and the epithelial tissue were quantified using ELISA according to Example 7, below. Laminin concentrations in the FM scaffold and epithelial tissue were 5.87±2.16 and 17.3±1.1 µg/g, respectively. The fact that laminin was detected in relatively high concentrations in the shed epithelial tissue further supports the observation that during STOF processing the basement membrane of the forestomach tissue was fractured, leading to loss of the epithelial layer.

Example 7

Biochemical Composition of FM Scaffold

An extensive study was undertaken to understand both the major and minor components of FM scaffold, e.g., scaffold obtained according to the process set forth in Example 1. Macroscopically the product can be considered as a collagen matrix that will support cellular infill and differentiation. However, the manufacturing process has been developed in such a way as to retain minor biologically active components, for example growth factors and glycosaminoglycans (GAGs). These minor components play an equally important role in wound healing and their presence in FM scaffolds imparts beneficial wound healing properties to the product.

In all cases the biochemical composition of the FM scaffold was compared with the porcine small intestine submucosa (SIS), and the raw material, ovine forestomach.

In all cases, tissue samples were firstly frozen in liquid nitrogen and milled in a spice grinder to yield fine particulate. The powder was extracted and analyzed for biochemical macromolecules according to established procedures. Biochemical analysis of the major components is summarized in Table 5.

Total soluble collagen was quantified by an enzymatic digestion of the powdered samples (5 mg/mL pepsin, 0.5 M acetic acid, 37° C., 16 h), followed by centrifugation and analysis of the supernatant using the Sircol™ Soluble Collagen Kit (Biocolor—County Antrim, UK). Total soluble collagen of the samples was calculated from a standard curve of rat tail collagen I (Gibco Invitrogen—California, USA). The concentration of total soluble collagen was approximately equal in the ovine forestomach, FM scaffold and SIS.

While soluble collagen quantification may represent the relative abundance of physiologically available collagen, it does not take into account the pepsin-insoluble collagen components of the matrices. Thus, to understand total collagen content of the test samples, a hydroxyproline analysis was conducted according to established procedures. Samples were hydrolyzed in 6 M HCl (120° C., 60 minutes), then the hydroxyproline residues reacted to form a pyrrole chromophore that was quantified using absorbance. Total collagen was calculated from a standard curve of hydroxyproline (Sigma—Missouri, USA), where it was assumed the ratio of hydroxyproline to total collagen is 7.14. In the FM and SIS scaffolds, collagen was approximately 80-80% by composition. As expected, pepsin-soluble collagen represented only a small fraction of the total collagen present in the samples.

Collagen IV is an important component of the basement membrane that promotes cell adhesion and proliferation. The basement membrane of FM is partially intact, suggesting that this feature might impart beneficial proliferative properties to the product. Collagen IV was solubilized with 4% SDS (37° C., 16 hours) in extraction buffer, dialyzed against PBS, quantified using a direct ELISA probed with anti-collagen IV antibody (Abacus ALS—Queensland, Australia), and detected with a secondary antibody conjugated to HRP (Abacus ALS—Queensland, Australia). Collagen IV was quantified relative to a standard curve of partially purified bovine collagen IV (Chemicon Millipore—Massachusetts, USA). Collagen IV represented a small proportion of total collagen in the matrices (approximately 2%).

Elastin is an important structural protein which forms a network of elastic fibers within the ECM to provide resilience, texture, durability and the ability to recoil after stretching. Elasticity of the protein is imparted by extensive cross-linking of the soluble tropoelastin monomers to yield an extensive covalent array. Given its extensive lysine crosslinking, elastin is especially insoluble and therefore difficult to quantify in biological samples. In order to understand the relative levels of elastin, both 'soluble' and 'insoluble' elastin were quantified. Samples of matrices were solubilized in 0.25 M oxalic acid (105° C., 16 hours), centrifuged to pellet out the insoluble material, then the supernatant analyzed using the Fastin™ Elastin Kit (Biocolor—County Antrim, UK), according to the manufacturers recommendations. Solubilized elastin was quantified relative to a standard curve of partially purified bovine elastin. The concentration of soluble elastin composition was approximately ten-fold less in FM relative to SIS. Insoluble elastin was quantified using a mass balance assay according to established procedures. Briefly, samples were extracted with (1) ethanol/diethyl ether (1:1, 15 minutes, rt ° C.); (2) 0.3% SDS (16 hours, rt ° C.); and (3) 0.1 M NaOH (15 minutes, 100° C.). Samples were centrifuged and the supernatant discarded after each extraction step. Insoluble elastin remained after the extraction procedure; as such, total insoluble elastin was calculated by comparing the dry weight of the sample before and after the extractions. Total insoluble elastin concentrations were lower in the FM than in the SIS (3.0% and 5.3%, respectively).

Glycosaminoglycan molecules (GAGs), including heparan sulphate and chondroitin sulphate, bind growth factors and cytokines, and control water retention and gel properties within the ECM. The heparan binding properties of numerous cell surface receptors and of many growth factors (e.g. FGF family, VEGF) make heparan-rich GAGs extremely desirable components of scaffolds for tissue repair. Total GAGs were quantified using a colorimetric dye-binding assay (Blyscan Sulfated Glycosamine Kit; Biocolor—County Antrim, UK) following papain (125 µg/mL) digestion of the powdered samples. GAG concentration was calculated from a standard curve of chondroitin sulphate (Sigma—Missouri, USA). SIS had higher concentrations of total sulphated GAGs than both ovine forestomach and FM (7.3±0.4, 3.9±0.1 and 0.6±0.1 mg/g, respectively). Heparan sulphate concentrations were 0.2 mg/g and 2.1±0.1 mg/g for FM and SIS, respectively. A more detailed discussion of the quantification of heparan sulphate is provided below. The concentrations of hyaluronic acid (HA) in each of the three samples were determined using an ELISA kit (Echelon Biosciences—Utah, USA). HA was found to be present in low concentrations in all three samples.

A critical feature in the manufacture of FM are steps that decellularize the ECM and thereby reduce any negative host response to the xenoplant. Typically, decellularization is achieved through detergent-mediated disruption of cell membranes, leading to cell lysis and solubilisation of cellular components. The presence of nucleic acids was used as a surrogate marker for the cellularity of the matrices. DNA fragments in their own right also pose some risk off invoking a host-mediated immune response. Total DNA was quantified using a fluorescent dye-binding assay. Papain digested samples were incubated with Hoechst 33258 dye (10 μg/mL, Sigma—Missouri, USA), and relative fluorescence units were quantified using a microtitre plate reader. Total DNA concentration was calculated from a standard curve of calf thymus DNA (Sigma—Missouri, USA). The concentration of DNA in FM was less than that in SIS (0.2% and 0.4%, respectively). As expected, there was a significant reduction in DNA in FM relative to the ovine forestomach raw material (0.2% and 2.6%, respectively).

Tissue lipids are found primarily in cell membranes and therefore offer another surrogate that can be useful in assessing the extent of decellularization of the ECM matrices. The lipid content of the FM scaffold was determined using mass balance following ether extraction of the samples. Both FM and SIS scaffolds had approximately 6% lipid composition, while ovine forestomach had a lipid composition of 14.4%.

migration and differentiation. Fibronectin binds collagens and heparans and, importantly, provides ligands for the adhesion of cell surface integrin receptors leading to cell attachment and proliferation. Fibronectin was quantified using QuantiMatrix Human Fibronectin ELISA Kit (Chemicon Millipore—Massachusetts, USA) following dialysis of samples extracted with 4% SDS. The concentration of fibronectin in FM was significantly higher than SIS, 13.67±1.64 and 5.00±0.05 μg/g, respectively.

Laminin is an ECM protein which is capable of binding to type IV collagen molecules, heparan sulphate, and integrin receptors, thus forming important connections between cells and the basement membrane or the ECM. Laminin was quantified in samples extracted with 4% SDS using a QuantiMatrix human Laminin ELISA Kit (Chemicon Millipore—Massachusetts, USA), and concentrations were determined relative to a standard of human laminin. The concentrations of laminin in FM and SIS were approximately equal.

Basic Fibroblast Growth Factor (FGF2) is multifunctional and plays an important role in wound healing including the promotion of endothelial cell differentiation during angiogenesis, and cell differentiation and migration of a number of cell types. Samples were analyzed for the presence of FGF2 using the Human FGF-Basic ELISA Development Kit (Peprotech—New Jersey, USA). Scaffold samples were extracted with 4% SDS extraction buffer and dialyzed against PBS. FGF2 was then quantified using human FGF2 as a standard. Concentrations of FGF2 in the ovine forestomach and in the

TABLE 5

Major biochemical components of the ovine forestomach, and FM and SIS tissue scaffolds

| | Ovine Forestomach | | FM | | SIS | |
|---|---|---|---|---|---|---|
| | (mg/g ± SE)[1] | % composition | (mg/g ± SE)[2] | % composition | (mg/g ± SE)[1] | % composition[3] |
| Total Collagen | 142.7 ± 9.7 | 40.5 | 821.0. ± 9.0 | 89.72 | 629.7 ± 39.7 | 80.6 |
| Soluble Collagen | 55.3 ± 3.21 | —[3] | 51.7 ± 3.3 | —[3] | 48.7 ± 5.3 | —[3] |
| Collagen III | 61.3 ± 0.7 | —[3] | 196.8 ± 6.9 | —[3] | 171.5 ± 11.1 | —[3] |
| Collagen IV | 46.6 ± 1.5 | —[3] | 9.7 ± 2.1 | —[3] | 6.6 ± 1.1 | —[3] |
| Soluble Elastin | 112.0 ± 15.0 | 32.0 | 4.8 ± 0.5 | 0.53 | 54.0 ± 6.1 | 6.9 |
| Insoluble Elastin | 30.9 ± 6.4 | 8.8 | 27.5 ± 4.5 | 3.01 | 41.4 ± 5.0 | 5.3 |
| Total GAGs | 3.9 ± 0.1 | 1.1 | 0.6 ± 0.1 | 0.07 | 7.3 ± 0.4 | 0.9 |
| Heparan Sulphate | N.D. | —[5] | 0.2 | —[5] | 2.1 ± 0.1 | —[5] |
| Hyaluronic Acid | 1.95 ± 0.02 | 0.6 | 0.4 ± 0.1 | 0.05 | 1.58 ± 0.11 | 0.2 |
| DNA | 9.0 ± 0.5 | 2.6 | 1.7 ± 0.5 | 0.19 | 2.7 ± 0.2 | 0.4 |
| Lipid[6] | 50.2 ± 2.9 | 14.4 | 59.0 ± 5.2 | 5.7 | 44.7 ± 4.0 | 5.7 |

[1]Errors represent standard error from triplicate experiments.
[2]Errors represent standard errors from at least three independent production lots, tested in triplicate.
[3]Percentage composition based on total collagen from the hydroxyproline analysis only excludes collagen III, collagen IV and soluble collagen.
[4]N.D. = Not detected.
[5]Percentage composition excludes heparan sulphate as this is included in total GAGs.
[6]As determined from the insoluble elastin - mass balance assay.

FM and SIS tissue scaffolds, as well as ovine forestomach, were analyzed for minor biochemical components, fibronectin, laminin and the growth factors VEGF, FGF2, TGFβ1, and TGFβ2. Results are summarized in Table 6.

Fibronectin is a glycoprotein that is distributed throughout the ECM and plays an important role in cell growth adhesion, FM were less than the concentration shown in SIS (1.70±1.38, 0.74±0.0.09 and 4.85±0.84, respectively).

The growth factors VEGF, TGFβ1, and TGFβ2 were quantified using commercially available ELISA kits, according to the manufacturer's instructions (Bender Medsystems and Peprotech). Firstly, powdered FM was extracted using either 2 M urea (37° C., 48 hours), or 4 M guandinium hydrochloride (37° C., 48 hours). Samples were centrifuged and the supernatant was filtered prior to ELISA quantification. Growth factors TGFβ2 and VEGF were also quantified using Western blot according to established procedures. Antibodies directed against the growth factors and positive controls (where available) were used accordingly; these included rabbit anti-TGFβ2 polyclonal (Abcam®), TGFβ2 monoclonal (Invitrogen™), and rabbit polyclonal anti-VEGF (Abcam®). Additionally, TGFβ1 was quantified using dot-blot employing rabbit polyclonal anti-TGFβ1 (Abcam®) and purified TGFβ1 (Invitrogen™) as a positive control.

TABLE 6

Minor biochemical components of the ovine forestomach, and the FM and SIS scaffolds

|  | [1]Ovine Forestomach (μg/g ± SE) | [2]FM (μg/g ± SE) | [1]SIS (μg/g ± SE) |
|---|---|---|---|
| Fibronectin | 15.30 ± 1.17 | 13.67 ± 1.64 | 5.00 ± 0.50 |
| Laminin | 6.30 ± 0.24 | 5.87 ± 2.16 | 6.00 ± 0.30 |
| FGF2 | 1.70 ± 1.38 | 0.74 ± 0.09 | 4.85 ± 0.84 |
| TGFβ1 | N.T | 0.19 ± 0.01 | N.T |
| TGFβ2 | N.T | 0.02 ± 0.01 | N.T |
| VEGF | N.T | 0.09 ± 0.03 | N.T |

[1]Errors represent standard error from triplicate experiments.
[2]Errors represent standard errors from three independent production lots, tested in triplicate.
N.T. = not tested.

Example 8

FM Scaffold Contains the Glycosaminoglycan (GAG) Heparan Sulfate

The N-sulphated GAG heparan sulphate is an important ECM-bound GAG that plays an important role as a co-factor to FGF2 bioactivity. Heparan sulphate is required for the bioactivity of FGF2 as it binds directly to FGF2 receptors in the presence of FGF2, thus stabilizing the FGF2-receptor complex. Heparan sulphate also binds free FGF2, stabilizing the growth factor and prolonging its circulating half-life. According to U.S. Pat. No. 4,902,508 and U.S. Pat. No. 6,099,567, small intestinal submucosa contains heparan sulphate whereas stomach submucosa does not. The absence of heparan sulphate in stomach submucosa limits any bioactivity associated with FGF2 in ECM scaffolds derived from stomach submucosa.

Forestomach submucosa was analyzed to determine the presence of heparan sulphate. Papain digested samples of FM were resolved by cellulose acetate GAG gel electrophoresis according to established procedures. GAGs present in the FM sample migrated similarly to a standard sample of heparan sulphate, but not chondroitin sulphate B or hyaluronic acid. By analyzing the densitometry of the Alcian blue stained gel it was possible to quantify the amount of heparan sulphate present in the FM sample. Heparan sulphate concentration was approximately 0.2 mg/g.

Heparan sulphate levels were also determined using more quantitative methods. Total GAGs were quantified in FM using the commercial Blyscan GAG detection kit, as described above. Using this approach it was possible to determine the concentration of total GAGs (both N-sulphated and O-sulphated GAGs) in a sample, including chondroitin sulphates (4- and 6-sulfated), keratan sulphates (alkali sensitive and resistant forms), dermatan sulphate (containing iduronic & glucuronic acid) and heparan sulphates (including heparans). With a modification to the procedure it is possible to cleave N-sulphated heparan sulphate polymers to their constituent monomers in the presence of O-sulphated GAGs using nitrous acid treatment. In this way it is possible to quantitate heparan sulphate as a percentage of the total GAGs present in a sample. Using this approach it was shown that SIS had a concentration of heparan sulphate of 2.1±0.1 mg/g. Under identical conditions, surprisingly heparan sulphate could not be detected in either FM or ovine forestomach tissue.

It is possible that the nitrous acid modification to the Blyscan assay was ineffective at resolving heparan sulfate in FM extracts. As such, alternate methods were explored to further verify the presence of heparan sulphate in the FM matrix.

The presence of heparan sulfate was confirmed by a heparanase digestion of an FM extract prior to total GAG analysis using the Blyscan assay. A papain treated FM extract was digested to constituent disaccharides using heparan lyases I (0.5 mU), II and III (both at 0.5 mU) (Seikagaku Corporation, Japan) at 37° C. for 24 hours. After 24 hours, an additional lyase digestion was performed to ensure complete digestion of the sample. Samples before and after lyase digestion were analyzed for toal GAGs using the Blyscan assay. Disaccharides are unreactive to the Blyscan GAG assay. Results are summarized in Table 7.

TABLE 7

Heparanase digestion of FM extracts.

| Lyase treatment | Heparan sulfate (50 μg/mL) | FM extract (μg/mL) | FM extract (mg/g) | Concentration of lyase sensitive heparan sulfate |
|---|---|---|---|---|
| Untreated | 52 | 70 | 0.7 | NA |
| 24 hours | 15 | 42 | 0.4 | 0.3 |
| 48 hours | 13 | 46 | 0.4 | 0.2 |

Heparan lyase digestion of the sample significantly reduced the concentration of total GAGs, as determined using the Blyscan assay (Table 7). For example, the concentration of heparan sulfate standards (prepared at 50 μg/mL) before and after lyase digestion were 52 μg/mL and 15 μg/mL, respectively. There was no significant difference in samples treated for 24 or 48 hours, suggesting that lyase digestion was essentially complete after the first 24 hour incubation. Lyase digestion of a heparan sulphate standard reduced the reactivity of the sample to the Blyscan reagent, but not to background levels. This may be explained by the presence of additional GAGs in the heparan standard that are not sensitive to heparanase digestion, and/or that heparanase digestion of the standard is not 100% efficient at converting heparans to their constituent disaccharides. Heparan lyase digestion of the FM extracts significantly reduced the total GAGs present in the digested samples (e.g. 70 μg/mL, 42 μg/mL before and after lyase digestion, respectively). Based on this analysis, lyase sensitive heparan sulphate represents approximately 40% of total GAGs present in FM. This represents a heparan sulphate concentration of 0.2 mg/g, assuming total GAG concentration prior to lyase digestion is 0.7 mg/g. This finding is in line with the gel electrophoresis analysis described above, where heparan sulphate concentrations were determined to be 0.2 mg/g.

FM extracts were further analyzed by HPLC to establish the presence of chrondroitin sulphate, another major GAG that may be expected to be present in the FM matrix. A papain-digested extract of FM was digested (20 hours at 37° C.) with 5 U/mL chondroitinase ABC (Seikagaku Corporation, Japan) in Tris buffer (50 mM pH 8.0, 0.4 M sodium acetate, 0.1% BSA) to hydrolyse the chondroitin polymer to consistuent monomers, i.e. non-sulphated chondroitin, chondroitin 6-sulphate, chondroitin 4-sulphate, chondroitin 2,6-sulphate, chondroitin 2,4-sulphate, and chondroitin 2,6-sulphate. The chondroitinase digested sample was also analyzed by HPLC, whereby the concentration of chondroitin monomers in the extract was used to infer the concentration of chondroitin sulphate prior to chondroitinase digestion. Samples were centrifuged and the supernatant analyzed by RP-HPLC. Injections (20 µL) were made to a Phenosphere™ SAX 5 um column (Phenomenex—California, USA) at 22° C. The mixture was resolved using an aqueous HCl (pH 3.5)/1.5 M NaCl in HCl (pH 3.5) gradient, at 1.0 mL/min flow rate. Peaks were detected at 232 nm.

Using this HPLC method none of the expected monomers of chondrotin sulphate were detected, suggesting that chondrotin sulphate is not a major component of the total GAGs detected in FM.

Taken together these findings imply that heparan sulphate is present in the FM scaffold, but at lower concentrations than that found in SIS (Table 8). It is interesting to note that the total GAG concentration of FM was determined at 0.6±0.1 mg/g, suggesting that other GAG components, excluding chondroitin sulfate, may be present in the extract that were not resolved by gel electrophoresis.

TABLE 8

Quantification of heparan sulphate using nitrous acid hydrolysis and 1,9-dimethy-methylene blue detection.

|  | Ovine Forestomach FM | SIS |
| --- | --- | --- |
| Heparan Sulphate (mg/g) | N.T. 0.2[1] | 2.1 ± 0.1[2,3] |

[1]As determined from gel electrophoresis analysis, and Blyscan assay of lyase pre-treated extracts.
[2]As determined from Blyscan assay of nitrous acid pre-treated extracts.
[3]Errors represent standard error from triplicate experiments.
N.T. = not tested.

Example 9

FM Tissue Bimodal Scaffold Structure

Ovine FM was prepared using the method outlined in Example 1. Ovine glandular stomach submucosa was also prepared from glandular stomach by delaminating the muscle and epithelium from the submucosa and then soaking the scaffold in water for two hours to lyse the cells. Hematoxalin & Eosin (H&E) stained slides were prepared for histology using standard techniques.

(i) Gross Appearance: The glandular stomach submucosa had a similar macroscopic appearance on both the luminal and abluminal surfaces. In contrast, the FM scaffold had visible differences in the surface contours between the luminal and abluminal sides of the matrix. The papillae of the luminal side showed markedly similar topology to the rete ridges of normal skin, whereas the abluminal side, left behind when the tunica muscularis is removed, was smooth. The bimodal nature of this scaffold is important in terms of its interactions with different cell types in a healing situation.

(ii) Histology: The propria-submucosa layer is unique to the forestomach of ruminants and not present in other gastrointestinal tissue. The lamina propria of the glandular stomach and small intestine is a loose areolar layer between the glands of the mucosa which is predominantly removed during the delamination process. A layer of tissue called the lamina muscularis mucosa separates the lamina propria and submucosa in the small intestine and glandular stomach. The lamina muscularis mucosa is absent in the rumen of the forestomach, and consequently the lamina propria and submucosa blend to form the propria-submucosa. The FM scaffold consisted of remnants of the basement membrane and the propria-submucosa. Analysis of the scaffold by microscopy revealed that the FM had a dense layer of ECM within the lamina propria of the propria-submucosa which accounted for approximately the top 20% of the matrix thickness. The abluminal side of the FM scaffold had a more open reticular structure. The FM scaffold had a contoured luminal surface, and a dense lamina propria on the luminal side, whereas on the abluminal side, the ECM of the submucosa was more open and reticular. Accordingly, FM scaffolds have a bimodal structure. This structure makes the FM well suited to encouraging epithelial regeneration on the dense luminal side of the matrix, and fibroblast invasion on the less dense abluminal side of the matrix when used as a medical device for tissue regeneration.

(iii) Scanning Electron Microscopy (SEM): Scanning electron micrographs of FM and glandular stomach submucosa were performed on lyophilized tissues from a one week old calf and a 6 month old lamb to compare the luminal and abluminal surfaces. FM scaffold from lamb was prepared using the method set forth herein. "Unprocessed" forestomach propria-submucosa was prepared by removing the epithelial and muscle layers, but not undertaking the STOF process on the tissue. Glandular stomach submucosa was prepared from the glandular stomach of a lamb by delaminating the muscle and epithelium from the submucosa and then soaking the scaffold in water for two hours to lyse the cells. Comparison of SEM images of neonatal bovine FM, ovine FM, and glandular stomach clearly indicated that FM has two distinct surfaces and has clear sidedness, whereas glandular stomach submucosa is very similar on both sides.

Cross-sectional SEM images of FM and glandular stomach submucosa demonstrated the presence of a thick, dense layer of ECM on the luminal surface of the FM propria-submucosa, compared with the thinner and more uniform structure of the glandular stomach submucosa. Notably, the dense layer of ECM is absent from the glandular stomach submucosa.

Example 10

Surface Area of FM Tissue Matrix

Six forestomachs and six glandular stomachs from six month old lambs were collected from a local abattoir. Grossly, the forestomach is a substantially larger organ than the glandular stomach, and therefore is ideally suited for producing large surface area scaffolds.

To compare the difference in size, the respective volumes of the forestomach and the glandular stomach were measured. It was found that forestomachs were typically 12-15 liters in volume, whereas glandular stomachs were limited to 2.5-3 liters. Based on an approximation to the surface area of a sphere, this represents an area of approximately 405 cm$^2$ for the forestomach, compared with 104 cm$^2$ for the glandular stomach.

Table 9 summarizes the differences between ECM scaffolds derived from ovine forestomach and glandular stomach. The typical dimensions of these ECM sheets are shown in Table 9 to illustrate the approximate difference in the dimensions of scaffolds obtained from the forestomach and glandular stomach. It was also noted that the glandular submucosa matrix had a fragile, delicate structure and was difficult to isolate, whereas the FM was much more robust and easier to obtain.

TABLE 9

Comparison of surface area of ovine forestomachs and glandular stomachs

|  | Forestomach | Glandular Stomach |
|---|---|---|
| Volume (mL) | 13,000 | 3,000 |
| Surface Area (cm$^2$) | 2678 | 1014 |
| Typical ECM sheet width (cm) | 15 | 8 |
| Typical ECM sheet length (cm) | 27 | 17 |
| Area of typical ECM sheet (cm$^2$) | 405 | 104 |
| Comments | Easy to separate tissue layers to produce FM, thick and robust ECM | Difficult to separate tissue layers, a thin and friable ECM, which is difficult to produce large intact sheets |

A significant advantage of FM over other known compositions is that large constructs can be produced from a single organ (e.g., the forestomach). For example, for an animal of any age or bodyweight, sheets of FM produced from the forestomach were typically 3-4 times larger than those produced from the glandular stomach, which in turn are typically larger than those which can be produced from the bladder. ECM sheets obtained from tubular organs such as small intestine are limited in width to the circumference of the organ. For example, small intestinal submucosa from market weight pigs is limited to widths of less than 10 cm due the circumference of the small intestine.

Example 11

Thickness of FM Scaffold

Four sheets of FM scaffold were prepared from the forestomachs of four 5-6 month old lambs weighing approximately 25 kg. Thirteen adequately spaced measurements of the thickness of the FM sheet were made in each of the four samples. The results are presented in the Table 10.

TABLE 10

Thickness of FM sheets derived from four 5-6 month old lambs

| Sampled Sheet | Measurements (µm) | | | |
|---|---|---|---|---|
|  | Min | Max | Mean | Number |
| 1 | 252 | 375 | 309 | 13 |
| 2 | 205 | 268 | 230 | 13 |
| 3 | 270 | 452 | 364 | 13 |
| 4 | 299 | 463 | 388 | 13 |

Small intestinal submucosa derived from pigs weighing greater than 180 kg (as indicated in U.S. Pat. No. 5,372,821) is typically only 100 µm thick. The above measurements demonstrate that immature lambs which are less than 20% of the size of a mature pig can provide ECM sheets which are at least three times as thick as that obtained from small intestinal submucosa of a pig. Such thicker scaffolds possess advantageous properties, such as greater strength and longer persistence following implantation in vivo. Thicker FM scaffolds can be produced with increasing age and weight of the animal.

Example 12

Biaxial Strength of FM Scaffold

Samples of 1-ply FM scaffold sheets were laminated using a layer of collagen polymer, as described in Example 3, to give 2-, 3-, 4- and 8-ply laminates. Additionally, forestomach propria-submucosa and glandular stomach submucosa were manually isolated from the forestomach and the glandular stomach, respectively. These 'unprocessed' samples were not exposed to the STOF process described in Example 1.

Ball burst strength provides a measure of a biomaterials resistance to a load when biaxial force is applied. The test is conducted by clamping the test material in a circular orifice and forcing a metal sphere through the centre of the sample until the sample fails, allowing the sphere to pass through. The relative strengths of materials are compared using the force at the point of failure of the material, termed the 'maximum compression load' (Newtons, N). Maximum compression load of a sample will be dependent on the elasticity and strength of the sample, as well as the sample thickness. The ball-burst test determines biaxial strength, whereby forces are equally applied in all directions. In comparison, uniaxial strength (see below) determines load to failure in one direction only.

Figure 9:
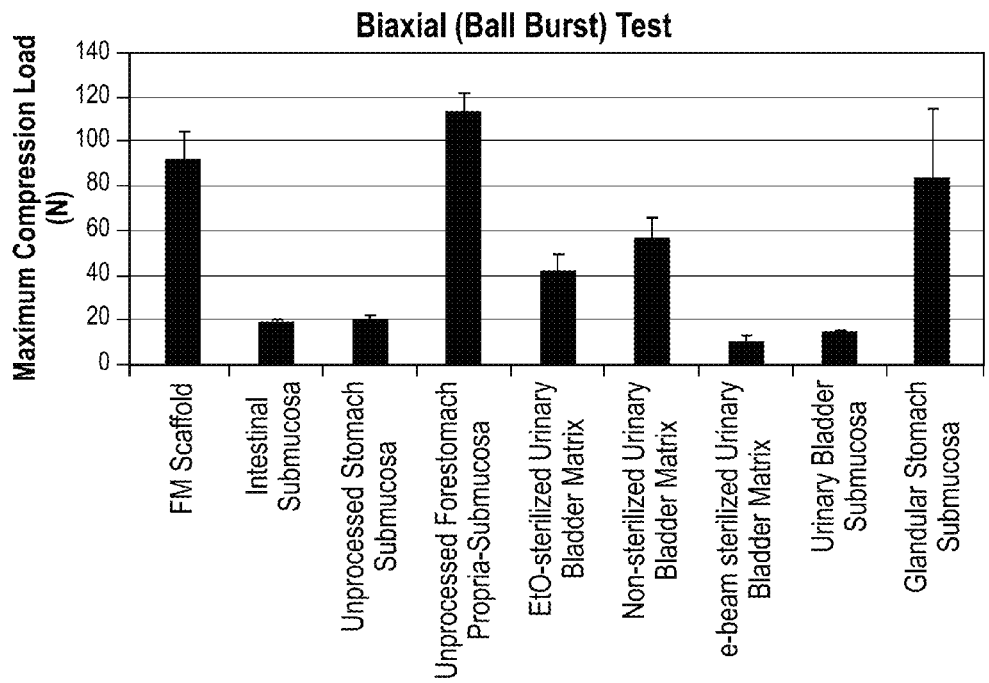
FIG. 9 presents results of the Ball Burst test, showing the relative strength of FM.

In line with the Standard Test Method for Bursting Strength of Knitted Goods, Constant-Rate-of-Traverse (CRT) Ball-Burst Test (ASTM D 3797-89), a 24.5 mm polished steel hemisphere was pushed against the ECM sheets until failure on an Instron 1122 Machine. The maximum compression load was defined as the force required to rupture the sheet. At least six (n=6) samples of each ECM were tested. Results are shown in Table 11 and FIG. 9. FM scaffold was as strong as unprocessed forestomach propria-submucosa (92.8±12.7 and 114.3±8.1 N, respectively) (Table 11 and FIG. 9), and both forestomach ECM materials were substantially stronger than those derived from intestinal tissue, and glandular stomach tissue.

TABLE 11

Comparison of ball burst strength of FM scaffold and other ECM scaffolds

| Scaffold | Maximum Compression Load (N) |
|---|---|
| Ovine FM Scaffold | 92.8 ± 12.7 |
| Porcine Intestinal Submucosa[c] | 20.1 ± 0.5 |
| Ovine Unprocessed Stomach Submucosa | 20.8 ± 1.7 |
| Ovine Unprocessed Forestomach Propria-Submucosa | 114.3 ± 8.1 |
| Porcine EtO-sterilized Urinary Bladder Matrix[a] | 42.2 ± 7.7 |
| Porcine Non-sterilized Urinary Bladder Matrix[b] | 57.3 ± 8.9 |
| Porcine e-beam sterilized Urinary Bladder Matrix | 11.3 ± 1.9 |
| Porcine Urinary Bladder Submucosa[c] | 15.4 ± 0.5 |

[a]Freytes et al., "Effect of Storage Upon Material Properties of Lyophilized Porcine Extracellular Matrix Derived from the Urinary Bladder" (2005) J. Biomed. Mater. Res. B: Appl. Biomater.
[b]Freytes et al., "Uniaxial and Biaxial Properties of Terminally Sterilized Porcine Urinary Bladder Matrix Scaffolds" (2007) J. Biomed. Mater. Res. B: Appl. Biomater.
[c]U.S. Pat. No. 6,099,567

Figure 10:
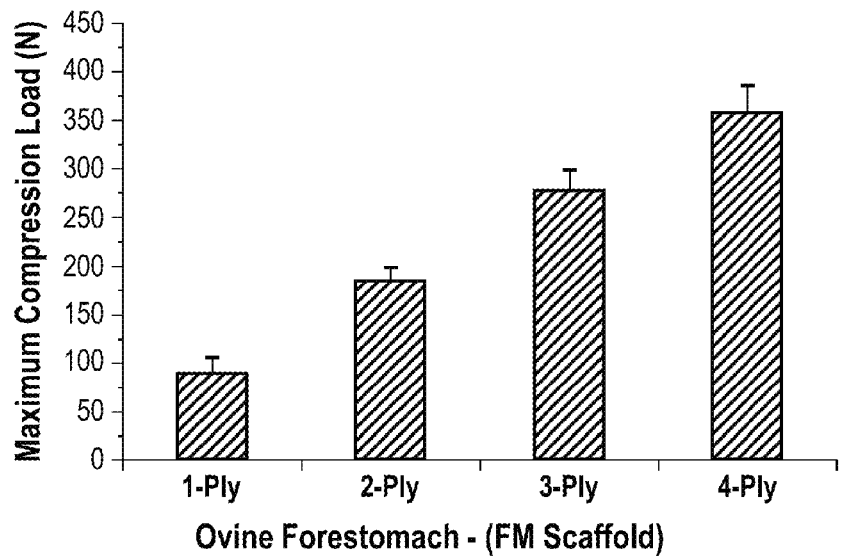
FIG. 10 graphically depicts the ball burst strength of multi-ply ovine FM products. The biaxial strength of single or multi-ply ovine FM products was determined using a Ball Burst Test according to ASTM D 3797-89 "Standard Test Method for Bursting Strength of Knitted Goods, Constant-Rate-of-Traverse (CRT) Ball-burst Test", using an Instron 5800 series electromechanical tester, fitted with a ball-burst compression cage, whereby a 25.4 mm stainless steel ball was pushed against the test material at a feed-rate of 305+/−13 mm/min, until failure. A 1 kN load cell was used to record maximum compression load at failure (N). Error bars represent the standard error of at least five samples.

A dramatic increase in the strength of the FM laminates was observed as additional sheets were laminated to generate a series of multi-ply devices (2-, 3-, and 4-ply). For example, 4-ply ovine FM had a maximum compression load of 361.5±24.9 N, while 1-ply FM had a maximum compression load of (92.8±12.7 N), as shown in FIG. 10.

Figure 11:
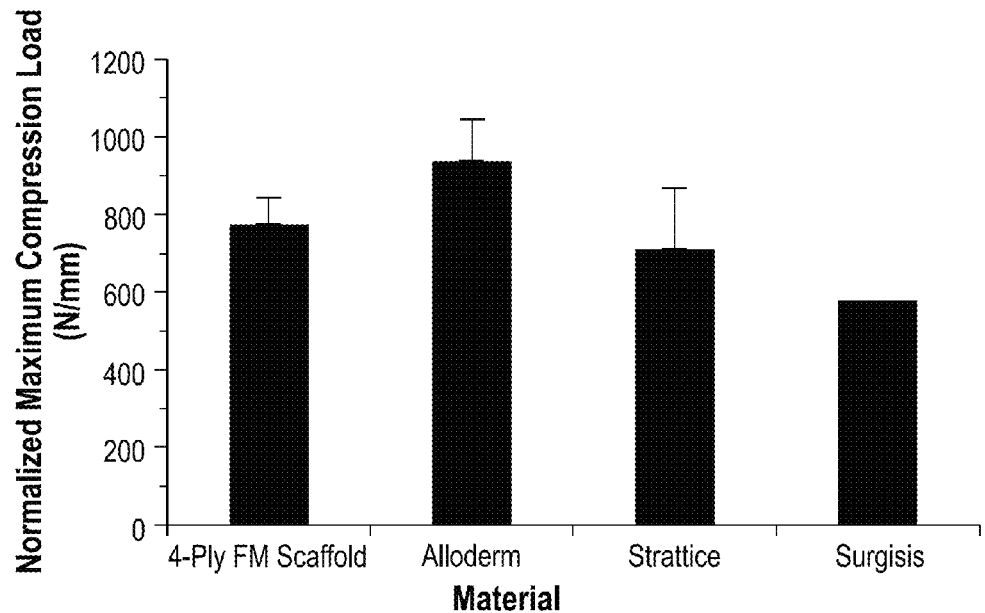
FIG. 11 depicts a comparison of normalized maximum compression load for 4-ply ovine FM and commercially available implant products. Error bars represent the standard error of at least five samples, or from published data.

The biaxial strength of a 4-ply FM laminate was compared with published ball burst data for the commercial ECM-based products, Alloderm™ (LifeCell Corporation), Strattice™ (LifeCell Corporation), and Surgisis™ (Cook Biotechnology) (see Table 12). The 4-ply FM had a lower maximum compression strength than the other implant products. However, in comparing ball-burst strengths it is important to consider also the thickness of the test material, as this dimension will significantly impact the observed maximum compression load. For example, the reported thickness of Alloderm™ was 1.9±0.13 mm, while the 4-ply FM product was approximately 75% thinner at 0.47±0.01 mm. To take into account the different thickness of the ECM products and therefore make a meaningful comparison of the biaxial strengths of the ECM products, the maximum compression load (N) of the products was normalized to their thicknesses (mm). Using this analysis, the relative biaxial strengths of the four products were found to be statistically similar (see Table 12 and FIG. 11).

TABLE 12

Comparison of ball-burst properties of 4-ply FM and commercial ECM-based implant products

| | Maximum Compression Load (N ± SE) | Thickness (mm) | Normalized Maximum Compression Load (N/mm ± SE) |
|---|---|---|---|
| 4-ply FM Scaffold | 361.5 ± 24.9 | 0.47 ± 0.01 | 773.7 ± 68.6 |
| Alloderm ™ (Boguszewski, Dyment et al. 2008) | 1781.5 ± 80.2 | 1.9 ± 0.1 | 937 ± 106.0 |
| Strattice ™ (Boguszewski, Dyment et al. 2008) | 1059.7 ± 181.8 | 1.49 ± 0.07 | 711.2 ± 155.4 |
| Surgisis ™ (package insert) | 440 ± 81 | 0.76 | 578.9 |

Errors represent standard errors from at least five samples, or from published data.
No thickness error reported for Surgisis ™.

Example 13

Uniaxial Tensile Strength

Uniaxial strength measures the one-dimensional force tolerance of a biomaterial whereby a strip of material is clamped at either end and opposing forces are applied. The force at failure of the material is termed the 'maximum load' (N). The maximum load of a sample is dependent on the inherent strength of the test material, as well as the size and thickness of the test sample. Uniaxial testing was performed on an Instron 1122 Machine. Samples were cut to a dog-bone shape with a mid-substance width of 1 cm, as previously described (see Freytes et al., "Effect of Storage Upon Material Properties of Lyophilized Porcine Extracellular Matrix Derived from the Urinary Bladder" (2005) J. Biomed. Mater. Res. B: Appl. Biomater. and Freytes et al., "Uniaxial and Biaxial Properties of Terminally Sterilized Porcine Urinary Bladder Matrix Scaffolds" (2007) J. Biomed. Mater. Res. B: Appl. Biomater., both incorporated herein by reference in their entirety).

FM scaffold was prepared according to Example 1. Additionally, 'unprocessed' forestomach propria-submucosa and stomach submucosa were prepared manually. These unprocessed samples were not exposed to the STOF process. All samples were mounted to the Instron test apparatus and pulled to failure at a constant rate of 20 mm/min. At least eight (n=8) samples of each ECM were tested.

Figure 12:
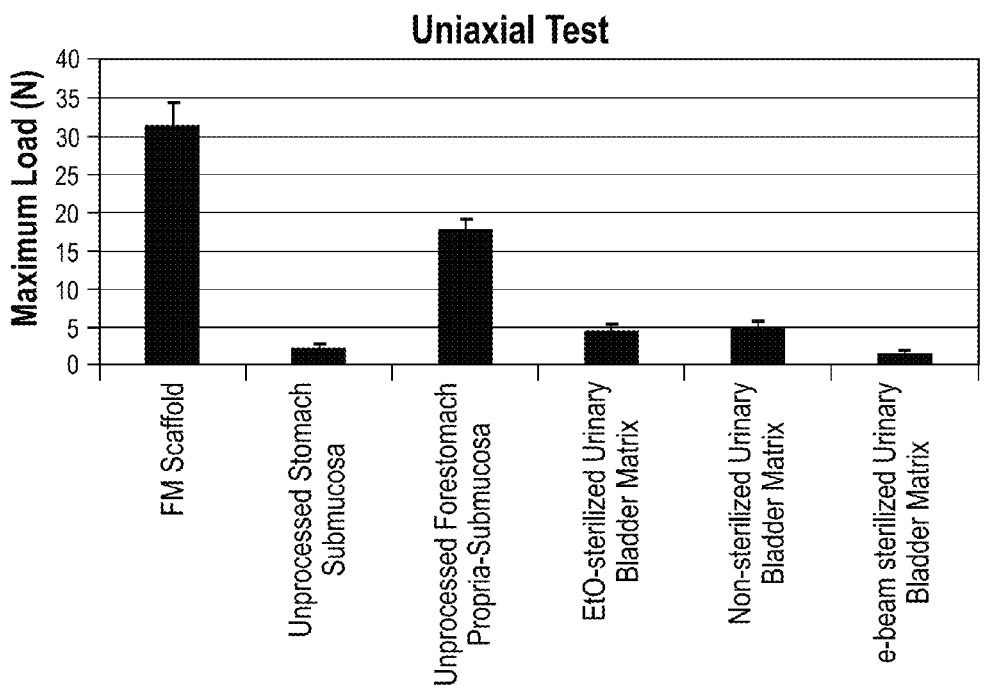
FIG. 12 presents results of the Uniaxial test, showing the relative strength of FM.

The results, as shown in Table 13 and FIG. 12, demonstrated that unprocessed forestomach propria submucosa is much stronger than stomach submucosa from the same animal. Additionally, ovine FM scaffold from six month animals (approx. 25 kg) was stronger than porcine stomach submucosa derived from mature animals (approx. 50 kg), as reported in the U.S. Pat. No. 6,099,567. This data indicates that FM scaffold is much stronger than stomach submucosa, irrespective of the age, and therefore the bodyweight, of the animal. Accordingly, FM is less likely to suffer damage or mechanical failure when used as a single sheet in tissue reinforcement applications relative to stomach-derived ECM. Also, when it is desirable to achieve a composition of high tensile strength by laminating sheets of ECM together it will be appreciated that fewer FM sheets are required compared to other gastrointestinal or urogenital derived ECM scaffolds, making this process simpler and more cost effective.

The inherent strength of FM also makes the use of FM isolated from fetal or neonatal tissue practical, whereas other fetal or neonatal submucosal tissue sources yield tissue which is very weak due to its thinness and immature state.

TABLE 13

Comparison of uniaxial strength of ECM scaffolds

| | Maximum Load (N) |
|---|---|
| Ovine FM Scaffold | 31.6 ± 2.7 |
| Ovine Unprocessed Stomach Submucosa | 2.5 ± 0.4 |
| Ovine Unprocessed Forestomach Propria-Submucosa | 17.9 ± 1.2 |
| Porcine EtO-sterilized Urinary Bladder Matrix[a] | 4.7 ± 0.8 |
| Porcine Non-sterilized Urinary Bladder Matrix[b] | 5.4 ± 0.5 |
| Porcine e-beam sterilized Urinary Bladder Matrix[a] | 1.8 ± 0.2 |

[a]Freytes et al., "Effect of Storage Upon Material Properties of Lyophilized Porcine Extracellular Matrix Derived from the Urinary Bladder" (2005) J. Biomed. Mater. Res. B: Appl. Biomater.
[b]Freytes et al., "Uniaxial and Biaxial Properties of Terminally Sterilized Porcine Urinary Bladder Matrix Scaffolds" (2007) J. Biomed. Mater. Res. B: Appl. Biomater.

In addition to the foregoing data, the maximum uniaxial load for single and multi-ply FM scaffolds was determined, as well as the maximum tangential stiffness (N/mm), elongation at failure (mm), the modulus of elasticity (GPa) and yield stress (MPa). Yield stress is a term normalized to the dimensions of the test sample and can be used to compare similar products of different thicknesses. This term is a measure of the inherent strength of the material. The modulus of elasticity, or Young's modulus is a measure of the elastic potential of the material, that is its ability to be deformed without failure and return to its original state. The modulus of elasticity is an intrinsic property of the material, thus allowing samples of different sizes to be compared. For the modulus of elasticity, a lower number indicates greater elasticity. For example, the modulus of rubber is 0.01-0.1 GPa.

A comparison of the uniaxial strength properties of 1-ply through to 4-ply FM laminates is presented in FIG. 13. As expected, increasing the lamination state and hence thickness of the product significantly improved uniaxial strength and stiffness. However, lamination did not statistically alter the maximum elongation, or modulus of elasticity. This indicates that the process of lamination increases the strength of the product, but does not alter its pliability, suggesting the handling of 1- and multi-ply products would be similar.

Figure 14:
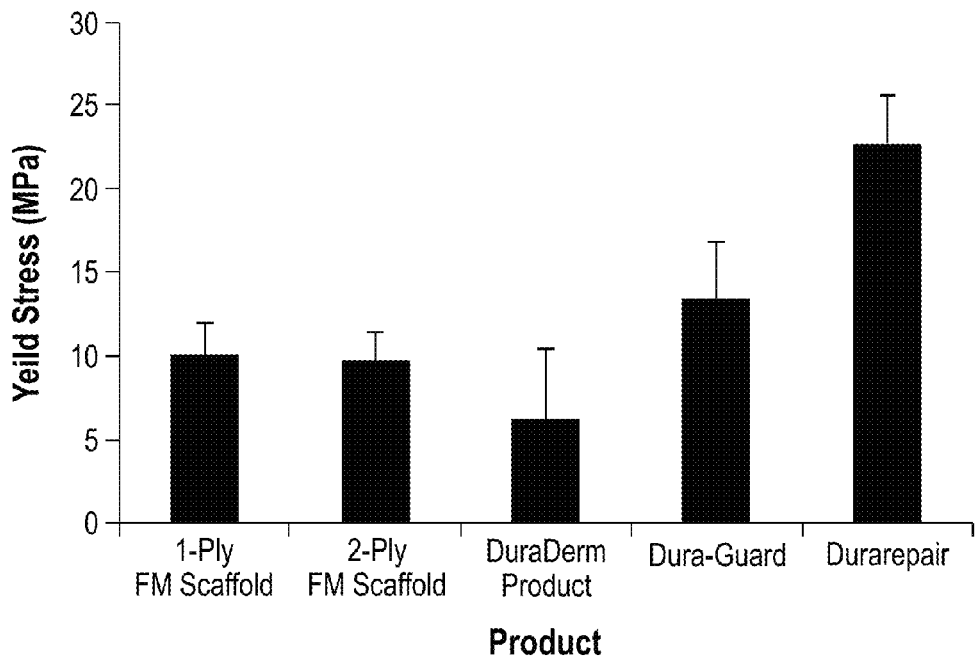
FIG. 14 presents a comparison of the yield stress of 1- and 2-ply ovine FM products with commercial dural repair products. Errors represent standard errors from at least five samples, or from published data.

In order to evaluate the relative uniaxial strength of ovine FM products, a literature survey was performed to identify and extract relevant data relating to the strength of alternate ECM-like products. The uniaxial strength properties and thicknesses of the 1- and 2-ply FM scaffolds were compared with published data for the dural repair products Dura-Guard™ and Durarepair™ (Table 14 and FIG. 14). The 1- and 2-ply FM scaffolds had statistically equivalent yield stress (10.15±1.81 and 9.77±1.68 MPa, respectively). This is expected as yield stress is normalized to the sample thickness, such that two samples prepared from the same material but of different thicknesses should give identical yield stress. The 1- and 2-ply FM products had a similar yield stress to Dura-Guard™ (13.5±3.34 MPa), and all three products out performed DuraDerm™ (6.27±4.20 MPa). Durarepair, the strongest of the products, had a yield stress of 22.7±2.83 MPa. The 1- and 2-ply FM scaffolds (Young's modulus of 0.04±0.01 and 0.05±0.01 GPa, respectively) had better elastic properties than Dura-Guard™ and Durarepair™ (0.08±0.02 and 0.07±0.01 MPa, respectively). DuraDerm™ demonstrated the best elastic potential (modulus 0.002±0.009 GPa), but as noted above, was the weakest of the products surveyed.

This analysis suggests that FM scaffolds have strength and elastic characteristics that are equivalent to or better than current commercial dural repair products. This analysis indicates that a 4-ply FM scaffold has an equivalent strength to commercial dural products.

TABLE 14

Comparison of uniaxial strength properties of 1-ply and 2-ply FM scaffolds with commercial dural repair products

|  | Modulus of Elasticity (Youngs') (GPa ± SE) | Yield Stress (MPa) | Thickness (mm ± SE) |
|---|---|---|---|
| 1-ply FM Scaffold | 0.04 ± 0.01 | 10.15 ± 1.81 | 0.25 ± 0.01 |
| 2-ply FM Scaffold | 0.05 ± 0.01 | 9.77 ± 1.68 | 0.31 ± 0.01 |
| DuraDerm ™ (Sclafani, McCormick et al. 2002) | 0.002 ± 0.009 | 6.27 ± 4.20 | 1.4 ± 0.2 |
| Dura-Guard ™ (Zerris, James et al. 2007) | 0.08 ± 0.02 | 13.5 ± 3.3 | 0.400 ± 0.001 |
| Durarepair ™ (Zerris, James et al. 2007) | 0.07 ± 0.01 | 22.7 ± 2.8 | 0.50 ± 0.02 |

Errors represent standard errors from at least five samples, or published values.

To evaluate the suitability of laminated FM scaffolds for implantation, biophysical properties of the scaffolds, as derived from uniaxial strength testing, were compared with similar published data relating to the commercially available product Alloderm™ (see Table 15). It is apparent from the spread of reported data that a consensus about the true strength and elastic potential of Alloderm™ has not been reached in the literature. This may reflect the cadaveric origins of the product, leading to product irregularities, including the observed variability in thickness. The reported yield stress of Alloderm™ ranges from 7.00±1.00 to 16.79±2.10 MPa. In order to make a meaningful comparison, the midpoint of the data spread was calculated as 11.90 MPa, which is comparable to the yield stress of the 4-ply laminate (11.97±1.16 MPa). The two reported modulus of elasticity for Alloderm™ are an order of magnitude different from each other, making a comparison with the 4-ply product difficult. However, the 4-ply product retains the elastic properties of the 1- and 2-ply products and is similar to those of the dural repair products Dura-Guard™ and Durarepair™ (see discussion above).

Accordingly, the studies performed herein indicate that FM scaffolds have strength characteristics equivalent to the material used to manufacture Alloderm™. In particular, the data indicates that multi-ply FM scaffolds have suitable strength and elastic properties for implant applications, where inherent strength is a requirement of the implant material.

TABLE 15

Comparison of uniaxial strength properties of 4-ply FM scaffold and Alloderm ™

|  | Modulus of Elasticity (Youngs') (GPa ± SE) | Yield Stress (MPa) | Thickness (mm ± SE) |
|---|---|---|---|
| 4-ply FM Scaffold | 0.06 ± 0.01 | 11.97 ± 1.16 | 0.47 ± 0.01 |
| Alloderm ™ (Lerner, Chaikin et al. 1999) | N.D | 16.79 ± 2.10 | N.D |
| Alloderm ™ (Morgan, McIff et al. 2004) | N.D | 10.55 ± 2.37 | 0.9 ± 0.1 |
| Alloderm ™ (Choe, Kothandapani et al. 2001) | N.D | 7.20 ± 2.56 | 1.00 ± 0.05 |
| Alloderm ™ (Vural, McLaughlin et al. 2006) | N.D | 15.25 ± 7.13 | 1.34 ± 0.05 |
| Alloderm ™ (Gouk, Lim et al. 2008) | 0.014 ± 0.0015 | 7 ± 1 | 0.45 ± 0.05 |
| Alloderm ™ (Sclafani, McCormick et al. 2002) | 0.001 ± 0.002 | 8.64 ± 3.31 | 1.89 ± 0.30 |

N.D = no data.
Errors represent standard errors from at least five samples, or published values.

Example 14

Suture Retention Strength

Suture retention testing is a practical clinical consideration that determines the resistance of a biomaterial to suture 'pull-out'. The test protocol is similar to uniaxial strength, however in this example one edge of the test material was clamped, while the other was secured to an opposing clamp via a suture placed through the test material. The suture was secured to the biomaterial at a defined 'bite-depth', that is the distance from the site of the suture to the edge of the test material. Opposing forces were applied at a constant rate until the material failed and the suture was pulled-out of the test material. The load at failure of the material, termed the 'maximum load' (N), is dependent on the inherent strength of the test material, the bite-depth and thickness of the sample.

Figure 15:
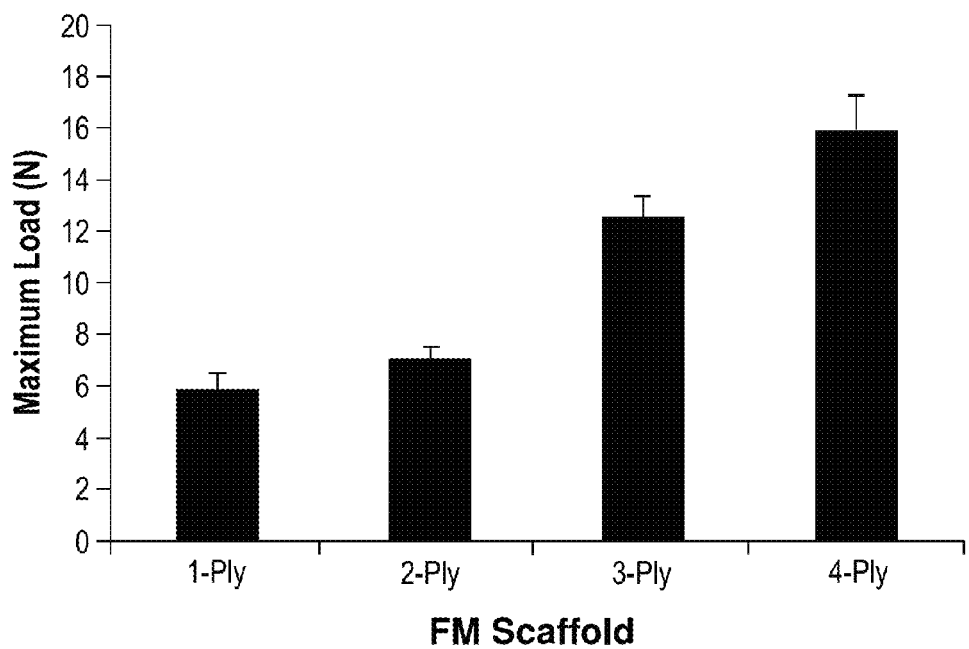
FIG. 15 presents a comparison of the suture retention strength of multi-ply ovine FM products. Samples of multi-ply ovine FM products were tested for suture retention according to ANSI/AAMI VP20-1994 Guidelines for Cardiovascular Implants Vascular Prostheses Measured in Newton's. Sutures were made in 4 cm×2.5 cm samples, using suture with a bite-depth of 2 mm. Load at failure was recorded using a Instron 5800 series electromechanical tester, fitted with a 100 N load cell using an advance rate of 100 mm/min. Load at failure was defined as a 90% reduction in the observed load. The free end of the sample was held in a 25 mm vice grip, while the suture was attached to the opposing clamp via a stainless hook. Error bars represent the standard error of at least six samples.

A series of laminated FM scaffolds were tested for suture retention. As expected, lamination of FM sheets increased the resistance of the product to suture pull-out, as shown in FIG. 15. For example, the load to failure of the 1-ply FM was 5.91±0.60 N, while the stronger (as determined from uniaxial and ball-burst testing, above) 4-ply FM scaffold gave a load to failure of 15.96±1.30 N.

Figure 16:
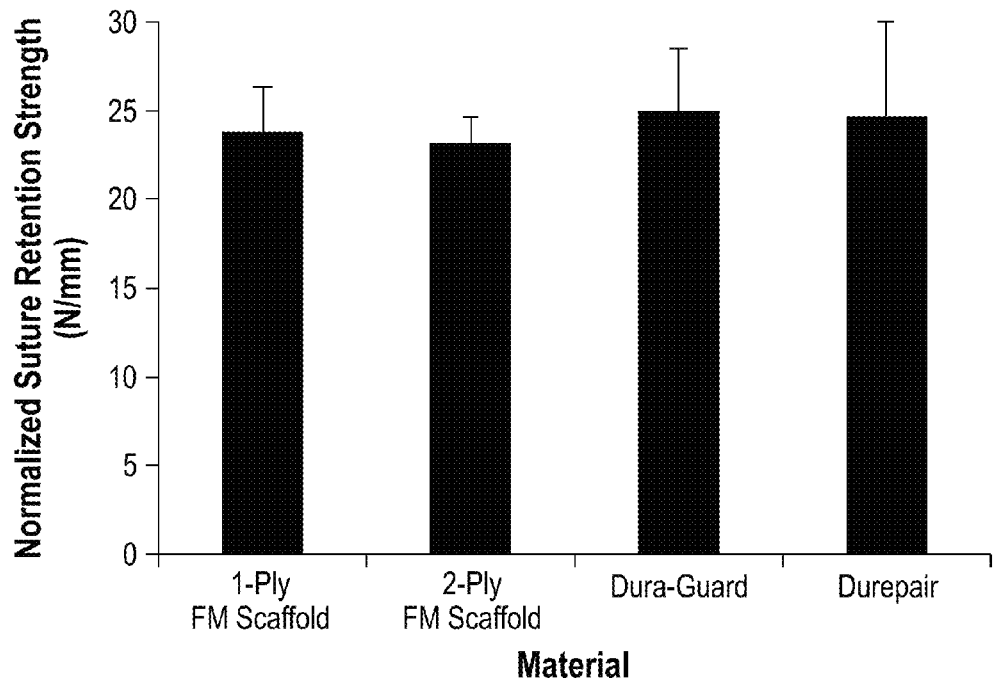
FIG. 16 presents a comparison of the normalized suture retention strength of ovine FM products and dural repair products. Errors represent standard errors from five independant samples, or from published data.

As seen in FIG. 15, observed suture retention strength is dependent on sample thickness. Thus, in order to compare the suture retention strength of ovine FM laminates with commercial products using published data, the maximum load to sample thickness was normalized. A comparative analysis of FM scaffolds and the dural repair products Durarepair™ and Dura-Guard™ is shown in Table 16 and FIG. 16. The suture retention strength of the 1-(4.7±0.4 N) and 2-ply (7.1±0.5 N) FM scaffolds was less than Dura-Guard™ (10.02±1.35 N) and Durarepair™ (12.38±2.10 N). However, taking into account the relative thicknesses of the four products via normalized suture retention, the four products had equivalent potential to resist suture pull-out.

TABLE 16

Comparison of the suture retention strength of FM scaffolds and commercially available dural repair matrices

| | Suture Retention - Maximum Load (N ± SE) | Thickness (mm ± SE) | Normalized Suture Retention (N/mm) |
|---|---|---|---|
| 1-Ply FM Scaffold | 4.7 ± 0.4 | 0.25 ± 0.01 | 18.9 ± 1.5 |
| 2-ply FM Scaffold | 7.1 ± 0.5 | 0.31 ± 0.01 | 23.2 ± 1.6 |
| Dura-Guard ™ (Zerris, James et al. 2007) | 10.02 ± 1.35 | 0.40 ± 0.01 | 25.1 ± 3.4 |
| Durarepair ™ (Zerris, James et al. 2007) | 12.38 ± 2.10 | 0.50 ± 0.02 | 24.76 ± 5.19 |

Errors represent the standard error of five samples, or published data.

Figure 17:
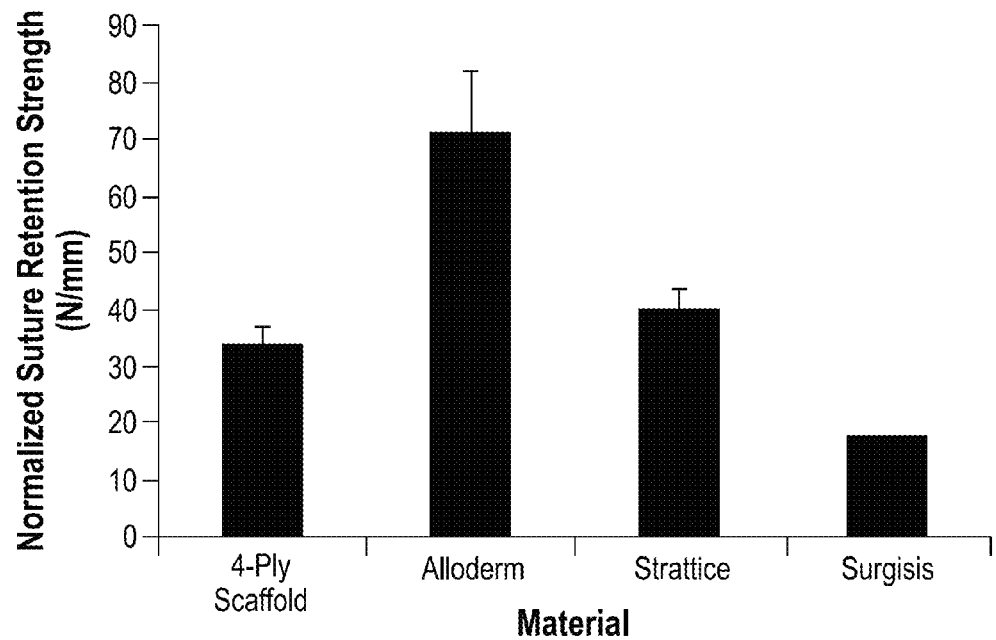
FIG. 17 presents a comparison of the normalized suture retention strength of 4-ply ovine FM product and commercially available implant matrices. Errors represent standard errors from at least five samples, or from published data. No error reported for Surgisis™. Alloderm™ and Strattice™ tested with a bite depth of 10 mm, 4-ply ovine FM and Surgisis™ tested with a bite depth of 2 mm.

The comparative study was extended to determine the performance of laminated FM scaffolds relative to the commercially available implant products Alloderm™, Strattice™ and Surgisis™. The results are shown in Table 17 and FIG. 17. It is important to note that while the ASTM standard for suture retention testing prescribes a 2 mm bite depth, various bite depths were employed across these studies, from about 2 mm to about 10 mm (Table 17). Increasing the bite depth used during testing increases the observed maximum load as more force is required to pull the suture further through the sample until the edge is reached and pullout is observed. The 4-ply FM laminate scaffold was significantly more resistant to suture pull-out than the Surgisis™ product (normalized suture retention strengths, 34.2±2.8 and 18.0 N/mm, respectively). The reported suture retention strengths of both Alloderm™ and Strattice™ have employed a modification to the ASTM standard, using a bite-depth of 10 mm (Table 17). The normalized suture retention strengths of these products was 71.2±10.71 and 40.2±3.43 N/mm, respectively. In comparison, the normalized suture retention strength of the 4-ply FM scaffold was 34.2±2.8 N/mm, using a bite-depth of 2 mm. This data indicates that the suture retention strength of the 4-ply FM scaffold would likely be equivalent to both Alloderm™ and Strattice™ if all three products were tested in side-by-side experiments using equivalent bite-depths. This notion is supported by the observation that 4-ply FM scaffold has similar yield stress under uniaxial testing (see Table 15), and that the three products have similar normalized ball-burst strengths (see Table 12).

TABLE 17

Comparison of the suture retention strength of laminated FM scaffolds and commercially available implant matrices

| | Suture Retention - Maximum Load (N ± SE) | Thickness (mm ± SE) | Normalized Suture Retention (N/mm) | Bite Depth (mm) |
|---|---|---|---|---|
| 4-ply FM Scaffold | 16.0 ± 1.3 | 0.47 ± 0.01 | 34.2 ± 2.8 | 2 |
| Alloderm ™ (Boguszewski, Dyment et al. 2008) | 135.2 ± 11.1 | 1.9 ± 0.13 | 71.2 ± 10.71 | 10 |
| Strattice ™ (Boguszewski, Dyment et al. 2008) | 59.9 ± 2.3 | 1.49 ± 0.07 | 40.2 ± 3.43 | 10 |
| Surgisis ™ (Oasis Product Insert) | 13.7 ± 3.2 | 0.76 | 18.0 | 2 |

Errors represent standard errors from at least five samples, or from published data.
No error reported for Surgisis ™.

Example 15

Hydrostatic Permeability Index (PI) of FM Scaffold

The permeability of implantable ECM scaffolds can influence the rate of cell infiltration and diffusion of molecules into and from the exogenous implant. The desired permeability of the implant will depend on the application. For example, implant devices for dural replacement should generally be relatively impermeable to protect against the potential loss of cerebral spinal fluid. Implants for tissue reconstruction require relatively greater permeability to allow exchange of advantageous growth factors and cell infiltration and release of wound exudate. Thus, ideally, tissue scaffold technologies, such as the one provided by the present invention, allow permeability to be tailored as required by the target application.

In order to assess the extent of aqueous permeability of single and multi-ply ovine FM products, permeability indices (PI) were determined using a hydrostatic permeability test rig, according to established procedures (Freytes, Tullius et al. 2006). Given that the FM scaffold is anisotropic, having faces derived from the epithelial junction and muscle junction, the present study sought to determine if the 1-ply scaffold had differential permeability depending on the direction of flow through the anisotropic material. Differential permeability as a result of the "handedness" of biologically derived ECM has been previously noted. Table 18 compares the permeability of 1-ply FM scaffold with published permeability indices for ECM derived from porcine urinary bladder matrix. The results showed that FM scaffold was permeable to aqueous solutions. Notably, the 1-ply FM scaffold was approximately ten-fold less permeable than the urinary bladder matrix in both directions.

The present study was extended to determine the aqueous permeability of native bovine dura and 1- and 4-ply FM scaffolds. Dura was extracted from an approximately 2 year old cow and the dural membrane tested for permeability using the established procedure. The dura is considered to be a relatively impermeable membrane as it has evolved to protect the mammalian central nervous system from leakage and foreign body insult. The permeability of the dura was similar to the 1-ply FM scaffold (0.0022±0.0003 and 0.0031±0.0005 mL/cm$^2$/min, respectively), while the 4-ply FM scaffold was approximately 10-fold less permeable 0.00010±0.00001 mL/cm$^2$/min). Thus, the 1-ply scaffold provides the advantage of having a permeability very similar to native dura. The difference between the 2-ply and 4-ply FM scaffolds likely reflects a property of the polymer used to laminate the sheets. Thus, subsequent laminate products could be developed with 'tailored' permeability, a feature that would be particularly relevant to dural implant products.

TABLE 18

Permeability indices of the 1- and 4-ply FM scaffolds, compared with urinary bladder matrix and bovine dura

| | Permeability Index (mL/cm²/min) | | |
|---|---|---|---|
| | luminal→abluminal | abluminal→luminal | ratio |
| 1-ply FM scaffold | 0.0031 ± 0.0005 | 0.0025 ± 0.0006 | 1.23 |
| urinary bladder matrix (Freytes, Tullius et al. 2008) | 0.08 ± 0.03 | 0.02 ± 0.08 | 4.00 |
| 4-ply FM Scaffold | | 0.00010 ± 0.00001 | N.A |
| Bovine Dura | | 0.0022 ± 0.0003 | N.A |

Errors represent standard errors form at least five samples or from published data.
N.A. = not applicable.

Example 16

In Vivo Efficacy of FM Scaffold in a Rodent Model of Wound Healing

The following study was performed to show the efficacy of FM in wound healing. Forestomach matrix prepared from a 1 week old calf was cut into elliptical implants (25×12 mm). Twelve male Lewis rats aged between 20-23 weeks with an average weight of 370 g were obtained. The skin of the rats was disinfected with 0.5% chlorhexidine and 70% ethanol. A full thickness wound was created with a sterile 12 mm biopsy punch after measuring the cranial edge to be 6 cm from the base of the skull along the spinal axis. The matrix was implanted so that it covered the wound and extended subcutaneously beneath the skin at the cranial margin. Sterile PBS was used to re-hydrate the matrix and the wound was covered with Intrasite Gel (Smith and Nephew). Six similarly wounded rats were treated with sterile saline as a control. In the first 4 days of the experiment the rats treated with FM had a more rapid rate of closure compared with the controls. After this time, the healing rate of the FM wound was slower compared to the controls, presumably because the scaffold reduced the degree of wound contraction. By 23 days the FM treated wounds and the control untreated wounds were less than 20% of the original size. There was no evidence of inflammatory or immune reaction to the FM in the wound or in the region of the subcutaneous implant.

Example 17

In Vivo Efficacy of FM Scaffold in a Porcine Model of Wound Healing

In order to further evaluate the in vivo performance of an FM scaffold, and to determine its effectiveness in stimulating tissue regeneration and ability to undergo remodeling, a comprehensive wound healing study in a porcine model system was conducted. The porcine wound healing model is generally considered to be an accepted animal model to study the wound healing process and the effectiveness of clinical or therapeutic interventions (Lindblad 2008). This is because healing of the porcine dermis most resembles the healing process in humans. For example, wound contracture is the dominant mechanism of wound closure in rodents, while in pigs and humans wound closure predominantly occurs via infill of the tissue deficit (Lindblad 2008).

Figure 18:
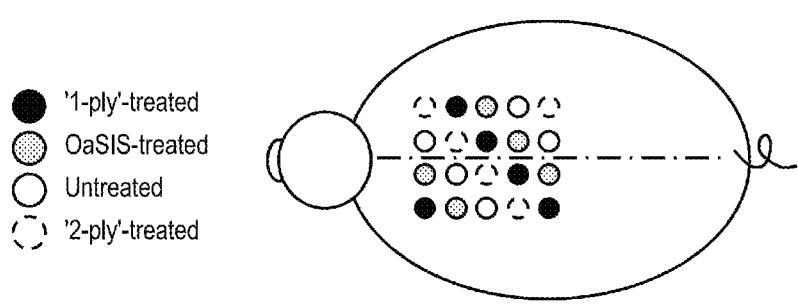
FIG. 18 presents an example of the layout of full-thickness excisional wounds made to the back of a pig in a porcine wound-healing study.

It is important to note that while the current study focused on an acute porcine model of wound healing, the FM scaffold of the present invention may be used for both acute and chronic indications. The study proceeded as follows. On day 0, a total of 20 full thickness 20 mm diameter wounds were surgically created on the back of a 6 week old anaesthetised female pig (approx. 18-20 kg) using a dermal punch. The wounds were created in four columns of 5 rows, spaced 3 cm apart, as shown in FIG. 18. A total of five animals were used in the study (100 total wound sites).

Each of the wounds was either untreated, or treated with either sterile 1-ply FM, 2-ply laminated FM, or the established ECM-based product, SIS. In each case a circular piece of one of the foregoing scaffolds (20 mm diameter) was applied to the wound and rehydrated in situ by the application of sterile saline. In order to average any positional bias, the location of the four treatments was changed between each animal, such that no two animals received the same treatment layout. Treated and untreated wounds were dressed identically.

On days 0, 3, 7, 14, 28 and 42 all wounds were digitally imaged and the wound area and depth (height, if appropriate) were recorded. Additionally, a single row of wounds from each animal was biopsied. The biopsy was surgically excised and included the wound bed as well as a portion of normal tissue from the wound margins. All biopsies were formalin fixed, mounted, sectioned and stained for analysis. Sectioned tissues were stained with H&E, Verhoff von Gieson, and Gomori's trichrome stains. Tissues were also stained using immunohistochemistry with markers of cell differentiation, endothelialisation and immune response.

(A) The FM scaffold is Remodeled and Infiltrated with Cells During Wound Healing An examination of fixed tissue biopsies taken during the course of the study indicated that the FM scaffold was infiltrated by cells during the healing process. ECM matrices appeared as green ribbons in Gomori's trichrome stained sections, and the ECM matrices were especially prominent at day 7. Cells were clearly visible within the exogenous ECM scaffold at day 7. Both the FM scaffold matrices and the commercial product SIS were visible for approximately 14-28 days, after which time the matrices were fully degraded and mature collagen was laid down in a process of remodeling.

(B) Persistence of the FM Scaffold in Treated Wounds

The persistence of FM scaffolds in the porcine wound healing model was evaluated. In order to qualitate the persistence of the ECM treatments in the healing wounds, Verhoff van Gieson (elastin) stained tissue sections were examined for the appearance of the matrix, or matrix fragments, in each. In elastin-stained sections, scaffolds (1- and 2-ply FM or SIS) appeared as a red-to-black ribbon that could clearly be distinguished from the regenerating wound. The persistence of scaffolds at the time points sampled is summarized in FIG. 19.

At earlier time points (days 3 and 7), scaffold was clearly visible in the top ⅓ of the wound, typically in association with the regenerating epithelium and/or crust. As the time course progressed, the scaffold appeared to be migrating into the wound bed and undergoing degradation. There was little difference in the longevity of the three scaffold treatments, such that by day 14-28 scaffold was absent from the majority of wounds. No matrix was visible by day 42.

(C) The FM Scaffold Promotes Cell Proliferation within Regenerating Wounds to a Greater Extent than Matrix Derived from Small Intestine Submucosa Cell proliferation within the regenerating wound can be a useful indicator of the effectiveness of a wound treatment, as cell proliferation is indicative of a beneficial immune response, and of fibroblast and/or keratinocyte migration and proliferation. In order to quantify cell proliferation, immunohistochemistry of biopsied tissue obtained during the porcine wound healing study described above was conducted using the cell marker Ki67. Ki67 is expressed during all active phases of the cell cycle, and is therefore a useful marker of cell proliferation and cellular activity. Ki67 is not expressed in resting cells.

Formalin fixed biopsy tissues were mounted in paraffin and sectioned at 15 μm before being subjected to citrate buffer epitope retrieval. Active cells were then detected using a Ki67 primary antibody at 1:50 dilution, and staining was developed using HRP-conjugated secondary antibody and DAB via a Bond Max™ Automated IHC/ISH Staining System (Leica Microsystems Instruments). Sections were then lightly counterstained with Mayer's haematoxylin. Immuno-stained slides were digitally imaged at 40× magnification, with three random fields taken from the epithelial layer (days 3, 7, 14, 28 and 42), and three images taken from the regenerating dermal layer (days 7, 14, 28 and 42). Using ImageJ software (National Institute of Health), images were processed to quantify the number of Ki67-positive cells per frame. Firstly, images were deconvoluted to separate the brown DAB staining from the other color components present in the image, then background was subtracted via the threshold function. Ki67-positive cells were identified as black clusters with a size range of 300-4500 pixels, and counted accordingly.

Figures 19, 20:
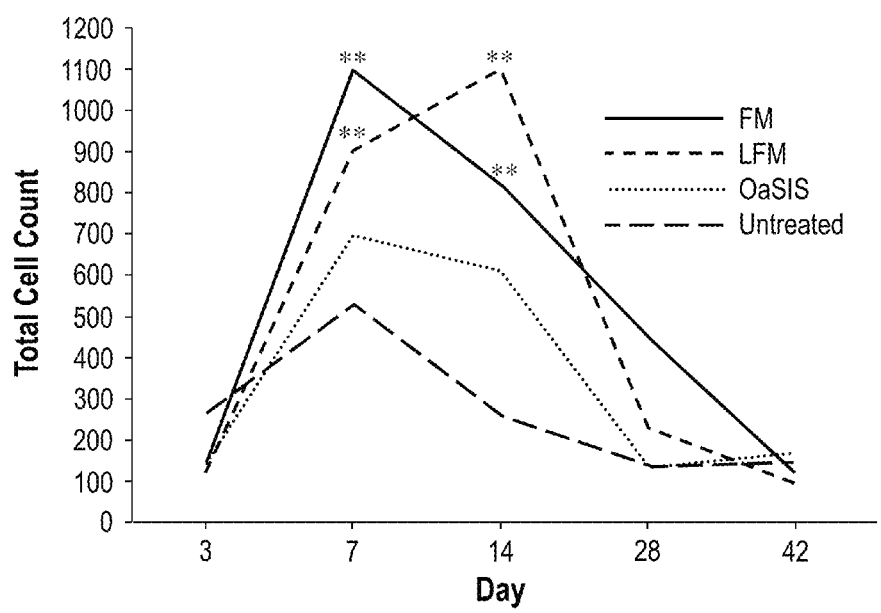
FIG. 19 presents the persistence of ECM scaffolds in tissue biopsies taken during the course of the wound healing study.
FIG. 20 graphically depicts quantification of cell proliferation during wound healing. Wounded tissue was treated with ovine FM (1-ply, 2-ply), SIS, or was untreated, and the total number of Ki67-positive cells in three 40× frames taken from the epithelial layer and three 40× frames taken from the regenerating dermal layer were counted using IHC and digital methods. **$P<0.01$ significance relative to untreated control using one-way ANOVA.

The quantification of cell proliferation is shown in FIG. 20, expressed as the total number of Ki67-positive cells identified in the three epithelial frames and the three dermal frames per tissue section. Each of the four treatment groups were sampled at the days indicated. Ki67-positive cells in the dermal layer were not quantified on day 3 due to the absence of a dermal layer. Generally, dermal cell proliferation spiked on days 7 and 14 for all four treatment groups. On both days 7 and 14, the FM scaffold treated wounds had significantly greater cell proliferation than SIS-treated and untreated groups (see FIG. 20; $P<0.01$ one-way ANOVA using GraphPad Prism). This proliferative phase resolved over time with Ki67-positive cells returning to 'baseline' on day 42 in all treatment groups.

(D) The FM Scaffold Increases Vascularization of Healing Wounds Relative to Scaffold Derived from Small Intestine Submucosa The presence of a functional blood supply within a wound is critical to wound closure and healing. As such, increasing the vascularity of a healing wound has received considerable attention as a means of improving wound healing rates and the quality of wound healing, especially in chronic wounds. The extent of vascularization (e.g., angiogenesis) following treatment with ovine FM scaffold and small intestine submucosa scaffold was determined in the context of the porcine wound healing model described above. In order to quantify the extent of endothelialisation and the development of vasculature in the healing wounds, immunohistochemistry coupled with digital quantification methods were employed. Fixed biopsy tissues were sectioned at 15 μm, mounted and subjected to EDTA-bufferered surfactant. Endothelial cells were stained with an anti-CD34 antibody at 1:100 dilution and visualised using an HRP-conjugated secondary antibody and DAB staining, before light counterstaining with Mayer's Haemotoxylin. Tissue biopsies taken at day 3 were excluded from this analysis given the absence of a clearly defined dermal layer. Stained slides were digitally imaged at 40× magnification by recording four randomly selected frames of the regenerating dermal layer of each of the tissue sections. Using ImageJ software, the DAB color channel (CD34-positve cells) was deconvoluted from each of the images. The monochrome brown images were filtered to remove smaller non-specifically stained particles and small CD34-positive clusters not representative of blood vessels ($<300$ μm$^2$). The number of blood vessels was then counted using the following criteria; 'small vessels'=300-500 μm$^2$, 'medium vessels'=500-1500 μm$^2$ and 'large vessels'>1500 μm$^2$.

Figure 21A:
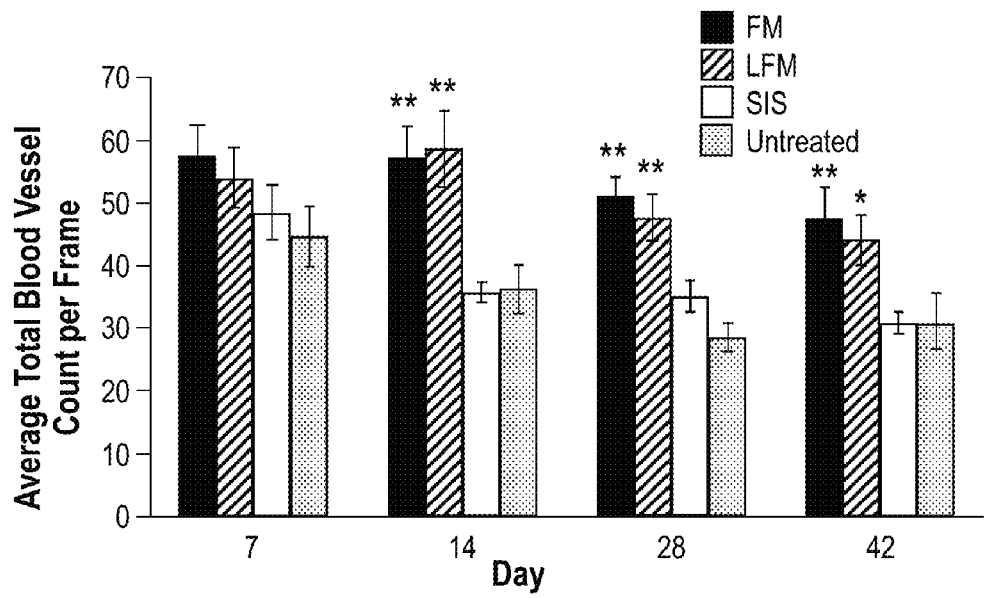
FIG. 21 graphically depicts a quantification of blood vessels in wounded tissue treated with ovine FM (1-ply and 2-ply), SIS, or wounded tissue that was untreated. (A) depicts the average total number of blood vessels counted per frame, analyzed for each tissue biopsy. Error bars represent standard errors from the 20 biopsies analyzed for each treatment group at the time points indicated. **$P<0.01$ and *$P<0.05$ significance relative to untreated control using one-way ANOVA. (B) depicts the number of blood vessels (small, medium and large) as a proportion of total observed blood vessels for each of the treatments, at the time points indicated. (C) depicts the average number of small blood vessels (300-500 µm$^2$), counted per frame. Counts were averaged over all frames analyzed from the five animals under study. Error bars represent standard errors from 20 analyzed frames for each of the treatment groups, at the time points indicated. (D) depicts the average number of medium blood vessels (500-1500 µm$^2$), counted per frame. Counts were averaged over all frames analyzed from the five animals under study. Error bars represent standard errors from 20 analyzed frames for each of the treatment groups at the time points indicated. (E) depicts the average number of large blood vessels, (>1500 µm$^2$) counted per frame. Counts were averaged over all frames analyzed from the five animals under study. Error bars represent standard errors from 20 analyzed frames for each of the treatment groups, at the time points indicated.

The average total number of vessels counted per frame is shown in FIG. 21A, for each of the four treatment groups over the course of the experiment (day 3 excluded). There was a statistically significant increase in the number of blood vessels in wounds treated with either of the ovine FM scaffolds, relative to untreated wounds. The increase in total blood vessels relative to untreated wounds was evident on days 14 ($P<0.01$ 1-ply FM and 2-ply FM), 28 ($P<0.01$ 1-ply FM and 2-ply FM) and 42 ($P<0.01$ 1-ply FM and $P<0.05$ 2-ply FM). In comparison, SIS treatment did not increase the total number of blood vessels relative to the untreated control.

Figure 21B:
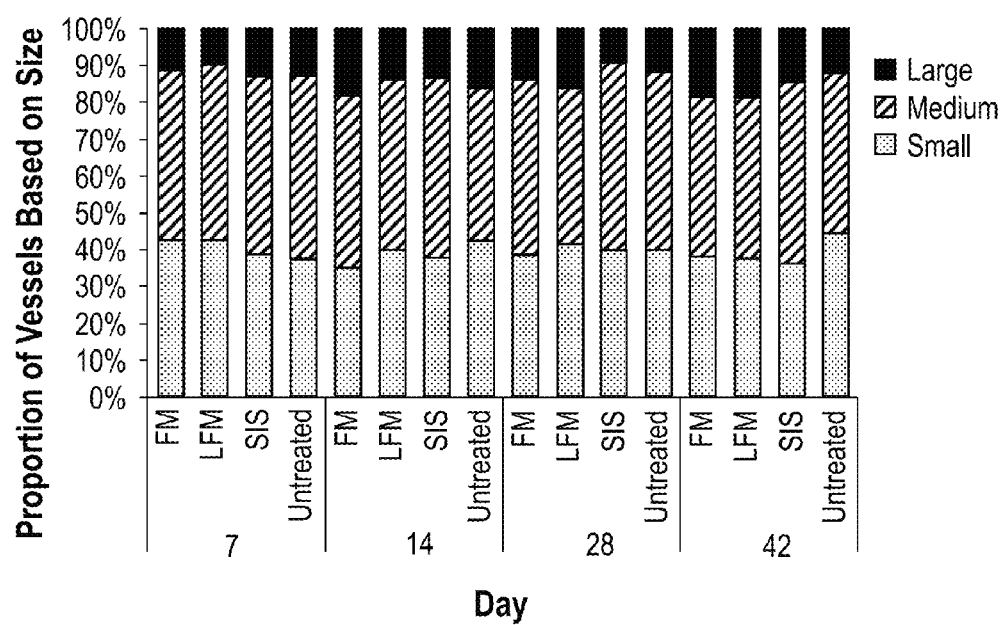
Figure 21C:
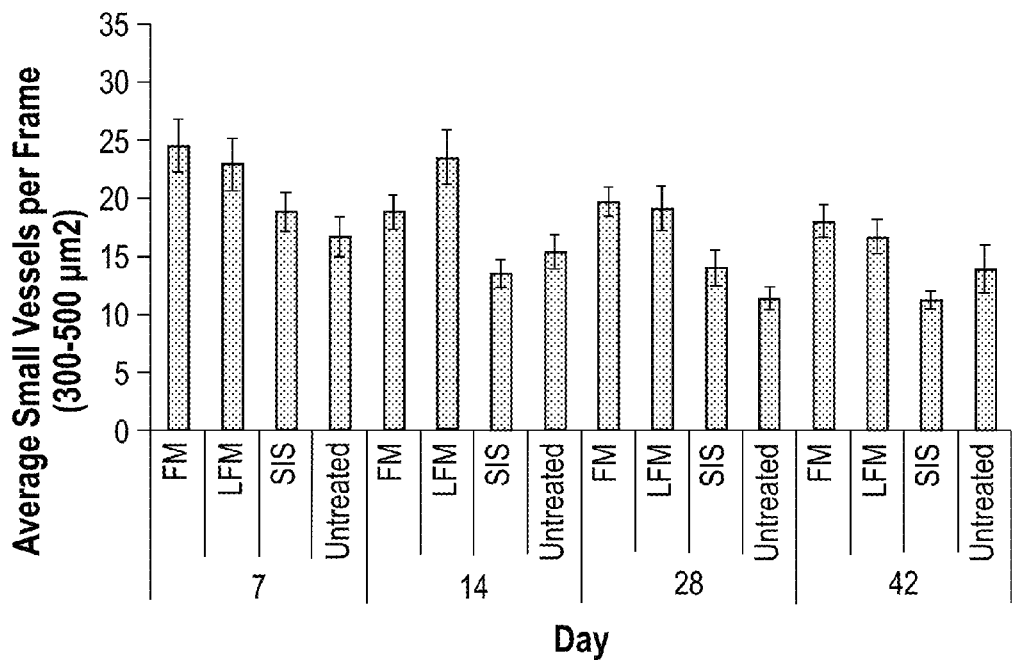
Figure 21D:
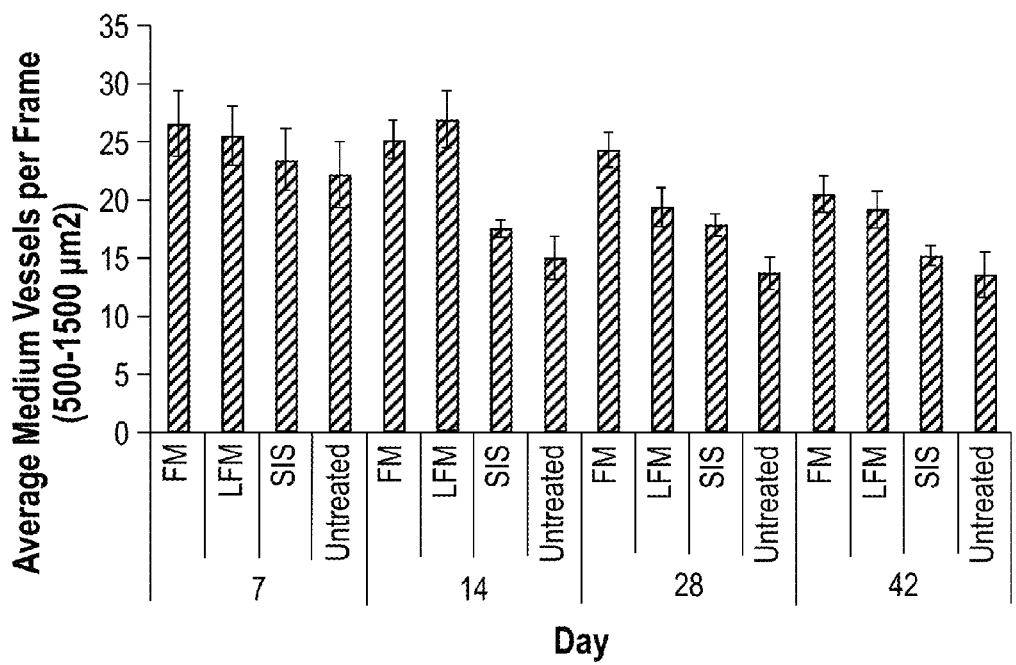
Figure 21E:
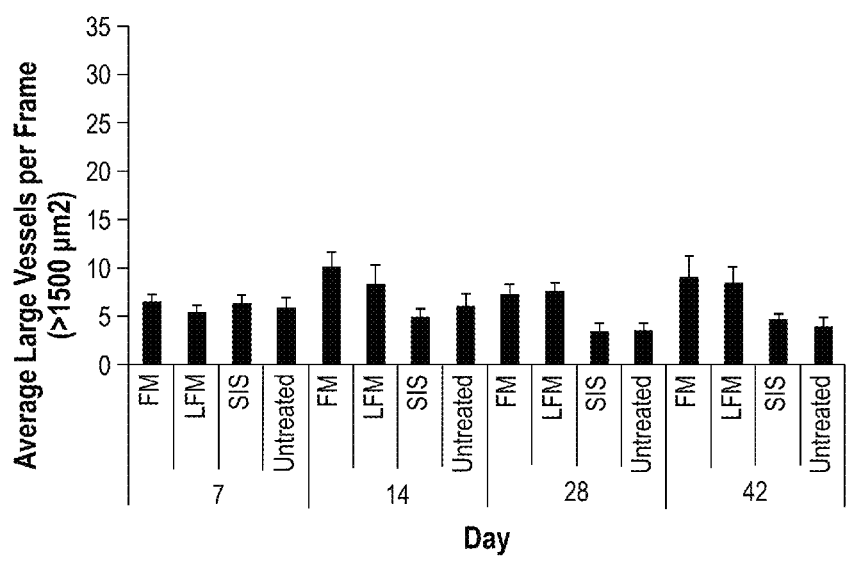

The number of small vessels resulting from treatment with either of the ovine FM scaffolds was higher than that resulting from treatment with SIS, or from untreated groups at day 7, and this trend progressed throughout the course of the experiment (FIG. 21C). The number of medium- and large-sized blood vessels was approximately equal among the four treatment groups at day 7 of the time course (FIGS. 21D and 21E). Ovine FM-based treatments differed from SIS and untreated wounds at days 14, 28 and 42 by having a greater number of medium and large vessels. For example, on day 42, ovine FM scaffold treatments had approximately double the number of large vessels relative to SIS-treated and untreated wounds (FIG. 21E).

By quantifying the numbers of small, medium and large vessels it was possible to understand the effect of the four treatment groups on the relative size distribution of the resulting vessels. The proportions of small (~40%), medium (~45%) and large (~15%) vessels did not change between the four treatment groups over the time course (FIG. 21B). These findings indicate that ovine forestomach matrix treatments increase the total number of vessels, but treatments do not influence the relative size distribution of the vessels formed.

Example 18

Laminated Bioactive FM Scaffolds

Laminated FM scaffolds were developed that include an adhesive polymer, as described above. The polymer binds adjacent sheets of FM scaffold to form a laminated sheet. This polymer can also serve as a vehicle for the delivery of bioactive molecules, and can be used to tune the release of bioactive molecules at the site of tissue contact, as described herein. FM scaffold laminates were prepared which contained one of the following bioactive agents in the polymer layer: growth factors FGF2 or nerve growth factor (NGF), or antimicrobials doxycycline, amoxicillin and poly-L-lysine. FM scaffold laminates containing the bioactive polymer layer were subsequently assayed to demonstrate the bioactivity of the laminate.

Specifically, a collagen gel was prepared as described in Example 3. Once formed the gel was spiked with either human recombinant FGF2 or NGF. Sterile FM scaffold sheets were cut to 8 mm discs, and growth factor spiked collagen gel (10 μL) was applied to one surface. A second FM scaffold disc was applied to the collagen layer to create a laminate sandwich (i.e., FM scaffold/bioactive collagen polymer/FM scaffold). The bioactive FM scaffold laminates were dehydrated at 25° C. for 2 hours to yield a bonded laminate. The FM laminates were produced with FGF2 or NGF at either 0, 250 or 500 ng/disc. The bioactive FM scaffolds were incubated at 37° C. for 24 hours in DMEM (1 mL) to extract the bound growth factor prior to application to a cell monolayer. PC12 cells were seeded onto 24-well plates at 20 k cells/well in DMEM (1 mL) and incubated for 24 hours at 37° C. Media was removed from the cells and replaced with DMEM (1 mL) that had been incubated with the bioactive FM scaffold laminates. Positive control cells were treated with a solution of either FGF2 or NGF at 50 ng/mL final concentration. Cells were incubated for 48 hours. After this time, the cell monolayer was imaged (three frames per well) using an inverted microscope. Total cells were counted per frame, as well as the total number of cell processes per frame. Cell processes are indicative of cell differentiation as stimulated by exogenous growth factors. Cell processes were defined as cellular extensions from the cell body having a length twice that of the width of the cell body. Growth factor stimulated cell differentiation was expressed as the number of cell processes per cell per frame. Results are expressed as Table 19. Both the NGF and FGF2 spiked laminates elicited a cellular response from PC12 cells. Additionally, the response was dose-dependent, such that cellular response of laminates spiked with 500 ng of growth factor (FGF2 or NGF) was higher than laminates spiked with 250 ng.

TABLE 19

Quantification of the bioactivity of FGF2 and NGF containing FM scaffold laminates

| | FGF2 Spiked Laminate (ng/disc) | | | rhFGF2 control |
|---|---|---|---|---|
| | 500 | 250 | 0 | (50 ng/disc) |
| Relative cell response | 0.60 ± 0.01 | 0.39 ± 0.02 | 0.09 ± 0.02 | 0.72 ± 0.02 |

| | NGF Spiked Laminate (ng/disc) | | | rhNGF control |
|---|---|---|---|---|
| | 500 | 250 | 0 | (50 ng/disc) |
| Relative cell response | 0.59 ± 0.04 | 0.41 ± 0.02 | 0.11 ± 0.02 | 0.73 ± 0.01 |

Error represent standard error from at least 6 samples

Discs of FM scaffold laminates were also prepared containing either the anti-microbial small molecule doxycycline or the polymer poly-L-lysine, as described above by spiking a collagen gel with the required bioactive. Doxycycline spiked discs were prepared with final concentrations of 30, 15, 5, 2.5, 1 and 0 µg/disc, while poly-L-lysine spiked discs were prepared a 5, 2, 1, 0.5, 0.1 and 0 µg/disc. Positive controls were prepared by spotting a solution of either Doxycycline (final concentration 30 µg/disc) or poly-L-lysine (final concentration 5 µg/disc) onto sterile filter paper discs. Plates of Mueller-Hinton agar were prepared and streaked with 100 µL of $10^8$ S. aureus and left to dry for 5-10 minutes. Using sterile technique, discs were transferred to the plates and the plates incubated for 24 hours at 35° C. After 24 hours, plates were digitally imaged and the anti-microbial zone of inhibition around each of the discs was scored relative to the positive control. Bioactivity against S. aureus of the laminated FM scaffolds is given in Table 20. Bioactivity of the test articles were scored, where '+++' indicates a bioactivity comparable to the positive control, and '−' indicates no bioactivity.

TABLE 20

Bioactivity against S. aureus of FM scaffolds laminated with either Doxycycline or poly-L-lysine

| | Antibiotic concentration | | | | | | Positive control |
|---|---|---|---|---|---|---|---|
| Doxycycline | | | | | | | |
| µg/disc | 30 | 15 | 5 | 2.5 | 1 | 0 | 30 |
| Antibacterial score | +++ | +++ | ++ | + | − | − | +++ |
| Poly-L-lysine | | | | | | | |
| µg/disc | 5 | 2 | 1 | 0.5 | 0.1 | 0 | 5 |
| Antibacterial score | +++ | − | − | − | − | − | +++ |

Discs of FM scaffold previously laminated with a collagen polymer containing doxycycline were bioactive against cultures of S. aureus. Bioactivity of the doxycycline laminated FM scaffolds were concentration dependant such that laminated discs at 30 µg/disc had approximately equivalent bioactivity to the control discs, while laminates at 1 and 0 µg/disc demonstrated no bioactivity. Bioactivity of FM scaffold laminate containing poly-L-lysine was less pronounced than doxycycline FM scaffold laminates. However, bioactivity was observed at the highest concentration tested of poly-L-lysine (5 µg/disc), which compared well with the control disc.

Results of these in vitro studies demonstrated the ability of growth factor proteins or anti-microbial small molecules and polymers to diffuse with time from the polymeric adhesive layer. Thus, the results indicate that a laminated FM sheet which contains a polymer layer comprising a bioactive agent may be used for a variety of treatment purposes. The laminate can range from 2-ply to 15-ply or more (e.g., 2 to 30-ply) depending on specific clinical applications and hence the required extent of physical performance.

In vivo, the bioactive FM scaffold laminate similarly diffuses bioactive agent from the polymer layer to surrounding tissues. By varying the type of polymer layer and the formulation of the bioactive agent within this layer, the diffusion of bioactive agent from the laminate to local tissue can be controlled.

Example 19

Biocompatibility of Ovine FM Scaffolds

Ovine FM scaffolds were prepared according to Example 1, cut to 4×4 cm square devices and terminally sterilized using ethylene oxide. FM scaffold devices were tested for biocompatibility according to Blue Book Memorandum G95-1 and ISO10993-1:2003. Testing included cytotoxicity, sensitization and irritation/intracutaneous reactivity. In an effort to detect any microbial infection resulting from the FM scaffold device, and/or detect any immunological or inflammatory response, the required testing was expanded to include a 30-day in vivo implantation assay. Endotoxin concentrations of the devices were also quantified.

All devices and controls were prepared according to ISO10993-12:2007 'Biological Evaluation of Medical Devices, Part 12: Sample Preparation and Reference Materials'. The results of biocompatibility testing are summarized in Table 21, and indicate that the biocompatibility characteristics of FM scaffolds make them suitable for in vivo delivery.

TABLE 21

Biocompatibility testing of FM scaffold

| Biocompatibility test | Test description | Result |
|---|---|---|
| Cytotoxicity | Cytotoxicity Test Using the ISO Elution Method in a L-929 Mouse Fibroblast Cell Line according to ISO 10993-5: 1999 'Biological Evaluation of Medical Devices, Part 5: Tests for In Vitro Cytotoxicity' | Non-cytotoxic |
| Cytotoxicity | Agar Overlay according to ISO 10993-5: 1999 'Biological Evaluation of Medical Devices, Part 5: Tests for In Vitro Cytotoxicity' | Non-cytotoxic |
| Irritation | ISO 10993-10: 2002, Amendment 1: 2006, 'Biological Evaluation of Medical Devices, Part 10; Tests for Irritation and Delayed-Type Hypersensitivity' | Non-irritating |
| Sensitization | According to ISO 10993-10: 2002, Amendment 1: 2006, 'Biological Evaluation of Medical Devices, Part 10; Tests for Irritation and Delayed-Type Hypersensitivity' | Non-sensitizing |
| 30 day Implantation | According to ISO10993-6: 1994 'Biological Evaluation of Medical Devices, Part 6: Tests for Local Effects After Implantation' | Non-irritating |
| Endotoxin Testing | USP<85>, ANSI/AAMI ST72: 2002 and FDA guidelines | Passed | samples representing two different stages of the manufacturing process, and subjecting these spiked samples to a treatment analogous to the corresponding manufacturing step. The level of virus inactivation during each treatment was determined by comparing the viral titres recovered from the spiked samples after each treatment, with viral recovery from untreated samples.

The model viruses were chosen to include viruses with different physio-chemical characteristics, such as the presence or absence of envelope, type of nucleic acid genome (DNA or RNA) and survival in the environment/resistance to disinfection (Table 22). The amount of infectious virus present in samples was determined by end-point titration and viral titres were expressed as tissue culture infective dose, 50% ($TCID_{50}$).

The model systems employed in this study demonstrated that both STOF and PAA treatments inactivated the model viruses, with a total theoretical reduction in viral titer of more than 6 logs $TCID_{50}$ (Table 22).

The detergent treatment was effective at inactivating enveloped viruses (PI-3 and FHV-1), but showed little effect at inactivating the non-enveloped virus BEV. This result was expected, as non-enveloped viruses are typically not affected by treatment with detergents. In contrast, PAA treatment was effective at inactivating all three model viruses (Table 22).

TABLE 22

Demonstrated and theoretical inactivation of three model viruses during the scaled-down manufacturing process of FM scaffold

| Virus (family) | Natural host | Genome | Envelope | Resistance | STOF inactivation (log $TCID_{50}$)* | PAA** Inactivation (log $TCID_{50}$) | Total theoretical inactivation (log $TCID_{50}$) |
|---|---|---|---|---|---|---|---|
| PI-3 | Bovine | ss(−) RNA | Yes | Sensitive | ≥4.0* | ≥2.3 | ≥6.3 |
| FHV-1 | Feline | ds DNA | Yes | Sensitive | ≥3.5 | ≥2.6 | ≥6.1 |
| BEV | Bovine | ss(+) RNA | No | Resistant | 0.5 | 7.3 | 7.3 |

Abbreviations used:
PI-3: Parainfluenza virus type 3 (Paramyxoviridae);
FHV-1: Felid herpesvirus type 1 (Herpesviridae);
BEV: Bovine enterovirus (Picornaviridae);
TCID50: Tissue culture infective dose, 50%,
PAA: peracetic acid.
*Inactivation of model viruses following treatment with two detergent solutions in the presence of an osmotic gradient. Detergent solutions included 0.1% EDTA/0.028% Triton X-200 and 0.1% SDS.
**Inactivation of model viruses following treatment with 0.3% PAA/5% Ethanol in PBS. The results are expressed as "more or equal to" when the lower limit of virus recovery was limited by toxicity of the samples to mammalian cells.

Example 20

Viral Inactivation During Manufacture of Ovine FM Scaffolds

Viral inactivation during the production of FM scaffold can occur as a result of: 1) viral protein denaturation and/or disruption of viral lipids of the viral envelope during treatment with detergents (Triton X-200 and SDS); 2) the liberation of reactive oxygen species during peracetic acid (PAA) treatment; and 3) terminal sterilization using ethylene oxide. A study was undertaken to examine viral inactivation during the STOF processes and PAA treatment using three model viruses.

The level of viral inactivation was tested using a scaled-down manufacturing process. This involved spiking high-titre viral stocks of each of the three model viruses into Example 21

Fabrication of a Device for Breast Reconstruction

Wet sheets of naturally concave FM scaffold were aligned and successively layered onto one another to create 4-ply, 6-ply, and 8-ply laminates. The sheets were layered onto one another using a curved form that supported and complemented the natural contours of the FM scaffold. The laminates were freeze-dried to yield bonded laminates. These laminates were subsequently sewn together using a straight-stitch of vicryl suture, with a stitch length of approximately 3 mm. Laminates were sewn in straight lines following the curvature of the laminate. Stitch lines were separated by approximately 10 mm. The breast laminates were of either a crescent or ellipse shape, as illustrated in FIGS. 2A and 2B, respectively. The breast laminates can be affixed to native tissue using sutures or staples.

REFERENCES

Boguszewski, D. V., N. A. Dyment, et al. (2008). Biomechanical Comparison of Abdominal Wall Hernia Repair Materials. *ASME* 2008 *Summer Bioengineering Conference* Marriott Resort, Marco Island, Fla., ASME Choe, J. M., R. Kothandapani, et al. (2001). "Autologous, cadaveric, and synthetic materials used in sling surgery: comparative biomechanical analysis." *Urology* 58(3): 482-6.

Freytes, D. O., R. S. Tullius, et al. (2006). "Effect of storage upon material properties of lyophilized porcine extracellular matrix derived from the urinary bladder." *J Biomed Mater Res B Appl Biomater* 78(2): 327-33.

Freytes, D. O., R. S. Tullius, et al. (2008). "Hydrated versus lyophilized forms of porcine extracellular matrix derived from the urinary bladder." *J Biomed Mater Res A* 87(4): 862-72.

Gouk, S. S., T. M. Lim, et al. (2008). "Alterations of human acellular tissue matrix by gamma irradiation: histology, biomechanical property, stability, in vitro cell repopulation, and remodeling." *J Biomed Mater Res B Appl Biomater* 84(1): 205-17.

Lemer, M. L., D. C. Chaikin, et al. (1999). "Tissue strength analysis of autologous and cadaveric allografts for the pubovaginal sling." *Neurourol Urodyn* 18(5): 497-503.

Lindblad, W. J. (2006). "How should one study wound healing?" *Wound Repair Regen* 14(5): 515.

Lindblad, W. J. (2008). "Considerations for selecting the correct animal model for dermal wound-healing studies." *J Biomater Sci Polym Ed* 19(8): 1087-96.

Morgan, A. S., T. Mclff, et al. (2004). "Biomechanical properties of materials used in static facial suspension." *Arch Facial Plast Surg* 6(5): 308-10.

Sclafani, A. P., S. A. McCormick, et al. (2002). "Biophysical and microscopic analysis of homologous dermal and fascial materials for facial aesthetic and reconstructive uses." *Arch Facial Plast Surg* 4(3): 164-71.

Vural, E., N. McLaughlin, et al. (2006). "Comparison of biomechanical properties of alloderm and enduragen as static facial sling biomaterials." *Laryngoscope* 116(3): 394-6.

Zerris, V. A., K. S. James, et al. (2007). "Repair of the dura mater with processed collagen devices." *J Biomed Mater Res B Appl Biomater* 83(2): 580-8.

EQUIVALENTS

The invention has been described herein with reference to certain examples and embodiments only. No effort has been made to exhaustively describe all possible examples and embodiments of the invention. Indeed, those of skill in the art will appreciate that various additions, deletions, modifications and other changes may be made to the above-described examples and embodiments, without departing from the intended spirit and scope of the invention as recited in the following claims. It is intended that all such additions, deletions, modifications and other changes be included within the scope of the following claims.

INCORPORATION BY REFERENCE

The entire contents of all patents, published patent applications, websites, and other references cited herein are hereby expressly incorporated herein in their entireties by reference.

What is claimed is:

1. A method of covering a tissue deficit, comprising contacting the tissue deficit with a tissue scaffold comprising decellularized forestomach matrix of a ruminant mammal.

2. The method of claim 1, wherein the tissue deficit has a width of at least 10 cm and a length of at least 10 cm.

3. The method of claim 1, wherein the tissue scaffold increases proliferation of cells within the tissue deficit.

4. The method of claim 1, wherein the tissue scaffold increases vascularization within the tissue deficit.

5. A method of reinforcing soft tissue, comprising contacting the soft tissue with a tissue scaffold comprising decellularized forestomach matrix of a ruminant mammal.

6. The method of claim 5, wherein the tissue scaffold has a width of at least 10 cm and a length of at least 10 cm.

7. A method for inducing repair of a damaged tissue, comprising contacting the damaged tissue with a tissue scaffold comprising decellularized forestomach matrix of a ruminant mammal.

8. A method for stimulating soft tissue regeneration, comprising contacting the soft tissue with a tissue scaffold comprising decellularized forestomach matrix of a ruminant mammal.

9. The method of claim 7 or 8, wherein the tissue scaffold induces cell proliferation.

10. The method of claim 7 or 8, wherein the tissue scaffold induces vascularization.

11. A method of inducing vascularization of a tissue, comprising contacting the tissue with a tissue scaffold comprising decellularized forestomach matrix of a ruminant mammal, such that vascularization occurs within the tissue.

12. The method of any one of claim 1, 5, 7, 8 or 11, wherein the ruminant is *Ovis aries*.

13. The method of any one of claim 1, 5, 7, 8 or 11, wherein the tissue scaffold is derived from the rumen.

14. The method of any one of claim 1, 5, 7, 8 or 11, wherein the tissue scaffold further comprises decellularized tissue selected from the group consisting of epithelium, basement membrane, tunica muscularis, and combinations thereof.

15. The method of any one of claim 1, 5, 7, 8 or 11, wherein the tissue scaffold is formatted as a laminated sheet comprising 2-12 layers of said scaffold.

16. The method of claim 15, wherein the tissue scaffold comprises a polymer positioned between two or more layers of said laminated sheet.

* * * * *